(12) United States Patent
Ashcraft et al.

(10) Patent No.: US 11,285,162 B2
(45) Date of Patent: Mar. 29, 2022

(54) METHODS, COMPOSITIONS, AND KITS FOR TREATING AND/OR PREVENTING A SIDE EFFECT ASSOCIATED WITH RADIATION AND/OR CHEMOTHERAPY EXPOSURE

(71) Applicants: BioMimetix JV, LLC, Englewood, CO (US); Duke University, Durham, NC (US)

(72) Inventors: Kathleen Ashcraft, Durham, NC (US); Mark Dewhirst, Chapel Hill, NC (US); Ines Batinic-Haberle, Durham, NC (US); James D. Crapo, Englewood, CO (US)

(73) Assignees: BioMimetix JV, LLC, Englewood, CO (US); Duke University, Durham, NC (US)

( * ) Notice: Subject to any disclaimer, the term of this patent is extended or adjusted under 35 U.S.C. 154(b) by 117 days.

(21) Appl. No.: 16/500,490

(22) PCT Filed: Apr. 4, 2018

(86) PCT No.: PCT/US2018/026002
§ 371 (c)(1),
(2) Date: Oct. 3, 2019

(87) PCT Pub. No.: WO2018/187411
PCT Pub. Date: Oct. 11, 2018

(65) Prior Publication Data
US 2021/0106594 A1  Apr. 15, 2021

Related U.S. Application Data

(60) Provisional application No. 62/481,460, filed on Apr. 4, 2017.

(51) Int. Cl.
| | | |
|---|---|---|
| *A61K 31/555* | (2006.01) | |
| *A61P 35/00* | (2006.01) | |
| *A61K 9/00* | (2006.01) | |
| *A61K 31/495* | (2006.01) | |
| *A61K 33/243* | (2019.01) | |
| *A61K 45/06* | (2006.01) | |
| *A61P 17/00* | (2006.01) | |
| *A61P 43/00* | (2006.01) | |

(52) U.S. Cl.
CPC ............ *A61K 31/555* (2013.01); *A61P 35/00* (2018.01)

(58) Field of Classification Search
CPC .. A61K 31/555; A61K 33/243; A61K 31/495; A61K 9/0019; A61K 45/06; A61K 2300/00; A61P 35/00; A61P 17/00; A61P 43/00
See application file for complete search history.

(56) References Cited

U.S. PATENT DOCUMENTS

| | | |
|---|---|---|
| 8,618,089 B2 | 12/2013 | Batinic-Haberle et al. |
| 2006/0199792 A1 | 9/2006 | Groves et al. |
| 2007/0149498 A1 | 6/2007 | Crapo et al. |
| 2011/0275606 A1 | 11/2011 | Batinic-Haberle et al. |
| 2015/0344509 A1 | 12/2015 | Batinic-Haberle et al. |
| 2016/0324868 A1 | 11/2016 | Ji et al. |

FOREIGN PATENT DOCUMENTS

| | | |
|---|---|---|
| WO | 2008095366 A1 | 8/2008 |
| WO | 2010080881 A1 | 7/2010 |
| WO | 2015034777 A1 | 3/2015 |
| WO | 2015034778 A1 | 3/2015 |
| WO | 2015112586 A1 | 7/2015 |
| WO | 2015112588 A1 | 7/2015 |
| WO | 2018118891 A1 | 6/2018 |
| WO | 2018237249 A1 | 12/2018 |
| WO | 2019067523 A1 | 4/2019 |

OTHER PUBLICATIONS

Weitzel, D.H.,"Radioprotection of the brain white matter by Mn (III) N-butoxyethylpyridylporphyrin-based superoxide dismutase mimic MnTnBuOE-2-PyP5+." Molecular cancer therapeutics 14.1 (2015): 70-79.*
Ashcraft, K.A., International Journal of Radiation Oncology 2015 93(4):892-900; Supplemental Figure 2A.*
Archambeau, J. et al. "Superoxide dismutase mimic, MnTE-2-PyP5+ ameliorates acute and chronic proctitis following focal proton irradiation of the rat rectum" Redox Biology, 1:599-607 (2013).
Bao, F. et al. "Hydroxyl radicals generated in the rat spinal cord at the level produced by impact injury induce cell death by necrosis and apoptosis: protection by a metalloporphyrin" Neuroscience, 126(2):285-295 (2004).
Batinic-Haberle, I. et al. "Design of Mn porphyrins for treating oxidative stress injuries and their redox-based regulation of cellular transcriptional activities" Amino Acids, 42(1):95-113 (2012).
Batinic-Haberle, I. et al. "Diverse functions of cationic Mn(III) N-substituted pyridylporphyrins, recognized as SOD mimics" Free Radicical Biology & Medicine, 51(5):1035-1053 (2011).
Batinic-Haberle, I. et al. "Mechanistic considerations of the therapeutic effects of Mn porphyrins, commonly regarded as SOD mimics" Anticancer Therapy: Lessons from Brain and Lymphoma Studies, Free Radical Biology & Medicine, 65 (Supplement 2): S120-121 (2013).
Batinic-Haberle, I. et al. "Superoxide dismutase mimics: chemistry, pharmacology, and therapeutic potential" Antioxidants & Redox Signal, 13(6):877-918 (2010).

(Continued)

*Primary Examiner* — John M Mauro
(74) *Attorney, Agent, or Firm* — Myers Bigel, P.A.

(57) ABSTRACT

Described herein are methods, compositions, and kits for treating and/or preventing in a subject one or more side effects associated with radiation and/or chemotherapy exposure, including methods, compositions and kits that include an active agent at a low dose. In some embodiments, methods, compositions, and kits for treating and/or preventing tissue damage in a subject are provided, including methods, compositions and kits that include an active agent at a low dose.

52 Claims, 10 Drawing Sheets

(56) References Cited

OTHER PUBLICATIONS

Batinic-Haberle, I. et al. "SOD therapeutics: latest insights into their structure-activity relationships and impact on the cellular redox-based signaling pathways" Antioxidants & redox signaling, 20(15):2372-2415 (2014).

Beck L. A. et al. "Dupilumab treatment in adults with moderate-to-severe atopic dermatitis" New England Journal of Medicine, 371(2):130-139 (2014).

Birer, S. R. et al. "Inhibition of the continuum of radiation-induced normal tissue injury by a redox-active Mn porphyrin" Radiation Research, 188(1):94:104 (2017).

Bottino R. et al. "Preservation of human islet cell functional mass by anti-oxidative action of a novel SOD mimic compound" Diabetes, 51(8):2561-2567 (2002).

Bottino R. et al. "Response of human islets to isolation stress and the effect of antioxidant treatment" Diabetes, 53(10):2559-2568 (2004).

Bristol-Myers Squibb "FDA Oncology Tools Approval Summary for Cisplatin for Metastatic Ovarian Tumors. Food and Drug Administration, Center for Drug Evaluation and Research" Archived from the original on Feb. 8, 2008. (1978) http://web.archive.org/web/20080208232952/http://www.accessdata.fda.gov/scripts/cder/onctools/summary.cfm?ID=73.

Brizel D. M. et al. "Phase III randomized trial of amifostine as a radioprotector in head and neck cancer" Journal of Clinical Oncology, 18(19):3339-3345 (2000).

Butler, J.M., Jr., et al. "A phase III, double-blind, placebo-controlled prospective randomized clinical trial of d-threo-methylphenidate HCl in brain tumor patients receiving radiation therapy" International Journal of Radiatian Oncology, Biology, Physics, 69(5):1496-1501 (2007).

Campa M. et al. "A review of biologic therapies targeting IL-23 and IL-17 for use in moderate-to-severe plaque psoriasis" Dermatology and Therapy, 6(1):1-12 (2016).

Choudhury, K. R. et al. "Dynamic treatment effect (DTE) curves reveal the mode of action for standard and experimental cancer therapies" Oncotarget, 6(16):14656-1468 (2015).

Cotrim A. P. et al. "Kinetics of tempol for prevention of xerostomia following head and neck irradiation in a mouse model" Clinical Cancer Research: An Official Journal of the American Association for Cancer Research, 11(20):7564-7568 (2005).

Delmastro M. M. "Modulation of redox balance leaves murine diabetogenic TH1 T cells "LAG-3-ing" behind" Diabetes, 61(7): 1760-1768 (2012).

Delmastro M. M. et al. "Oxidative stress and redox modulation potential in type 1 diabetes" Clinical and Developmental Immunology, 2011:593863 (2011).

Delmastro-Greenwood, M. M. et al. "Mn porphyrin regulation of aerobic glycolysis: implications on the activation of diabetogenic immune cells" Antioxidants & Redox Signaling, 19(16):1902-1915 (2013).

El-Batawy M. M. et al. "Topical calcineurin inhibitors in atopic dermatitis: a systematic review and meta-analysis" Journal of Dermatological Science, 54(2):76-87 (2009).

Elting L.S. et al. "Risk, outcomes, and costs of radiation-induced oral mucositis among patients with head-and-neck malignancies" International Journal of Radiation Oncology, Biology, Physics, 68(4):1110-1120 (2007).

Eyerich K. "Immunology of atopic eczema: overcoming the Th1/Th2 paradigm" Allergy, 68(8):974-982 (2013).

Fujiwara N. et al. "miR-634 Activates the Mitochondrial Apoptosis Pathway and Enhances Chemotherapy-Induced Cytotoxicity" Cancer Research, 75(18):3890-3901 (2015).

Gad, S. C. et al. "A nonclinical safety assessment of MnTE-2-PyP, a manganese porphyrin" International Journal of Toxicology, 32(4):274-287 (2013).

Gad, S. C. et al. "Nonclinical Safety and Toxicokinetics of MnTnBuOE-2-PyP5+ (BMX-001)" International Journal of Toxicology, 35(4):438-453 (2016).

Garofalo, M.C., et al. "A pilot study in rhesus macaques to assess the treatment efficacy of a small molecular weight catalytic metalloporphyrin antioxidant (AEOL 10150) in mitigating radiation-induced lung damage" Health Phys Society, 106(1):73-83 (2014).

Gauter-Fleckenstein, B. et al. "Robust rat pulmonary radioprotection by a lipophilic Mn N-alkylpyridylporphyrin, MnTnHex-2-PyP+" Redox Biology, 2:400-410 (2014).

Gerber D. E. et al. "The impact of thrombocytopenia from temozolomide and radiation in newly diagnosed adults with high-grade gliomas" Neuro-Oncology, 9(1):47-52 (2006).

Ghoreschi K, et al. "Immunopathogenesis and role of T cells in psoriasis" Clinics in Dermatology, 25(6):574-580 (2007).

Giro C. et al. "High rate of severe radiation dermatitis during radiation therapy with concurrent cetuximab in head and neck cancer: Results of a survey in EORTC institutes" Radiotherapy and Oncology, 90(2):166-171 (2009).

Gittler J. K. et al. "Progressive activation of T(H)2/T(H)22 cytokines and selective epidermal proteins characterizes acute and chronic atopic dermatitis" Journal of Allergy Clinical Immunology, 130(6):1344-1354 (2012).

Gridley, D.S. et al. "Radiation and a metalloporphyrin radioprotectant in a mouse prostate tumor model" Anticancer Research, 27(5A):3101-3109 (2007).

Habl G. et al. "Differentiation of irradiation and cetuximab induced skin reactions in patients with locally advanced head and neck cancer undergoing radioimmunotherapy: the HICARE protocol" BMC Cancer, 13(1):345 (2013).

International Preliminary Report on Patentability corresponding to International Patent Application No. PCT/US2018/026007 (9 pages) (dated Oct. 17, 2019).

Jaramillo et al. "Manganese (III) meso-tetrakis N-ethylpyridinium-2-yl porphyrin acts as a pro-oxidant to inhibit electron transport chain proteins, modulate bioenergetics, and enhance the response to chemotherapy in lymphoma cells" Free Radical Biology & Medicine, 83(2015).

Johnson L. B. et al. "Radiation enteropathy and leucocyte-endothelial cell reactions in a refined small bowel model" BMC Surgery, 4:10 (2004).

Khan, I. et al. "Effect of potent redox-modulating manganese porphyrin, MnTM-2-PyP, on the Na(+)/H(+) exchangers NHE-1 and NHE-3 in the diabetic rat" Redox Report, 14(6):236-242 (2009).

Kimura H. et al. "Inhibition of radiation-induced up-regulation of leukocyte adhesion to endothelial cells with the platelet-activating factor inhibitor, BN52021" International Journal of Radiation, Oncology, Biology, Physics, 33(3):627-633 (1995).

Koga, F., et al. "ErbB2 and NFkappaB overexpression as predictors of chemoradiation resistance and putative targets to overcome resistance in muscle-invasive bladder cancer" PLoS One, 6(11):e27616 (2011).

Koyama G. et al. "Novel approaches to topical psoriasis therapy" International Journal of Pharmaceutical Compounding, 19(5):357-365 (2015) Abstract.

Kwei K. A. et a. "Transcriptional repression of catalase in mouse skin tumor progression" Neoplasia, 6(5):440-448 (2004).

Lakritz J. et al. "Validated High-Performance Liquid Chromatography-Electrochemical Method for Determination of Glutathione and Glutathione Disulfide in Small Tissue Samples" Analytical Biochemistry, 247(1):63-68 (1997).

Lauffer F. et al. "Target-oriented therapy: Emerging drugs for atopic dermatitis" Expert Opinion on Emerging Drugs, 21(1):81-89 (2016).

Lee, M.Y. et al. "Senescence of cultured porcine coronary arterial endothelial cells is associated with accelerated oxidative stress and activation of NFkB" Journal of Vascular Research, 47(4):287-298 (2010).

Levi J. A. et al. "Haemolytic anaemia after cisplatin treatment" British Medical Journal (Clin Res Ed) 282(6281):2003-2004 (1981).

Li, H., et al. "Mn(III) meso-tetrakis-(N-ethylpyridinium-2-yl) porphyrin mitigates total body irradiation-induced long-term bone marrow suppression" Free Radical Biology & Medicine, 51(1):30-37 (2011).

(56) References Cited

OTHER PUBLICATIONS

Ling, X. et al. "Temporal and spatial profiles of cell loss after spinal cord injury: Reduction by a metalloporphyrin" Journal of Neuroscience Research, 85(10):2175-2185 (2007).
Liu, D., et al. "Peroxynitrite generated at the level produced by spinal cord injury induces peroxidation of membrane phospholipids in normal rat cord: reduction by a metalloporphyrin" Journal of Neurotrauma, 22(10):1123-1133 (2005).
Loehrer P. J. et al. "Drugs five years later: Cisplatin" Annals of Internal Medicine, 100(5):704-713 (1984).
Lomeli N. et al. "Cisplatin-induced mitochondrial dysfunction is associated with impaired cognitive function in rats" Free Radical Biology Medicine, 102:274-286 (2017).
Marullo R. et al. "Cisplatin induces a mitochondrial-ROS response that contributes to cytotoxicity depending on mitochondrial redox status and bioenergetic functions" PloS one, 8(11):e81162 (2013).
Mason A. R. et al. "Topical treatments for chronic plaque psoriasis" Cochrane Database System Review, 3:CD005028 (2013).
Milosavljevic N. et al. "Nongenomic effects of cisplatin: acute inhibition of mechanosensitive transporters and channels without actin remodeling" Cancer Research, 70(19):7514-7522 (2010).
Moeller, B.J. et al. "Pleiotropic effects of HIF-1 blockade on tumor radiosensitivity" Cancer Cell, 8(2):99-110 (2005).
Moeller, B.J. et al. "Radiation activates HIF-1 to regulate vascular radiosensitivity in tumors: role of reoxygenation, free radicals, and stress granules" Cancer Cell, 5(5):429-441 (2004).
Moore T. et al. "A new LC-MS/MS method for the clinical determination of reduced and oxidized glutathione from whole blood" Journal of Chromatography B, Analytical Technologies in the Biomedical and Life Sciences, 929:51-55 (2013).
Morgan-Bathke M. et al. "The Rapalogue, CCI-779, improves salivary gland function following radiation" PloS one, 9(12):e113183 (2014).
Moulder, J. E. "Future strategies for mitigation and treatment of chronic radiation-induced normal tissue injury" Seminars in Radiation Oncology, 17(2):141-148 (2007).
National Institute for Health and Care Excellence, "Psoriasis: Assessment and Management of Psoriasis" National Clinical Guideline Centre, Clinical Guideline, Published: Oct. 24, 2012 (56 pages).
NRG Oncology "RTOG 0920: A Phase III Study of Postoperative Radiation Therapy (IMRT) /- Cetuximab for Locally-Advanced Resected Head and Neck Cancer" Version Date: Jan. 25, 2016 (100 pages).
Palmer C. N. A. et al. "Common loss-of-function variants of the epidermal barrier protein filaggrin are a major predisposing factor for atopic dermatitis" Nature Genetics, 38(4):441-446 (2006).
Pham, Christine T.N. "Neutrophil serine proteases: specific regulators of inflammation" Natuere Reviews Immunology, 6(7):541-550 (2006).
Piganelli, J. D. et al. "A metalloporphyrin-based superoxide dismutase mimic inhibits adoptive transfer of autoimmune diabetes by a diabetogenic T-cell clone" Diabetes, 51(2):347-355 (2002).
Pringle S. et al. "Concise Review: Adult Salivary Gland Stem Cells and a Potential Therapy for Xerostomia" Stem Cells, 31(4):613-619 (2013).
Rabbani, Z.N. et al. "Antiangiogenic action of redox-modulating Mn(III) meso-tetrakis(N-ethylpyridinium-2-yl)porphyrin, MnTE-2-PyP(5+), via suppression of oxidative stress in a mouse model of breast tumor" Free Radicical Biology & Medicine, 47(7):992-1004 (2009).
Rades D. et al. "Serious adverse effects of amifostine during radiotherapy in head and neck cancer patients" Radiotherapy and Oncology, 70(3):261-264 (2004).
Rajic, Z et al. "A new SOD mimic, Mn(III) ortho N-butoxyethylpyridylporphyrin, combines superb potency and lipophilicity with low toxicity" Free Radical Biology and Medicine, 52(9):1828-1834 (2012).
Ross, A.D., et al., Hemodynamic effects of metalloporphyrin catalytic antioxidants: structure-activity relationships and species specificity. Free Radic Biol Med, 2002. 33(12): p. 1657-1669.
Russo G. et al. "Radiation treatment breaks and ulcerative mucositis in head and neck cancer" The Oncologist, 13(8):886-898, (2008).
Santos et al. "Hydroxyl radical scavenger ameliorates cisplatin-induced nephrotoxicity by preventing oxidative stress, redox state unbalance, impairment of energetic metabolism and apoptosis in rat kidney mitochondria" Cancer Chemo Pharm, 61(1):145-155 (2008).
Schmidt-Ullrich, Rupert K. "Molecular targets in radiation oncology" Oncogene, 22(37):5730-5733 (2003).
Schreck, R. et al. "Nuclear factor kappa B: an oxidative stress-responsive transcription factor of eukaryotic cells (a review)" Free Radical Research Community, 17(4):221-237 (1992).
Semenza, G.L. "Oxygen sensing, homeostasis, and disease" New England Journal of Medicine, 365(6):537-547 (2011).
Shaw, E.G. et al. "Phase II study of donepezil in irradiated brain tumor patients: effect on cognitive function, mood, and quality of life" Journal of Clinical Oncology, 24(9):1415-1420 (2006).
Sheng, H. et al. "Long-term neuroprotection from a potent redox-modulating metalloporphyrin in the rat" Free Radical Biol Med 47(7):917-923 (2009).
Sheng, H. et al. "Neuroprotective efficacy from a lipophilic redox-modulating Mn(III) N-Hexylpyridylporphyrin, MnTnHex-2-PyP: rodent models of ischemic stroke and subarachnoid hemorrhage" Journal of Pharmacology and Experimental Therapeutics, 338(3):906-916 (2011).
Sheng, H., et al. "Effects of metalloporphyrin catalytic antioxidants in experimental brain ischemia" Free Radical Biology & Medicine, 33(7):947-961 (2002).
Sklavos, M. M. et al. "Redox modulation inhibits CD8 T cell effector function" Free Radical Biology & Medicine, 45(10): 1477-1486 (2008).
Sklavos, M. M. et al. "Redox modulation protects islets from transplant-related injury" Diabetes, 59(7):1731-1738 (2010).
Sorokina L. V. et al. "The evaluation of prooxidant and antioxidant state of two variants of lewis lung carcinoma: a comparative study" Experimental Oncology, 32(4):249-253 (2010).
Spasojevic, I. et al. "Manganese(III) Biliverdin IX Dimethyl Ester: A Powerful Catalytic Scavenger of Superoxide Employing the Mn(III)/Mn(IV) Redox Couple" Inorg. Chem., 40:726-739 (2001).
Stone H.B., et al. "Models for evaluating agents intended for the prophylaxis, mitigation and treatment of radiation injuries" Report of an NCI Workshop, Dec. 3-4, 2003. Radiation Research, 162(6):711-728 (2004).
Stupp, R., et al. "Radiotherapy plus concomitant and adjuvant temozolomide for glioblastoma" New England Journal of Medicine, 352(10):987-996 (2005).
Takahashi, I., et al. "Clinical study of the radioprotective effects of Amifostine (YM-08310, WR-2721) on chronic radiation injury" International Journal of Radiation Oncology, Biology, Physics, 12(6):935-938 (1986).
Tannehill, S.P. et al. "Amifostine and radiation therapy: past, present, and future" Seminars in Oncology, 23(4 Suppl 8):69-77 (1996) Abstract.
Thomsen, Simon Francis "Atopic dermatitis: natural history, diagnosis, and treatment" ISRN Allergy, 354250. PMC4004110. (2014).
Tovmasyan et al. "Design, Mechanism of Action, Bioavailability and Therapeutic Effects of Mn Porphyrin-Based Redox Modulators" Medical Principles and Practice, 22(2):103-130 (2013).
Tovmasyan, A. et al. "Anticancer therapeutic potential of Mn porphyrin/ascorbate system" Free Radical Biology and Medicine, 89:1231-1247 (2015).
Trzaska, Stephen "Cisplatin" Chemical and Engineering News, 83(25) (2005).
Tse H. M. et al. "Mechanistic analysis of the immunomodulatory effects of a catalytic antioxidant on antigen-presenting cells: implication for their use in targeting oxidation-reduction reactions in innate immunity" Free Radical Biology & Medicine, 36(2):233-247 (2004).
Van Luijk P. et al. "Sparing the region of the salivary gland containing stem cells preserves saliva production after radiotherapy for head and neck cancer" Science Translational Medicine, 7(305):305ra147 (2005).
Vissink, A. et al. "Oral sequelae of head and neck radiotherapy" Critical Reviews in Oral Biology & Medicine, 14(3):199-212 (2003).

(56) References Cited

OTHER PUBLICATIONS

Wasserman et al. "Influence of intravenous amifostine on xerostomia, tumor control, and survival after radiotherapy for head-and-neck cancer: 2-year follow-up of a prospective, randomized, phase III trial" International Journal of Radiation Oncology, Biology, Physics, 63(4):985-990 (2005).
Weitner et al. "Comprehensive pharmacokinetic studies and oral bioavailability of two Mn porphyrin-based SOD mimics, MnTE-2-PyP5+ and MnTnHex-2-PyP5+" Free Radical Biology and Medicine, 58:73-80 (2013).
Weitzel D. H. et al. "Neurobehavioral radiation mitigation to standard brain cancer therapy regimens by Mn(III) n-butoxyethylpyridylporphyrin-based redox modifier" Environmental Molecular Mutagenesis, 57(5):372-381 (2016).
Windsor R. E. et al. "Germline genetic polymorphisms may influence chemotherapy response and disease outcome in osteosarcoma: A pilot study" Cancer, 118(7):1856-1867 (2012).
Zeidan Y. H. et al. "Botulinum Toxin Confers Radioprotection in Murine Salivary Glands" International Journal of Radiation Oncology, Biology, Physics, 94(5):1190-1197 (2016).
Zitka O. et al. "Redox status expressed as GSH:GSSG ratio as a marker for oxidative stress in paediatric tumour patients" Oncology Letters, 4(6):1247-1253 (2012).
Extended European Search Report corresponding to European Patent Application No. 18781786.1 (11 pages) (dated Sep. 25, 2020).
Stover et al. "Topically applied manganese-porphyrins BMX-001 and BMX-010 display a significant anti-inflammatory response in a mouse model of allergic dermatitis" Archives of Dermatological Research, 308:711-721 (2016).
Ashcraft et al. "Novel Manganese-Porphyrin Superoxide Dismutase-Mimetic Widens the Therapeutic Margin in a Preclinical Head and Neck Cancer Model" International Journal of Radiation Oncology, 93(4):892-900 (2015).
International Search Report and the Written Opinion of the International Searching Authority corresponding to International Patent Application No. PCT/US2018/026002 (11 pages) (dated Aug. 23, 2018).
Weitzel et al. "Radioprotection of the Brain White Matter by Mn(III) N-Butoxyethylpyridylporphyrin-Based Superoxide Dismutase Mimic MnTnBuOE-2-PyP5+" Molecular Cancer Therapeutics, 14:70-79 (2015).
Abdollah, F. et al. "A competing-risks analysis of survival after alternative treatment modalities for prostate cancer patients: 1988-2006" European Urology, 59:88-95 (2011).
Allen, B. G. et al. "Pharmacological ascorbate enhances chemo-radio-sensitization in brain and lung cancer" Free Radical Biology & Medicine, 53:S39 (2012).
Aluise, C. D. et al. "2-Mercaptoethane sulfonate prevents doxorubicin induced plasma protein oxidation and TNF-α release: implications for the reactive oxygen species mediated mechanisms of chemobrain" Free Radical Biology & Medicine, 11:1630-1638 (2011).
American Cancer Society, "Cancer Facts & Figures 2014" American Cancer Society, Inc., 72 pages (2014).
Amii, H. et al. "Flow microreactor synthesis in organo-fluorine chemistry" Beilstein Journal of Organic Chemistry, 9:2793-2802 (2013).
Bache, S. T. et al. "Investigating the accuracy of microstereotactic-body-radiotherapy utilizing anatomically accurate 3D printed rodentmorphic dosimeters" Medical Physics, 42(2):846 (2015).
Batinic-Haberle, I. et al. "52 Chemistry, biology and medical effects of water soluble metalloporphyrins" Handbook of Porphyrin Science, 11:291-393 (2011).
Batinic-Haberle, I. et al. "A Combination of Two Antioxidants (An SOD Mimic and Ascorbate) Produces a Pro-Oxidative Effect Forcing *Escherichia coli* to Adapt via Induction of oxyR Regulon" Anticancer Agents in Medicinal Chemistry, 11(4):329-340 (2011).
Batinic-Haberle, I. et al. "An educational overview of the chemistry, biochemistry and therapeutic aspects of Mn porphyrins—From superoxide dismutation to H2O2-driven pathways" Redox Biology, 5:43-65 (2015).
Batinic-Haberle, I. et al. "Complex chemistry and biology of redox-active compounds, commonly known as SOD mimics, affect their therapeutic effects" Antioxidants & Redox Signaling, 20(15):2323-2325 (2014).
Batinic-Haberle, I. et al. "Manganese(III) Meso Tetrakis Ortho N-alkylpyridylporphyrins. Synthesis, Characterization and Catalysis of O2-Dismutation" Journal of the Chemical Society, Dalton Transactions, 13(13):2689-2696 (2002).
Batinic-Haberle, I. et al. "New class of potent catalysts of O2.-dismutation. Mn(III) methoxyethylpyridyl- and methoxyethylimidazolylporphyrins" Dalton Transactions, 11:1696-1702 (2004).
Batinic-Haberle, I. et al. "The complex mechanistic aspects of redox-active compounds, commonly regarded as SOD mimics" BioInorganic Reaction Mechanisms, 9(1-4):35-58 (2013).
Batinic-Haberle, I. et al. "The Ortho Effect Makes Manganese (III) Meso-Tetrakis(N-methylpyridinium-2-yl)Porphyrin (MnTM-2-PyP) a Powerful and Potentially Useful Superoxide Dismutase Mimic" The Journal of Biological Chemistry, 273(38):24521-24528 (1998).
Batinic-Haberle, et al. "Relationship among Redox Potentials, Proton Dissociation Constants of Pyrrolic Nitrogens, and in Vivo and in Vitro Superoxide Dismutating Activities of Manganese(III) and Iron(III) Water-Soluble Porphyrins" Inorganic Chemistry, 38:4011-4022 (1999).
Benov, L. et al. "Protein damage by photo-activated Zn(II) N-alkylpyridylporphyrins" Amino Acids, 42(1): 117-128 (2012).
Bhattacharyya, J. et al. "A paclitaxel-loaded recombinant polypeptide nanoparticle outperforms Abraxane in multiple murine cancer models" Nature Communications, 6:7939 (2015).
Breckwoldt, M. O. et al. "Multiparametric optical analysis of mitochondrial redox signals during neuronal physiology and pathology in vivo" Nature Medicine, 20(5):555-560 (2014).
Cao, Y. T. et al. "Observation of incipient tumor angiogenesis that is independent of hypoxia and hypoxia inducible factor-1 activation" Cancer Research, 65(13):5498-5505 (2005).
Celic, T. et al. "Mn porphyrin-based SOD mimic, MnTnHex-2-PyP(5+), and non-SOD mimic, MnTBAP(3-), suppressed rat spinal cord ischemia/reperfusion injury via NF-kappaB pathways" Free Radical Research, 48(12):1426-1442 (2014).
Chen, Q. et al. "Ascorbate in pharmacologic concentrations selectively generates ascorbate radical and hydrogen peroxide in extracellular fluid in vivo" Proceedings of the National Academy of Sciences, 104(21):8749-8754 (2007).
Chen, Q. et al. "Pharmacologic doses of ascorbate act as a prooxidant and decrease growth of aggressive tumor xenografts in mice" Proceedings of the National Academy of Sciences, 105(32):11105-11109 (2008).
Cong, Z. X. et al. "ERK and PI3K signaling cascades induce Nrf2 activation and regulate cell viability partly through Nrf2 in human glioblastoma cells" Oncology Reports, 30(2):715-722 (2013).
Crawford, S. "Anti-inflammatory/antioxidant use in long-term maintenance cancer therapy: a new therapeutic approach to disease progression and recurrence" Therapeutic Advances in Medical Oncology, 6(2):52-68 (2014).
Dewhirst, M. W. "Relationships between Cycling Hypoxia, HIF-1, Angiogenesis and Oxidative Stress" Radiation Research, 172(6):653-665 (2009).
Dhar, S. K. et al. "Manganese superoxide dismutase is a p53-regulated gene that switches cancers between early and advanced stages" Cancer Research, 71(21):8864-8895 (2011).
Dinan, M. A. et al. "Changes in initial treatment for prostate cancer among Medicare beneficiaries, 1999-2007" International Journal of Radiation Oncology, Biology, Physics, 82(5):e781-786 (2012).
Dong, C. et al. "Loss of FBP1 by snail-mediated repression provides metabolic advantages in basal-like breast cancer" Cancer Cell, 23(3):316-331 (2013).
Dorai, T. et al. "Amelioration of renal ischemia-reperfusion injury with a novel protective cocktail" The Journal of Urology, 186(6):2448-2454 (2011).
Driscoll, J. et al. "Antitumor properties of 2(1H)-pyrimidinone riboside (zebularine) and its fluorinated analogues" Journal of Medicinal Chemistry, 34(11):3280-3284 (1991).

(56) References Cited

OTHER PUBLICATIONS

Engelmann, F. M. et al. "Determination of n-octanol/water partition and membrane binding of cationic porphyrins" International Journal of Pharmaceutics, 329(1-2):12-18 (2007).
Evans, M. K. et al. "Mn porphyrin in combination with ascorbate acts as a pro-oxidant and mediates caspase-independent cancer cell death" Free Radical Biology and Medicine, 68:302-314 (2014).
Ezzeddine, R. et al. "Effect of Molecular Characteristics on Cellular Uptake, Subcellular Localization, and Phototoxicity of Zn(II) N-Alkylpyridylporphyrins" The Journal of Biological Chemistry, 288(51):36579-36588 (2013).
Fernandes, A. S. et al. "Combined effect of the SOD mimic MnTnHex-2-PyP5+ and doxorubicin on the migration and invasiveness of breast cancer cells" Toxicology Letters, 221(S):S70-S71 (2013).
Ferrer-Sueta, G. et al. "Reactions of Manganese Porphyrins with Peroxynitrite and Carbonate Radical Anion" The Journal of Biological Chemistry, 278(30):27432-27438 (2003).
Filler, R. et al. "Fluorine in medicinal chemistry: a century of progress and a 60-year retrospective of selected highlights" Future Medicinal Chemistry, 1(5):777-791 (2009).
Forman, H. J. et al. "Signaling functions of reactive oxygen species" Biochemistry, 49(5):835-842 (2010).
Fuchs, J. et al. "Modulation of UV-light-induced skin inflammation by D-alpha-tocopherol and L-ascorbic acid: a clinical study using solar simulated radiation" Free Radical Biology and Medicine, 25(9):1006-1012 (1998).
Fugl-Meyer, A. R. et al. "On life satisfaction in male erectile dysfunction" International Journal of Impotence Research, 9(3):141-148 (1997).
Gauter-Fleckenstein, B. et al. "Early and late administration of antioxidant mimic MnTE-2-PyP5+ in mitigation and treatment of radiation-induced lung damage" Free Radical Biology and Medicine, 48(8):1034-1043 (2010).
Gaye, B. et al. "Fluorinated molecules in the diagnosis and treatment of neurodegenerative diseases" Future Medicinal Chemistry, 1(5):821-823 (2009).
Geismann, C. et al. "Cytoprotection "gone astray": Nrf2 and its role in cancer" OncoTargets and Therapy, 7:1497-1518 (2014).
Gius, D. et al. "Redox Signaling in Cancer Biology" Antioxidants & Redox Signaling, 8(7-8):1249-1252 (2006).
Gravemann, U. et al. "Hydroxamic acid and fluorinated derivatives of valproic acid: Anticonvulsant activity, neurotoxicity and teratogenicity" Neurotoxicology and Teratology, 30(5):390-394 (2008).
Hayes, J. D. et al. "The Nrf2 regulatory network provides an interface between redox and intermediary metabolism" Trends in Biochemical Sciences, 39(4):199-218 (2014).
Hempel, N. et al. "Manganese superoxide dismutase (Sod2) and redox-control of signaling events that drive metastasis" Anticancer Agents in Medicinal Chemistry, 11(2):191-201 (2011).
Hoffman, K. E. et al. "Risk of late toxicity in men receiving dose-escalated hypofractionated intensity modulated prostate radiation therapy: results from a randomized trial" Int J of Radiation Oncology, Biology, Physics, 88(5):1074-1084 (2014).
Il'yasova, D. et al. "Individual responses to chemotherapy-induced oxidative stress" Breast Cancer Research and Treatment, 125(2):583-589 (2011).
Jaal, J. et al. "Radiation Induced Inflammatory Changes in the Mouse Bladder: The Role of Cyclooxygenase-2" Journal of Urology, 175(4):1529-1533 (2006).
Jaramillo, M. C. et al. "Manganese Porphyrin, MnTE-2-PyP5+, Acts as a Pro-Oxidant to Potentiate Glucocorticoid-Induced Apoptosis in Lymphoma Cells" Free Radical Biology and Medicine, 52(8):1272-1284 (2012).
Jaramillo, M. C. et al. "The emerging role of the Nrf2-Keap1 signaling pathway in cancer" Genes & Development, 27:2179-2191 (2013).
Jin, G. et al. "Disruption of wild-type IDH1 suppresses D-2-hydroxyglutarate production in IDH1-mutated gliomas" Cancer Research, 73(2):496-501 (2013).
Jones, D. P. "Redox potential of GSH/GSSG couple: assay and biological significance" Methods in Enzymology, 348:93-112 (2002).
Jones, D. P. et al. "Redox state of glutathione in human plasma" Free Radical Biology and Medicine, 28(4):625-635 (2000).
Jones, L. W. et al. "Effects of non-linear aerobic training on erectile dysfunction and cardiovascular function following radical prostatectomy for clinically-localized prostate cancer" European Urology, 65(5):852-855 (2014).
Jumbo-Lucioni, P. P. et al. "Manganese-Based Superoxide Dismutase Mimics Modify Both Acute and Long-Term Outcome Severity in a *Drosophila melanogaster* Model of Classic Galactosemia" Antioxidants & Redox Signaling, 20(15):2361-2371 (2014).
Jungsuwadee P. et al. "The Metalloporphyrin Antioxidant, MnTE-2-PyP, Inhibits Th2 Cell Immune Responses in an Asthma Model" International Journal of Molecular Sciences, 13(8):9785-9797 (2012).
Kachadourian, R. et al. "Syntheses and Superoxide Dismuting Activities of Partially (1-4) β-Chlorinated Derivatives of Manganese(III) meso-Tetrakis(N-ethylpyridinium-2-yl)porphyrin" Inorganic Chemistry, 38(2):391-396 (1999).
Keil, K. P. et al. "Influence of animal husbandry practices on void spot assay outcomes in C57BL/6J male mice" Neurourology and Urodynamics, 35(2):192-198 (2014).
Keir, S.T. et al. "Cellular Redox Modulator, ortho Mn(III) meso-tetrakis(N-n-Hexylpyridinium-2-yl)porphyrin, MnTnHex-2-PyP5+ in the Treatment of Brain Tumors" Anticancer Agents in Medicinal Chemistry, 11(2):202-212 (2011).
Kimura, M. et al. "Pilot Study Evaluating a Rat Model of Radiation-induced Erectile Dysfunction Using an Image-guided Microirradiator" Urology, 85(5):1214.e1-1214.e6 (2015).
Kimura, M. et al. "Radiation-induced erectile dysfunction using prostate-confined modern radiotherapy in a rat model" Journal of Sexual Medicine, 8(8):2215-2226 (2011).
Kimura, M. et al. "Role of Oxidative Stress in a Rat Model of Radiation-Induced Erectile Dysfunction" Journal of Sexual Medicine, 9(6):1535-1549 (2012).
Kirlin, W. G. et al. "Glutathione redox potential in response to differentiation and enzyme inducers" Free Radical Biology & Medicine, 27(11/12):1208-1218 (1999).
Kiselyov, A. S. "Chemistry of N-fluoropyridinium salts" Chemistry Society Reviews, 34(12):1031-1037 (2005).
Klotz, L. "Active surveillance for prostate cancer: trials and tribulations" World Journal of Urology, 26(5):437-442 (2008).
Kodell, R. L. et al. "Determination of Sample Sizes for Demonstrating Efficacy of Radiation Countermeasures" Biometrics, 66(1):239-248 (2010).
Koontz, B. F. et al. "Feasibility Study of an Intensity-Modulated Radiation Model for Study of Erectile Dysfunction" Journal of Sexual Medicine, 8(2):411-418 (2011).
Koontz, B. F. et al. "Impact of Primary Gleason Grade on Risk Stratification for Gleason Score 7 Prostate Cancers" International Journal of Radiation, Oncology, Biology, Physics, 82(1):200-203 (2012).
Koontz, B. F. et al. "Phase 1 trial of neoadjuvant radiation therapy before prostatectomy for high-risk prostate cancer" International Journal of Radiation Oncology, Biology, Physics, 87(1):88-93 (2013).
Kos, I. et al. "Lipophilicity of potent porphyrin-based antioxidants: Comparison of ortho and meta isomers of Mn(III) N-alkylpyridylporphyrins" Free Radical Biology and Medicine, 47(1):72-78 (2009).
Leu, D. et al. "CNS bioavailability and radiation protection of normal hippocampal neurogenesis by a lipophilic Mn porphyrin-based superoxide dismutase mimic, MnTnBuOE-2-PyP5+" Redox Biology, 12(C):864-871 (2017).
Li, C. Y. et al. "Initial Stages of Tumor Cell-Induced Angiogenesis: Evaluation via Skin Window Chambers in Rodent Models" Journal of the National Cancer Institute, 92(2):143-147 (2000).
Liang, T. et al. "Introduction of Fluorine and Fluorine-Containing Functional Groups" Angewandte Chemie International Edition, 52(32):8214-8264 (2013).
Lien, Y-C. et al. "Phospholipase C-δ1 Is a Critical Target for Tumor Necrosis Factor Receptor-Mediated Protection against Adriamycin-Induced Cardiac Injury" Cancer Research, 66(8):4329-4338 (2006).

(56) References Cited

OTHER PUBLICATIONS

Lien, Y-C. et al. "TNF receptors deficiency exacerbated adriamycin-induced cardiomyocytes apoptosis: An Insight into Fas connection" Molecular Cancer Therapeutics, 5(2):261-269 (2006).
Lin, P. et al. "Antiangiogenic gene therapy targeting the endothelium-specific receptor tyrosine kinase Tie2" Proceedings of the National Academy of Sciences of the United States of America, 95(15):8829-8834 (1998).
Mackensen, G. B. et al. "Neuroprotection from Delayed Postischemic Administration of a Metalloporphyrin Catalytic Antioxidant" The Journal of Neuroscience, 21(13):4582-4592 (2001).
Mantz, C. A. et al. "Potency preservation following conformal radiotherapy for localized prostate cancer: impact of neoadjuvant androgen blockade, treatment technique, and patient-related factors" Cancer J Scientific American, 5(4):230-236 (1999) Abstract.
Manzoor, A. A. et al. "Overcoming Limitations in Nanoparticle Drug Delivery: Triggered, Intravascular Release to Improve Drug Penetration into Tumors" Cancer Research, 72(21):5566-5575 (2012).
McCullagh, P. et al. "Generalized Linear Models" Chapman and Hall/CRC, 2nd Edition, 526 pages (1989).
Meltzer, D. et al. "Patterns of Prostate Cancer Treatment by Clinical Stage and Age" American Journal of Public Health, 91(1):126-128 (2001).
Miriyala, S. et al. "Manganese superoxide dismutase, MnSOD and its mimics" Biochimica et Biophysica Acta, 1822(5):794-814 (2012).
Moeller, B. J. et al. "A manganese porphyrin superoxide dismutase mimetic enhances tumor radioresponsiveness" International Journal of Radiation, Oncology, Biology, Physics, 63(2):545-552 (2005).
Moser, J. C. et al. "Pharmacological ascorbate and ionizing radiation (IR) increase labile iron in pancreatic cancer" Redox Biology, 2:22-27 (2013).
Moul, J. W. "Prostate specific antigen only progression of prostate cancer" The Journal of Urology, 163(6):1632-1642 (2000).
Nam, R. K. et al. "Incidence of complications other than urinary incontinence or erectile dysfunction after radical prostatectomy or radiotherapy for prostate cancer: a population-based cohort study" The Lancet, Oncology, 15(2):223-231 (2014).
Needham D, et al. "A new temperature-sensitive liposome for use with mild hyperthermia: Characterization and testing in a human tumor xenograft model" Cancer Research, 60(5):1197-1201 (2000).
Oberley-Deegan, R. E. et al. "Mechanisms by Which Manganese Porphyrins Affect Signaling in Cancer Cells" Redox-Active Therapeutics, Springer US, pp. 405-431 (2015).
Oberley-Deegan, R. E. et al. "The Antioxidant, MnTE-2-PyP, Prevents Side-Effects Incurred by Prostate Cancer Irradiation" PLoS One, 7(9):e44178 (2012).
Ohebshalom, M. et al. "The efficacy of sildenafil citrate following radiation therapy for prostate cancer: temporal considerations" Journal of Urology, 174(1):258-262 (2005).
Oscarsson, N. et al. "Hyperbaric Oxygen Treatment in Radiation-Induced Cystitis and Proctitis: A Prospective Cohort Study on Patient-Perceived Quality of Recovery" International Journal of Radiation, Oncology, Biology, Physics, 87(4):670-675 (2013).
Pfitzenmaier, J. et al. "Characterization of C4-2 Prostate Cancer Bone Metastases and Their Response to Castration" Journal of Bone and Mineral Research, 18(10):1882-1888 (2003).
Pisansky, T. M. et al. "Tadalafil for Prevention of Erectile Dysfunction After Radiotherapy for Prostate Cancer The Radiation Therapy Oncology Group [0831] Randomized Clinical Trial" JAMA, 311(13):1300-1307 (2014).
Pollard, J. M. et al. "Radioprotective effects of manganese-containing superoxide dismutase mimics on ataxia-telangiectasia cells" Free Radical Biology and Medicine, 47(3):250-260 (2009).
Rajic, Z. et al. "Challenges encountered during development of Mn porphyrin-based, potent redox-active drug and superoxide dismutase mimic, MnTnBuOE-2-PyP5+, and its alkoxyalkyl analogues" Journal of Inorganic Biochemistry, 169:50-60 (2017).
Ramachandran, P. V. "Welcome to 'fluorine in medicinal chemistry'" Future Medicinal Chemistry, 1(5):771-772 (2009).

Rebouças, J. S. et al. "Redox modulation of oxidative stress by Mn porphyrin-based therapeutics: the effect of charge distribution" Dalton Transactions 9:1233-1242 (2008).
Rebouças, J. S. et al. "Impact of electrostatics in redox modulation of oxidative stress by Mn porphyrins: protection of SOD-deficient *Escherichia coli* via alternative mechanism where Mn porphyrin acts as a Mn carrier" Free Radical Biology and Medicine, 45:201-210 (2008).
Safford, S. E. et al. "Suppression of Fibrosarcoma Metastasis by Elevated Expression of Manganese Superoxide Dismutase" Cancer Research, 54(16):4261-4265 (1994).
Sato, T. et al. "Treatment of Irradiated Mice with High-Dose Ascorbic Acid Reduced Lethality" PLoS One 10(2): e0117020 (2015).
Shah, P. et al. "The role of fluorine in medicinal chemistry" Journal of Enzyme Inhibition and Medicinal Chemistry, 22(5):527-540 (2007).
Shappley, W. V. et al. "Prospective Study of Determinants and Outcomes of Deferred Treatment or Watchful Waiting Among Men With Prostate Cancer in a Nationwide Cohort" Journal of Clinical Oncology, 27(30):4980-4985 (2009).
Siglin, J. et al. "Time of decline in sexual function after external beam radiotherapy for prostate cancer" International Journal of Radiation, Oncology, Biology, Physics, 76(1):31-35 (2010).
Singer, P. A. et al. "Sex or survival: trade-offs between quality and quantity of life" Journal Clinical Oncology, 9(2):328-334 (1991) (Abstract).
Sonveaux, P. et al. "Targeting lactate-fueled respiration selectively kills hypoxic tumor cells in mice" The Journal of Clinical Investigation, 118(12):3930-3942 (2008).
Spasojevic, I. et al. "Bioavailability of metalloporphyrin-based SOD mimics is greatly influenced by a single charge residing on a Mn site" Free Radical Research, 45(2):188-200 (2011).
Spasojevic, I. et al. "Electrostatic Contribution in the Catalysis of O Dismutation by Superoxide Dismutase Mimics MnIIITE-2-PyP5+ VERSUSMnIIIBr8T-2-PyP+" Journal of Biological Chemistry, 278(9):6831-6837 (2003).
Spasojevic, I. et al. "Manganese(III) Complexes with Porphyrins and Related Compounds as Catalytic Scavengers of Superoxide" Inorganic Chimica Acta, 317(1-2):230-242 (2002).
Spasojevic, I. et al. "Mini Test Dose of Intravenous Busulfan (Busulfex®) in Allogeneic Non-Myeloablative Stem Cell Transplantation, Followed by Liquid Chromatography Tandem-Mass Spectrometry" Cancer Investigation, 30(9):679-682 (2012).
Spasojevic, I. et al. "Mn porphyrin-based superoxide dismutase (SOD) mimic, MnIIITE-2-PyP5+, targets mouse heart mitochondria" Free Radical Biology and Medicine, 42(8):1193-1200 (2007).
Spasojevic, I. et al. "Pharmacokinetics of the potent redox modulating manganese porphyrin, MnTE-2-PyP5+ in plasma and major organs of B6C3F1 mice" Free Radical Biology and Medicine, 45(7):943-949 (2008).
Spasojevic, I. et al. "Rotational Isomers of Nalkylpyridylporphyrins and their Metal Complexes. HPLC Separation, 1H NMR and X-ray Structural Characterization, Electrochemistry and Catalysis of O2.-Disproportionation" Inorgan Chem, 41(22):5874-5881 (2002).
Spasojevic, I., et al. "Nitrosylation of Manganese(II) tetrakis(Nethylpyridinium-2-yl)porphyrin: A Simple and Sensitive Spectrophotometric Assay for Nitric Oxide" Nitric Oxide: Biology and Chemistry, 4(5):526-533 (2000).
St Clair, D. K. et al. "Suppression of radiation-induced neoplastic transformation by overexpression of mitochondrial superoxide dismutase" Molecular Carcinogenesis, 6(4):238-242 (1992).
Sun, Y. et al. "A NADPH Oxidase-Dependent Redox Signaling Pathway Mediates the Selective Radiosensitization Effect of Parthenolide in Prostate Cancer Cells" Cancer Research, 70(7):2880-2890 (2010).
Symon, Z. et al. "A Murine Model for the Study of Molecular Pathogenesis of Radiation Proctitis" International Journal of Radiation, Oncology, Biology, Physics, 76(1):242-250 (2010).
Tovmasyan, A. et al. "A comprehensive evaluation of catalase-like activity of different classes of redox-active therapeutics" Free Radical Biology and Medicine, 86:308-321 (2015).
Tovmasyan, A. et al. "Differential Coordination Demands in Fe versus Mn Water-Soluble Cationic Metalloporphyrins Translate into

(56) References Cited

OTHER PUBLICATIONS

Remarkably Different Aqueous Redox Chemistry and Biology" Inorganic Chemistry, 52(10):5677-5691 (2013).

Tovmasyan, A. et al. "Methoxy-derivatization of alkyl chains increases the in vivo efficacy of cationic Mn porphyrins. Synthesis, characterization, SOD-like activity, and SOD-deficient *E. coli* study of meta Mn(III) N-methoxyalkylpyridylporphyrins" Dalton Transactions, 40:4111-4121 (2011).

Tovmasyan, A. et al. "Mn porphyrin-based SOD mimic and vitamin C enhance radiation-induced tumor growth inhibition" Free Radical Biology and Medicine, 87(S97) (2015).

Tovmasyan, A. et al. "Novel fluorinated Mn porphyrin as powerful SOD mimic and catalyst for ascorbate-coupled anticancer therapy" Free Radical Biology and Medicine, 112(S1):36-37 (2017).

Tovmasyan, A. et al. "Protection of rat prostate and erectile function from radiation-induced damage by novel Mn(III) N-substituted pyridylporphyrin and ascorbate" Free Radical Biology and Medicine, 112:35-36 (2017).

Tovmasyan, A. et al. "PSS307—We have come a long way with Mn porphyrins: from superoxide dismutation to H2O2-driven pathways" Free Radical Biology and Medicine, 65:S133 (2013).

Tovmasyan, A. et al. "Rational Design of Superoxide Dismutase (SOD) Mimics: The Evaluation of the Therapeutic Potential of New Cationic Mn Porphyrins with Linear and Cyclic Substituents" Inorganic Chemistry, 53:11467-11483 (2014).

Tovmasyan, A. et al. "Simple Biological Systems for Assessing the Activity of Superoxide Dismutase Mimics" Antioxidants & Redox Signaling, 20(15):2416-2436 (2014).

Umemoto et al. "Synthesis of 2,2,2-Trifluoroethylated Onium Salts of Nitrogen, Sulfur, and Phosphorus with (2,2,2-Trifluoroethyl)phenyliodonium Triflate" Bulletin of the Chemical Society of Japan, 64(6):2008-2010 (1991).

Umemoto et al. "Synthesis, Properties, and Reactivity of (1H,1H-Perfluoroalkyl)- and (1H-Perfluoro-1-alkenyl) aryliodonium Triflates and Their Analogs" Bulletin of the Chemical Society of Japan, 60(9):3307-3313 (1987).

Umemoto et al., "1,1-dihydroperfluoroalkylations of nucleophiles with (1,1-dihydroperfluoroalkyl)phenyliodonium triflates" Journal of Fluorine Chemistry, 31(2):231-236 (1986).

Urano M. et al. "Expression of manganese superoxide dismutase reduces tumor control radiation dose: Gene-Radiotherapy" Cancer Research, 55:2490-2493 (1995).

Wagner et al. "Biohalogenation: Nature's Way to Synthesize Halogenated Metabolites" Journal of Natural Products, 72:540-553 (2009).

Welsh, J. J. et al. "Ascorbate is a radiosensitizer in pancreatic cancer" Free Radical Biology and Medicine, 53:S52 (2012).

Wong, A. L. et al. "Tie2 expression and phosphorylation in angiogenic and quiescent adult tissues" Circulation Research, 81(4):567-574 (1997).

Xu, Y. et al. "KEAP1 Is a Redox Sensitive Target That Arbitrates the Opposing Radiosensitive Effects of Parthenolide in Normal and Cancer Cells" Cancer Research, 73(14):4406-4417 (2013).

Xu, Y. et al. "RelB Enhances Prostate Cancer Growth: Implications for the Role of the Nuclear Factor-kB Alternative Pathway in Tumorigenicity" Cancer Research, 69(8):3267-3271 (2009).

Yang, W. et al. "Redox regulation of cancer metastasis: molecular signaling and therapeutic opportunities" Drug Development Research, 75(5):331-341 (2014).

Yao, P. et al. "Quercetin protects human hepatocytes from ethanol-derived oxidative stress by inducing heme oxygenase-1 via the MAPK/Nrf2 pathways" Journal of Hepatology, 47(2):253-261 (2007).

Ye, X. et al. "Cytotoxic effects of Mn(III) N-alkylpyridylporphyrins in the presence of cellular reductant, ascorbate" Free Radical Research, 45(11-12):1289-1306 (2011).

Yen, H. C. et al. "The protective role of manganese superoxide dismutase against adriamycin-induced acute cardiac toxicity in transgenic mice" The Journal of Clinical Investigation, 98(5):1253-1260 (1996).

Yulyana, Y. et al. "Redox-Active Mn Porphyrin-based Potent SOD Mimic, MnTnBuOE-2-PyP5+, Enhances Carbenoxolone-Mediated TRAIL-lnduced Apoptosis in Glioblastoma Multiforme" Stem Cell Reviews and Reports, 12:140-155 (2016).

Zagar, T. M. et al. "Two phase I dose-escalation/pharmacokinetics studies of low temperature liposomal doxorubicin (LTLD) and mild local hyperthermia in heavily pretreated patients with local regionally recurrent breast cancer" Int J Hyper, 30:285-94(2014).

Zhao, Y. et al. "Manganese superoxide dismutase deficiency enhances cell turnover via tumor promoter-induced alteration in AP-1 and p53-mediated pathways in a skin cancer model" Oncogene, 21(24):3836-3846 (2002).

Zhao, Y. et al. "Overexpression of manganese superoxide dismutase suppresses tumor formation by modulation of activator protein-1 signaling in a multistage skin carcinogenesis model" Cancer Research, 61(16):6082-6088 (2001).

Zhao, Y. et al. "p53 Translocation to Mitochondria Precedes Its Nuclear Translocation and Targets Mitochondrial Oxidative Defense Protein-Manganese Superoxide Dismutase" Cancer Research, 65(9):3745-3750 (2005).

Zhao, Y. et al. "Redox Proteomic identification of HNE-bound mitochondrial proteins in cardiac tissues reveals a systemic effect on energy metabolism after Doxorubicin treatment" Free Radical Biology and Medicine, 72:55-65 (2014).

Boss , et al., ""Potential for a novel manganese porphyrin compound as adjuvant canine lymphoma therapy" Cancer Chemotherapy and Pharmacology, 80(2):421-431 (2017)".

\* cited by examiner

METHODS, COMPOSITIONS, AND KITS FOR TREATING AND/OR PREVENTING A SIDE EFFECT ASSOCIATED WITH RADIATION AND/OR CHEMOTHERAPY EXPOSURE

RELATED APPLICATION INFORMATION

This application claims the benefit of and priority to U.S. Provisional Patent Application Ser. No. 62/481,460, filed Apr. 4, 2017, the disclosure of which is incorporated herein by reference in its entirety.

STATEMENT OF GOVERNMENT SUPPORT

This invention was made with government support under contract number HHSN261201500002C awarded by the National Institutes of Health and grant number NIH 1R4CA195749 awarded by the National Institutes of Health. The government has certain rights in the invention.

FIELD OF THE INVENTION

The present invention concerns methods, compositions, and kits for treating and/or preventing one or more side effects associated with radiation and/or chemotherapy exposure in a subject, including methods, compositions and kits that include an active agent at a low dose.

BACKGROUND OF THE INVENTION

Each year more than 500,000 cancer patients in the United States are eligible for radiation therapy (with or without adjuvant therapy) with the intent to cure disease, extend life, and/or improve quality of life. When radiation therapy is employed, serious side effects can occur. The side effects can be a consequence of tissue damage and repair processes, such as development of scar tissue. For example, radiation therapy (RT) with curative intent is an important treatment modality for patients with cancer, such as, for example, head and neck squamous cell carcinomas (HNSCC). Although RT is generally effective for HNSCC, >90% of patients develop side effects as a result of their treatment, including dermatitis, xerostomia (loss of saliva production), and oral mucositis (inflammation and ulceration of the oropharyngeal and/or esophageal mucosa). These side effects are classified as "severe" in at least two-thirds of RT-treated HNSCC patients. Mucositis and xerostomia develop in a sequential fashion on the order of days/weeks to months following initiation of RT and pose a particular risk because they can interfere with oral food intake and dramatically reduce patient quality of life. Patients treated for brain tumors, including high-grade glioma (HGG) and brain metastases (BM) from tumors at other anatomical sites may obtain a survival benefit from brain radiation with or without adjunct chemotherapy. These patients usually suffer from severe decline in cognitive or other brain functions, depending on the anatomical location of brain tissues destroyed, along with other side effects of chemotherapy, such as bone marrow suppression. There are no FDA approved therapies for the management of mucositis, cognitive damage, bone marrow suppression, and other sequellae of radiation or radiation-chemotherapy combinations. The only approved drug for treating xerostomia, amifostine, has its own adverse effects and provides incomplete protection. Consequently, the acute effects of RT result in unplanned treatment breaks in roughly 30% of RT courses for HNSCC and a similar or larger fraction of patients with HGG and BM.

SUMMARY OF THE INVENTION

One aspect of the present invention is directed to a method of treating and/or preventing one or more side effects associated with radiation and/or chemotherapy exposure in a subject during and/or following radiation and/or chemotherapy exposure, the method comprising: administering to the subject prior to, during, or after radiation and/or chemotherapy exposure an active agent at a loading dose in an amount of about 0.05 mg/kg to about 1 mg/kg times the activity equivalent of BMX-001 (i.e., butoxyethyl pyridyl porphyrin); wherein the active agent is a meso-substituted metalloporphyrin. In some embodiments, tissue damage is treated and/or prevented in the subject.

Another aspect of the present invention is a method of treating and/or preventing one or more side effects associated with radiation and/or chemotherapy exposure in a subject during and/or following radiation and/or chemotherapy exposure, the method comprising: administering to the subject prior to, during, or after radiation and/or chemotherapy exposure an active agent at a loading dose in an amount of about 0.05 mg/kg to about 1 mg/kg; wherein the active agent has the structure:

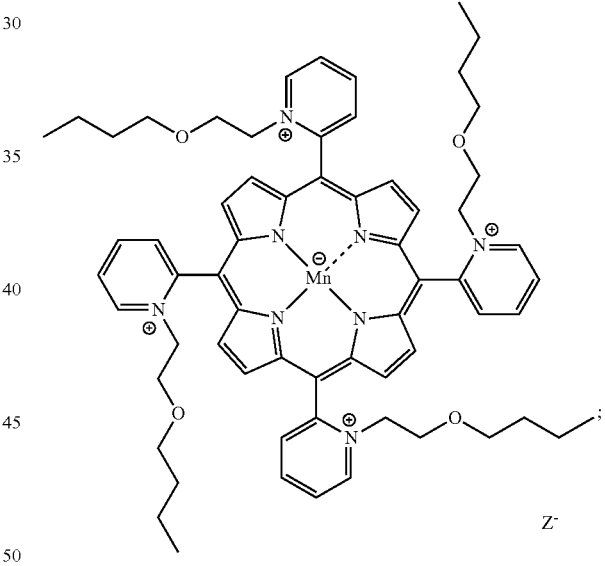

wherein Z⁻ is a counterion. In some embodiments, tissue damage is treated and/or prevented in the subject.

Another aspect of the present invention is directed to a kit comprising two or more pharmaceutically acceptable compositions, wherein each of the two or more pharmaceutically acceptable compositions comprise an active agent in an amount of about 10 to 20 mg active agent per mL of the composition, wherein the active agent is a meso-substituted metalloporphyrin.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
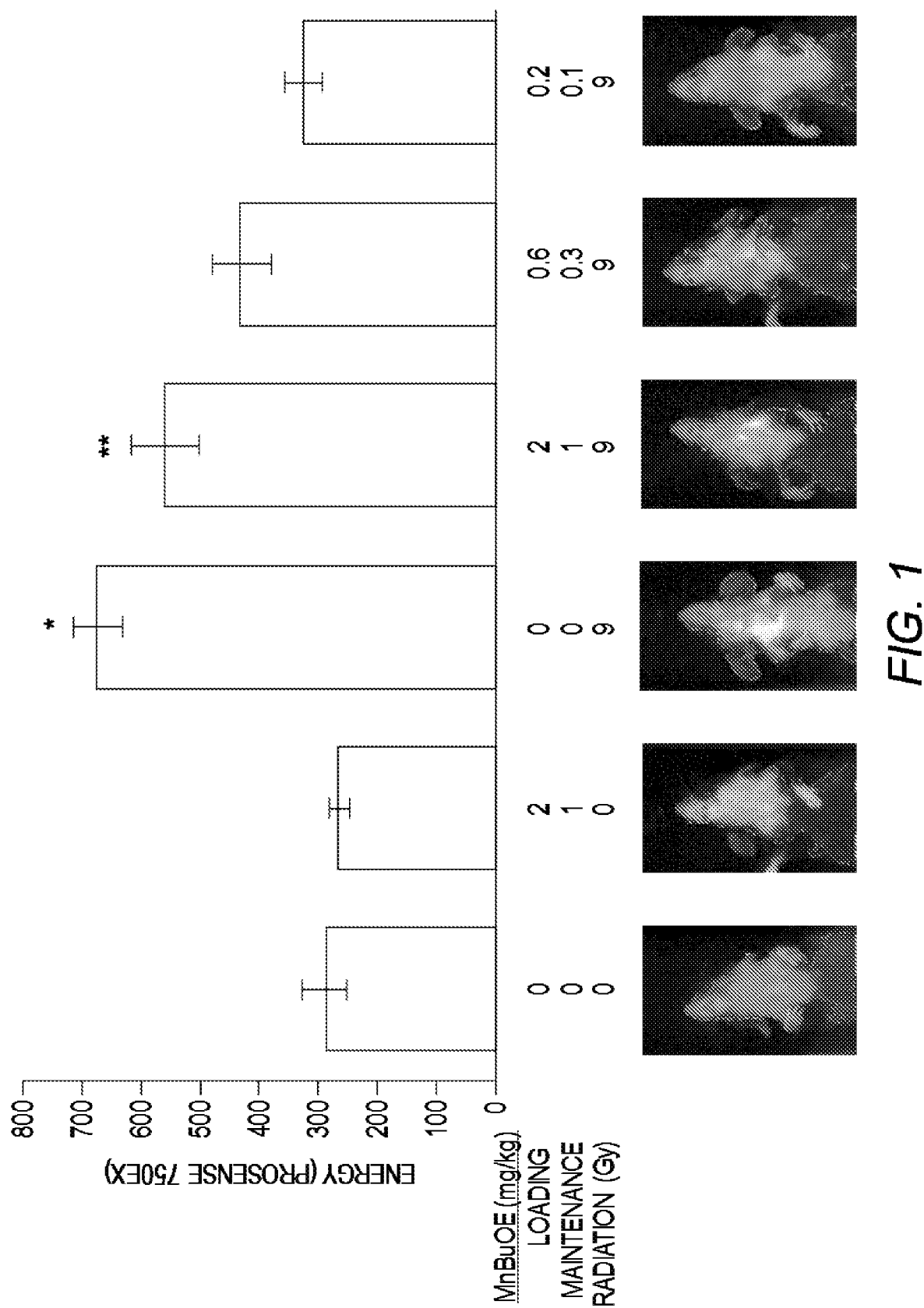
FIG. 1 shows the mucositis signal on day 11 post-RT. Inflammatory tissue was identified using ProSense 750EX, which is cleaved to become activated in the presence of cathepsins to yield a near infrared signal. Treatment with 9 Gy significantly increased in NIR signal in mice treated with both saline and 2/1 mg/kg MnBuOE. NIR signal was decreased in mice treated with either 0.6/0.3 mg/kg or 0.2/0.1 mg/kg MnBuOE. Representative FMT images are shown for all groups. N=4-6 mice/group. Data is reported as mean with SEM. * Significant difference (p<0.05) vs. saline/0 Gy control ** Significant difference (p<0.05) vs 2/1 mg/kg MnBuOE/0 Gy control.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even 0.1% of X. A range provided herein for a measureable value may include any other range and/or individual value therein.

"Pharmaceutically acceptable" as used herein means that the compound, anion, or composition is suitable for administration to a subject to achieve the treatments described herein, without unduly deleterious side effects in light of the severity of the disease and necessity of the treatment.

As used herein, the terms "increase," "increases," "increased," "increasing", "improve", "enhance", and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction", "inhibit", and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Alkyl" as used herein alone or as part of another group, refers to a straight or branched chain saturated hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 20 carbon atoms (or in lower alkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 20 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. In some embodiments, cycloalkyl refers to only a saturated cyclic hydrocarbon group containing from 3, 4 or 5 to 6, 7 or 8 carbons (which carbons may be replaced in a heterocyclic group as discussed below). The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety or another group through an oxy group, —O—. Representative examples of alkoxy include, but are not limited to, methoxy, ethoxy, propoxy, 2-propoxy, butoxy, tert-butoxy, pentyloxy, hexyloxy and the like. "Alkoxyalkyl" as used herein alone or as part of another group, refers to an alkyl or loweralkyl group, as defined herein (and thus including substituted versions such as polyalkoxy), appended to another alkyl or loweralkyl group through an oxy group, —O—, such as, but not limited to, —CH$_2$CH$_2$CH$_2$CH$_2$CH$_2$CH$_3$.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

Unless indicated otherwise, nomenclature used to describe chemical groups or moieties as used herein follow the convention where, reading the name from left to right, the point of attachment is at the rest of the molecule at the right-hand side of the name. For example, the group "(C$_{1-3}$ alkoxy)C$_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "-," it will be understood that the attachment is read from left to right.

Unless otherwise stated, structures depicted herein are meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Provided according to embodiments of the present invention are methods of treating and/or preventing one or more side effects associated with radiation and/or chemotherapy exposure in a subject during and/or following radiation and/or chemotherapy exposure. In some embodiments, methods of treating and/or preventing tissue damage in a subject during and/or following radiation and/or chemotherapy exposure are provided. A method of the present invention may comprise administering to the subject prior to, during, or after radiation and/or chemotherapy exposure a meso-substituted metalloporphyrin at a loading dose in an amount of about 0.05 to about 1 mg of the meso-substituted metalloporphyrin per kg of the subject times the activity equivalent of BMX-001. BMX-001, also known as manganese butoxyethyl pyridyl porphyrin or MnTnBuOE-2-PyP$^{5+}$, has the following structure:

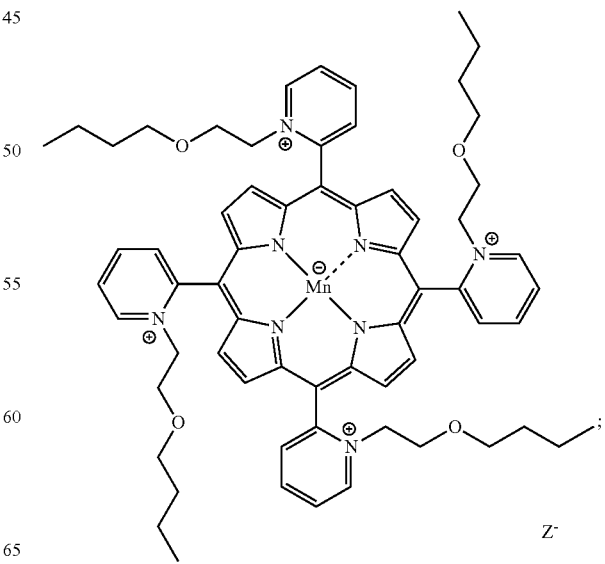

wherein $Z^-$ is a counterion. Example counterions include, but are not limited to, anions, such as, e.g., a halogen ion (e.g., chloride, etc.), $PF_6$, tosylate, besylate, and/or mesylate.

When referring to the activity equivalent of BMX-001, activity equivalent is determined according to methods known to those of skill, such as, but not limited to, determined using a cytochrome c assay and/or pulse radiolysis (Spasojevic, Ivan, et al., *Inorganic Chemistry*, Vol. 40, No. 4, 2001, 726-739). When the meso-substituted metalloporphyrin is BMX-001 the loading dose may be administered to the subject in an amount of about 0.05 to about 1 mg of BMX-001 per kg of the subject. Accordingly, the activity equivalent of BMX-001 is 1 when the meso-substituted metalloporphyrin is BMX-001. Alternatively, when a meso-substituted metalloporphyrin is 20% less active than BMX-001, the activity equivalent of BMX-001 is 1.25, so the dosage may be determined by taking 0.05 times 1.25 and 1 mg times 1.25 to get the loading dose range (e.g., about 0.0625 to about 1.25 mg of the meso-substituted metalloporphyrin per kg of the subject).

The inventors of the present invention surprisingly discovered that a low dose of a meso-substituted metalloporphyrin (e.g., BMX-001) can treat and/or prevent one or more side effects associated with radiation and/or chemotherapy exposure, such as, but not limited to, tissue damage, in a subject during and/or following radiation and/or chemotherapy exposure, such as, for example, in a subject being administered and/or undergoing radiation therapy and/or chemotherapy treatment. A treatment regimen of the present invention administers a low dose of a meso-substituted metalloporphyrin (e.g., BMX-001) and can treat and/or prevent one or more side effects associated with radiation and/or chemotherapy exposure in a subject during and/or following radiation and/or chemotherapy exposure, which was unexpected. In some embodiments, the low dose of the meso-substituted metalloporphyrin is nontoxic to noncancerous cells. Toxicity may be determined using methods known to those of skill. In some embodiments, a method, dosage, and/or treatment regimen of the present invention is nontoxic to noncancerous cells and/or a subject administered the meso-substituted metalloporphyrin, such as, for example, does not cause side effects such as, but not limited to, hypotension, hypotonia, distress, shaking, skin lesions, local necrosis, alopecia, weight loss, and/or pathological changes in one or more organ(s). In some embodiments, a method, dosage, and/or treatment regimen of the present invention is nontoxic to noncancerous cells and/or a subject administered the meso-substituted metalloporphyrin with a large margin of safety or separation between toxic and nontoxic doses of the meso-substituted metalloporphyrin, such as, for example, a nontoxic dose is at least about 5×, 10×, 20×, 30×, 40×, or 50× less than a toxic dose.

The meso-substituted metalloporphyrin administered in a method of the present invention may be a superoxide dismutase (SOD) mimetic, and since superoxide dismutase (SOD) enzymes are prevalent in mammals (e.g., humans) one would have expected that higher doses of meso-substituted metalloporphyrins would be needed in order to obtain prophylactic and/or therapeutic effects compared to the lower doses administered in a method of the present invention. The substantial concentration of enzymatic and non-enzymatic antioxidants in normal tissues, which includes superoxide dismutases, catalases, peroxidases, thioredoxins, peroxiredoxins, and multiple nonenzymatic antioxidants, suggests that high concentrations of a redox-active pharmaceutical (e.g., a meso-substituted metalloporphyrin) would be required in order to have a significant biological effect in tissues. The concentration of a redox-active metalloporphyrin previously found to be effective as a radioprotectant in multiple animal studies has been on the order of 3-5 mg/kg per day or 21-35 mg/kg per week, with the expectation that the optimum effective dose would be close to the maximum tolerated dose. The findings of the present invention include that lower doses than those expected (e.g., a dose as low as 0.3-0.4 mg/kg/week) can be beneficial (e.g., provide a high level of protection against radiation-induced injury) without toxicity, which was unexpected based on existing literature and knowledge of the distribution and concentrations of endogenous antioxidant defenses.

A compound of the present invention may be administered in combination with one or more therapies. "Combination" as used herein with respect to a method of administration (e.g., an active agent and a chemotherapeutic administered in combination) includes administering the two or more compounds simultaneously, or sequentially, sufficiently close in time to produce a combined therapeutic, prophylactic, or treatment effect. For example, in some embodiments, a meso-substituted metalloporphyrin and radiation therapy are administered in combination, optionally in combination with one or more adjuvant therapies, such as, e.g., chemotherapy. In some embodiments, a meso-substituted metalloporphyrin and chemotherapy are administered in combination, optionally in combination with one or more adjuvant therapies, such as, e.g., chemotherapy.

In some embodiments, a method of the present invention may treat and/or prevent one or more side effects associated with radiation and/or chemotherapy exposure in a subject during and/or following radiation and/or chemotherapy exposure. For example, in some embodiments, a method of present invention may be used in combination with radiation therapy and/or chemotherapy. In some embodiments, the loading dose may be administered to a subject prior to beginning radiation therapy and/or chemotherapy. Alternatively, the loading dose may be administered to a subject after radiation and/or chemotherapy exposure, e.g., after at least one radiation therapy and/or chemotherapy treatment. In some embodiments, the loading dose may be administered to a subject after radiation exposure, such as, e.g., exposure to a radioactive element (e.g., americium, curium, plutonium, etc.).

In some embodiments, the loading dose may be administered to the subject at about 30 minutes to about 4 days prior to the subject being exposed to radiation and/or chemotherapy, such as, for example, about 1 hour to about 3 days, about 4 hours to about 2 days, or about 12 hours to about 48 hours prior to the subject being exposed to radiation and/or chemotherapy. In some embodiments, the loading dose may be administered to the subject at about 30, 45, or 60 minutes, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours prior to the subject being exposed to radiation and/or chemotherapy.

In some embodiments, the loading dose may be administered to the subject at about 30 minutes to about 4 days after the subject is exposed to radiation and/or chemotherapy, such as, for example, about 1 hour to about 3 days, about 4 hours to about 2 days, or about 12 hours to about 48 hours after exposure to radiation and/or chemotherapy. In some embodiments, the loading dose may be administered to the subject at about 30, 45, or 60 minutes, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after exposure to radiation and/or chemotherapy.

In a method of the present invention, a loading dose may be the first dosage of the active agent (i.e., a meso-substituted metalloporphyrin). The loading dose may be used to bring levels (e.g., plasma levels) of the active agent and/or derivatives thereof to a certain amount in the subject. In some embodiments, the loading dose is only administered one time as the initial dose.

In some embodiments, the loading dose may be administered to the subject in an amount of about 0.05 to about 1 mg of the meso-substituted metalloporphyrin per kg of the subject times the activity equivalent of BMX-001, such as, for example, about 0.1 mg/kg to about 1 mg/kg, about 0.1 mg/kg to about 0.6 mg/kg, or about 0.1 mg/kg to about 0.6 mg/kg times the activity equivalent of BMX-001. In some embodiments, the loading dose may be administered to the subject in an amount of about 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.1 mg of the meso-substituted metalloporphyrin per kg of the subject times the activity equivalent of BMX-001.

In some embodiments, administration of the loading dose to the subject may comprise administering to the subject about 5 mg to about 50 mg or about 7 mg to about 42 mg of the meso-substituted metalloporphyrin. For example, in administering the loading dose, the subject may be administered about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg of the meso-substituted metalloporphyrin.

A method of the present invention may further comprise administering to the subject the meso-substituted metalloporphyrin at a maintenance dose in an amount that is about 25% to about 75% less than the amount of the meso-substituted metalloporphyrin in the loading dose. In some embodiments, the maintenance dose provides the meso-substituted metalloporphyrin in an amount that is about 25%, 30%, 35%, 40%, 45%, 50%, 55%, 60%, 65%, 70%, or 75% less than the amount of the meso-substituted metalloporphyrin in the loading dose. In some embodiments, the maintenance dose comprises the meso-substituted metalloporphyrin in an amount that is about 50% less than the amount of the meso-substituted metalloporphyrin in the loading dose.

In some embodiments, administration of the maintenance dose to the subject may comprise administering to the subject about 5 to about 50 mg of the meso-substituted metalloporphyrin per week times the activity equivalent of BMX-001, such as, e.g., about 7 mg/week to about 40 mg/week. For example, in administering the maintenance dose, the subject may be administered about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg of the meso-substituted metalloporphyrin per week times the activity equivalent of BMX-001.

The maintenance dose may be administered one or more times per week (e.g., 1, 2, 3, 4, 5, or more times per week). In some embodiments, the maintenance dose may be administered to the subject two or three times per week or every two or three days. In some embodiments, the maintenance dose may be administered two or three times a week or every two or three days after an initial radiation and/or chemotherapy exposure (e.g., an initial radiation and/or chemotherapy treatment).

The maintenance dose may be administered one or more times after an initial radiation and/or chemotherapy exposure (e.g., an initial radiation and/or chemotherapy treatment), such as, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times. In some embodiments, the subject is receiving radiation therapy and/or chemotherapy and the maintenance dose is administered throughout the course of the radiation therapy and/or chemotherapy, such as, for example, one or more times during the course of the radiation therapy and/or chemotherapy.

In some embodiments, the maintenance dose may be administered one or more times after a final radiation and/or chemotherapy exposure (e.g., a final radiation and/or chemotherapy treatment), such as, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times. In some embodiments, the subject has received a final radiation therapy and/or chemotherapy treatment and the maintenance dose is administered one or more times following the final radiation therapy and/or chemotherapy treatment. In some embodiments, the maintenance dose is administered two or three times a week or every two or three days for 1 to 8 weeks after a final radiation and/or chemotherapy exposure (e.g., a final radiation and/or chemotherapy treatment).

According to some embodiments of the present invention, the subject may be exposed to radiation, such as, e.g., the subject may receive a total dose of radiation of about 5 to about 100 Gy or about 30 to about 90 Gy. In some embodiments, the subject may be exposed to a total dose of radiation of about 5, 10, 15, 20, 25, 30, 35, 40, 45, 50, 55, 60, 65, 70, 75, 80, 85, 90, 95, 100, 125, 150 Gy or more. In some embodiments, the subject is receiving and/or may be administered radiation therapy. The radiation therapy may comprise at least one radiation treatment that is administered 5 days a week for 1 to 10 weeks. As one of ordinary skill in the art understands, radiation therapy may span a certain length of time (e.g., 1-10 weeks) and may not be administered to the subject continuously, but rather intermittently. In some embodiments, the maintenance dose may be administered during the same period of time that the subject is receiving radiation therapy. The maintenance dose may be administered on the same day as when the subject receives radiation therapy or a different day. In some embodiments, the maintenance dose may be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours before and/or after a radiation therapy treatment. In some embodiments, the maintenance dose may be administered while subject is receiving a radiation therapy treatment.

According to some embodiments of the present invention, the subject is receiving and/or may be administered chemotherapy. Example chemotherapies include, but are not limited to, cisplatin, temozolomide, tamoxifen, trastuzumab, fluorouracil (e.g., 5 fluorouracil (5FU)), mitomycin-C, and/or FOLFOX. The method and/or meso-substituted metalloporphyrin may not interfere with tumor control and/or cancer treatment (e.g., chemotherapy). As one of ordinary skill in the art understands, chemotherapy may span a certain length of time (e.g., 1-10 weeks) and may not be administered to the subject continuously, but rather intermittently. In some embodiments, the maintenance dose may be administered during the same period of time that the subject is receiving chemotherapy. The maintenance dose may be administered on the same day as when the subject receives chemotherapy or a different day. In some embodiments, the maintenance dose may be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours before and/or after a chemotherapy treatment. In some embodiments, the maintenance dose may be administered while subject is receiving a chemotherapy treatment.

In some embodiments, the subject is receiving and/or may be administered radiation therapy and an adjuvant therapy. Example adjuvant therapies include, but are not limited to, antibiotics, hormone therapy, chemotherapy, immunotherapy, and/or targeted therapy. In some embodiments, an adjuvant therapy may cause side effects associated with tissue damage and/or inflammation). The radiation therapy, adjuvant therapy, and meso-substituted metalloporphyrin may be administered to the subject during the same period of time (i.e., the therapies overlap), and may be administered on the same day or different days. In some embodiments, the radiation therapy and adjuvant therapy are administered to the subject so that they do not overlap. For example, the subject may be administered radiation therapy for a period of time and after completion of the radiation therapy the subject may be administered chemotherapy. In some embodiments, a method of the present invention does not compromise and/or interfere with radiation therapy and/or adjuvant therapy, such as, e.g., an adjuvant therapy that is co-administered to the subject with radiation therapy and the meso-substituted metalloporphyrin. In some embodiments, the subject is receiving radiation therapy and chemotherapy and the subject is administered the maintenance dose throughout radiation therapy and chemotherapy, and the maintenance dose is administered 1 to 8 weeks after a final chemotherapy treatment.

In some embodiments, a method of the present invention comprises administering a therapeutically effective amount of a meso-substituted metalloporphyrin to a subject. As used herein, the term "therapeutically effective amount" refers to an amount of a meso-substituted metalloporphyrin that elicits a therapeutically useful response in a subject. Those skilled in the art will appreciate that the therapeutic effects need not be complete or curative, as long as some benefit is provided to the subject.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with a radiation and/or chemotherapy exposure is achieved and/or there is a delay in the progression of the symptom. In some embodiments, the severity of a symptom associated with a radiation and/or chemotherapy exposure may be reduced in a subject compared to the severity of the symptom in the absence of a method of the present invention.

In some embodiments, a meso-substituted metalloporphyrin may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a symptom associated with a radiation and/or chemotherapy exposure and/or a reduction in the severity of the onset of symptom associated with a radiation and/or chemotherapy exposure relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention.

In some embodiments, a meso-substituted metalloporphyrin may be administered in a prevention effective amount. A "prevention effective" amount as used herein is an amount that is sufficient to prevent (as defined herein) a symptom associated with a radiation and/or chemotherapy exposure in a subject. Those skilled in the art will appreciate that the level of prevention need not be complete, as long as some benefit is provided to the subject. In some embodiments, a prevention effective amount may be achieved by administering a composition of the present invention.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

A method of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject has findings typically associated with cancer, is suspected to have cancer, and/or the subject has cancer.

A method of the present invention may treat and/or prevent in a subject one or more side effects associated with radiation exposure and/or an adjuvant therapy (e.g., chemotherapy) compared to a conventional treatment (e.g., a conventional radiation therapy and/or chemotherapy) and/or in the absence of a method of the present invention. An example conventional radiation therapy includes, but is not limited to, radiation therapy that is administered as fractionated focal irradiation in daily fractions of 1.8-2 Gy given 5 days a week for 6 weeks for a total of 5960 Gy. Example conventional chemotherapies include, but are not limited to, temozolomide that is administered during chemoradiation at a dose of 75 mg per square meter of body surface area per day for 7 days a week, starting from the first radiation therapy dose to the last, or for a total of 42 days, and temozolomide that is administered at a dose of 150 or 200 mg per square meter of body surface area per day for 5 consecutive days per 28-day treatment cycle. In some embodiments, the method may reduce (e.g., the degree or presence by at least about 5% or more) in the subject one or more side effects associated with radiation therapy and/or an adjuvant therapy. Example side effects include, but are not limited to, alopecia, dermatitis, fatigue, neurological symptoms, nausea, vomiting, otitis externa, seizures, thrombocytopenia, bone marrow suppression, mucositis, esophagitis, laryngeal dysfunctions (e.g., aspiration, hoarseness), fibrosis (e.g., bladder fibrosis), one or more symptom(s) associated with pelvic radiation syndrome, cognitive dysfunction, tissue damage, xerostomia, myelosuppression, hyperpigmentation, pneumonitis, pulmonary fibrosis, hot flashes, deep vein thrombosis, erectile dysfunction, urinary urgency/frequency, proctitis, fibrotic changes (e.g., fibrotic changes to urethra, colon, rectum, anus, skin, muscle, and/or connective tissue), incontinence, decreased libido, bicalutamide adverse effects (e.g., breast tenderness and gynecomastia), diarrhea, hepatotoxicity, skin breakdown, skin irritation, colicky abdominal pain, malabsorption leading to weight loss, steatorrhea, ileum damage, decreased bile acid resorption, leukopenia, thrombocytopenia, numbness/tingling, mouth sores, skin desquamation, proctitis, cystitis, and/or acute hematologic toxicities.

A method of the present invention may treat and/or prevent radiation-induced normal tissue injury in a subject. Radiation-induced normal tissue injury may be reduced in the subject by at least 5% or more compared to a conventional treatment and/or in the absence of a method of the present invention. "Normal tissue" as used herein refers to tissue that is noncancerous. The cells in "normal tissue" may be dividing at a normal rate. In some embodiments, the method may treat and/or prevent normal tissue injury due to and/or caused by inflammation. In some embodiments, the method may treat and/or prevent one or more side effects associated with radiation and/or chemotherapy exposure. For example, the method may treat and/or prevent dermatitis, mucositis, xerostomia, memory loss, cognitive decline, malaise, hair loss, bone marrow suppression, proctitis, cystitis, and/or fibrosis (including, e.g., excessive scarring, strictures, and/or replacement with scar tissue) in the subject. In some embodiments, a method of the present invention may provide radioprotection to hematopoietic stem cells and/or tissues (e.g., lung, and/or urogenital tissues including prostate, testes, penile tissue and its erectile function).

In some embodiments, a method of the present invention may provide a reduced decline in cognitive function compared to a conventional treatment and/or in the absence of a method of the present invention, when compared to cognitive function prior to a method of the present invention and chemotherapy and/or radiation therapy. A "cognitive function baseline" may be measured for a subject and is the subject's cognitive function prior to a method of the present invention and prior to administration of chemotherapy and/or radiation therapy. For example, prior to a method of the present invention and administration of chemotherapy and/or radiation therapy, a subject's cognitive function may be measured (i.e., the subject's cognitive function baseline) and subsequently compared to the subject's cognitive function after the radiation therapy and/or chemotherapy, and a method of the present invention may provide the subject with a reduced decline in cognitive function compared to a conventional treatment and/or in the absence of a method of the present invention. In some embodiments, a method of the present invention may provide a subject with a cognitive decline of about 30% or less (e.g., about 25%, 20%, 15%, 10%, 5%, 1%, or 0%) at about 1, 2, 3, 4, 5, 6, 7, 8, 9, 10, 11, 12, 13, 14, 15, 16, 17, 18, 19, or 20 weeks or more after the subject received the conventional radiation therapy and/or chemotherapy when compared to the subject's cognitive function baseline. In some embodiments, a method of the present invention provides a subject with no measurable decline in cognitive function at about 1, 2, 3, 4, 5, 6, 7, 8, 9, 10, 11, 12, 13, 14, 15, 16, 17, 18, 19, or 20 weeks or more after the subject received the conventional radiation therapy and/or chemotherapy when compared to the subject's cognitive function baseline. A subject's cognitive function may be measured using any suitable method known to those of skill in the art such as, e.g., Hopkins Verbal Learning Test-Revised (HVLT-R) and/or Trail Making B Test.

In some embodiments, a method of the present invention may provide decreased hair loss and/or enhanced hair growth compared to a conventional treatment and/or in the absence of a method of the present invention. For example, the method may provide no hair loss or decreased hair loss (e.g., about 10% or more) compared to a conventional treatment and/or in the absence of a method of the present invention. In some embodiments, a method of the present invention may provide increased hair growth (e.g., about 10% or more) compared to a conventional treatment and/or in the absence of a method of the present invention. In some embodiments, a method of the present invention may treat and/or protect oral mucosa and/or salivary gland function in a subject following the radiation therapy. In some embodiments, a method of the present invention may provide no increase or less than a 20% increase (e.g., less than 15%, 10%, 5%, or less) in leukocyte adhesion and/or rolling in post-capillary venules in a subject following the radiation and/or chemotherapy exposure compared to a conventional treatment and/or in the absence of a method of the present invention.

In some embodiments, a method of the present invention may protect against bone marrow suppression caused by chemotherapy and/or radiation therapy. In some embodiments, the method may protect against suppression of white cell count and/or protect against suppression of the platelet count. In some embodiments, the method may provide an increased (e.g., about 10% or more) white cell count and/or platelet count compared to a conventional treatment and/or in the absence of a method of the present invention. In some embodiments, the method may reduce the amount of bone marrow suppression caused by chemotherapy and/or radiation therapy. In some embodiments, a method of the present invention may protect and/or reduce thrombocytopenia in a subject, which may be related to treatment with temozolomide.

A method of the present invention may prevent thrombocytopenia in a subject and/or reduce the occurrence of thrombocytopenia in a subject compared to a conventional treatment and/or in the absence of a method of the present invention. In some embodiments, a method of the present invention may provide a subject with a platelet count of at least 100,000, 125,000, 150,000, 200,000, 250,000 or greater at about 1, 2, 3, 4, 5, 6, 7, 8, 9, 10, 11, 12, 13, 14, 15, 16, 17, 18, 19, or 20 weeks or more after the subject received conventional radiation therapy and/or chemotherapy. In some embodiments, a method of the present invention may provide a subject with a platelet count from 100,000 to 450,000 at about 1, 2, 3, 4, 5, 6, 7, 8, 9, 10, 11, 12, 13, 14, 15, 16, 17, 18, 19, or 20 weeks or more after the subject received conventional radiation therapy and/or chemotherapy. In some embodiments, a method of the present invention may provide a subject with a platelet count from 100,000 to 450,000 at about 1, 2, 3, 4, 5, 6, 7, 8, 9, 10, 11, 12, 13, 14, 15, 16, 17, 18, 19, or 20 weeks or more after the subject received conventional radiation therapy and/or temozolomide.

In some embodiments, a method of the present invention may decrease or inhibit tumor revascularization and/or growth in the subject. The method may decrease and/or inhibit tumor revascularization and/or growth in the subject by at least about 5%, 10%, 15%, 20%, 25%, 30%, 35%, 40%, 45%, 50%, 55%, 60%, 65%, 70%, 75%, 80%, 85%, 90%, 95%, or 100% compared to a conventional treatment and/or in the absence of a method of the present invention. A method and/or an active agent of the present invention may not protect a tumor and/or tumor cells and/or may not inhibit tumor cell death. In some embodiments, a method and/or active agent of the present invention may sensitize and/or increase the effectiveness of radiation therapy and/or chemotherapy (e.g., the active agent may be administered in an amount effect to radio- and/or chemosensitize a tumor and/or tumor cells).

A method of the present invention may treat and/or prevent long term effects and/or adverse side effects associated with radiation and/or chemotherapy exposure. In some embodiments, a method of the present invention may treat and/or prevent the amount of normal tissue injury in a subject and/or one or more side effects associated with radiation and/or chemotherapy exposure for a period of time after a final radiation and/or chemotherapy exposure and/or after the last maintenance dose. In some embodiments, the method may treat and/or prevent the degree and/or amount of one or more side effects associated with radiation and/or chemotherapy exposure (e.g., normal tissue injury) for about 1, 2, 3, or 4 weeks, or about 1, 2, 3, 4, 5, 6, 7, 8, 9, 10, 11, 12, 13, 14 months or more after a final radiation and/or chemotherapy exposure and/or after the last maintenance dose. For example, the method may reduce the amount of normal tissue injury for about 1-12 months following a final radiation therapy and/or chemotherapy treatment and/or a final maintenance dose. Thus, in some embodiments, a method of the present invention may treat and/or prevent one or more side effects associated with radiation and/or chemotherapy exposure in a subject after the last maintenance dose, and when the meso-substituted metalloporphyrin is no longer administered to the subject and/or after the half-life of the meso-substituted metalloporphyrin.

A method of the present invention may protect brain tissue in a subject during and/or after brain irradiation, such as, e.g., brain irradiation for metastases and/or prophylactic brain irradiation such as the prophylactic brain irradiation that is commonly done for treatment of lung cancer since brain is a primary site of metastases and the irradiation may be given to treat prevent the development of large brain metastases.

A subject of the present invention may have any type of cancer. In some embodiments, the subject has or is suspected to have cancer and the cancer is brain, head and neck (including vocal cords, larynx, pharynx, tongue, and/or salivary glands), breast, prostate, colon, rectum, renal, lymphoma (e.g., Hodgkin's or non-Hodgkin's lymphoma), leukemia, hepatic, stomach, esophagus, osteosarcoma, and/or anus cancer. In some embodiments, the subject has or is suspected to have a head and/or neck squamous cell carcinoma.

A method of the present invention may increase (e.g., by at least 10% or more) subject adherence to radiation therapy and/or an adjuvant therapy that is administered in combination to the subject compared to a conventional treatment and/or in the absence of a method of the present invention.

In some embodiments, a method of the present invention may increase the dosage of radiation administered to the subject in radiation therapy compared to a conventional radiation therapy dosage and/or may increase the dosage of chemotherapy administered to the subject in chemotherapy compared to a conventional chemotherapy dosage.

An active agent of the present invention may be administered to the subject in a pharmaceutically acceptable composition. In some embodiments, a pharmaceutically acceptable composition is in a form for subcutaneous administration. The pharmaceutically acceptable composition may be an injectable solution.

A meso-substituted metalloporphyrin used in a method of the present invention may be a superoxide dismutase (SOD) mimetic. In some embodiments, the meso-substituted metalloporphyrin is a compound of Formula I:

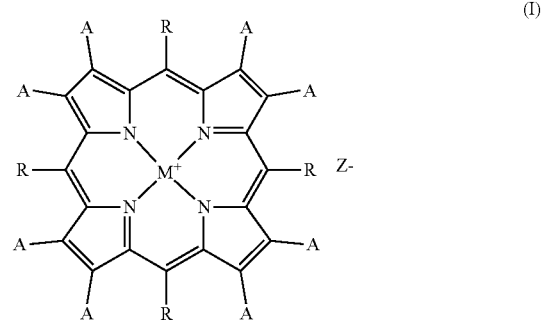

wherein:
    each R is an independently selected substituted or unsubstituted aryl, heteroaryl, cycloalkyl, or heterocycloalkyl;
    each A is an independently selected hydrogen, an electron-withdrawing group, or electron donating group (e.g., halogen, $NO_2$ or CHO);
    M is a metal; and
    Z– is a counterion;
    or a pharmaceutically acceptable salt thereof.

In some embodiments of Formula I, each R is heteroaryl or heterocycloalkyl, particularly those containing at least one or two nitrogen atoms in the heterocyclic ring (e.g., pyrrolyl, imidazolyl, triazolyl, pyridyl, pyrimidyl, triazinyl, oxazolyl, thiazolyl, oxazinyl, thiazinyl, oxathiazinyl, etc.), in some embodiments wherein at least one of which nitrogen atoms (or in some embodiments at least two of which nitrogen atoms) are optionally but preferably substituted (e.g., quaternized) with a substituent such as described in connection with heterocyclic groups above (e.g., substituted with alkyl, alkoxyalkyl, etc.). In some embodiments, R in a compound of Formula I is alkoxyalkylaryl or alkoxyalkylheteroaryl.

In some embodiments, the meso-substituted metalloporphyrin has a structure of Formula A1:

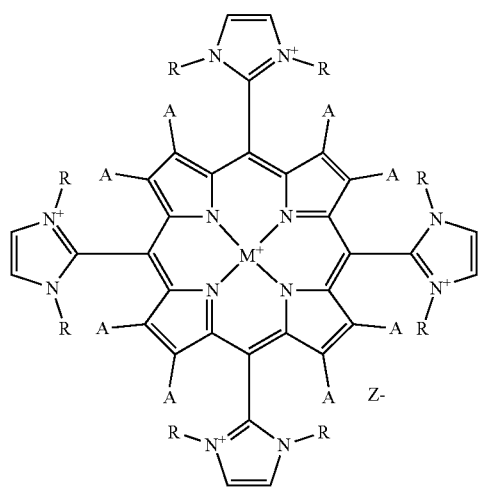

(A1)

wherein:

each R is an independently selected C1-12 alkyl or C1-C12 alkoxyalkyl;

each A is, independently, hydrogen or an electron withdrawing group (e.g., halogen, $NO_2$ or CHO);

M is metal selected from the group consisting of manganese, iron, copper, cobalt, and nickel; and Z– is a counterion.

In some embodiments, the meso-substituted metalloporphyrin has the formula:

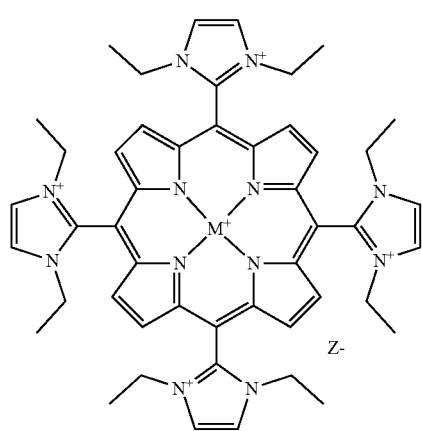

wherein Z– is a counterion.

In some embodiments, the meso-substituted metalloporphyrin has a structure of Formula B1:

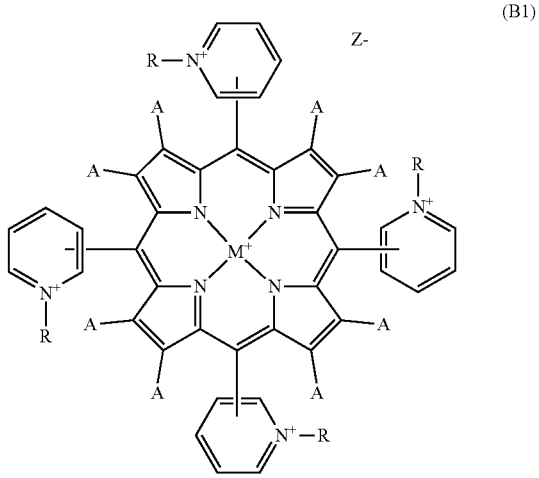

(B1)

wherein:

each R is an independently selected C1-12 alkyl or C1-12 alkyoxyalkyl;

each A is, independently, hydrogen or an electron withdrawing group (e.g., halogen, $NO_2$ or C(O)H);

M is metal selected from the group consisting of manganese, iron, copper, cobalt, and nickel, and Z– is a counterion.

In some embodiments, the meso-substituted metalloporphyrin has the structure:

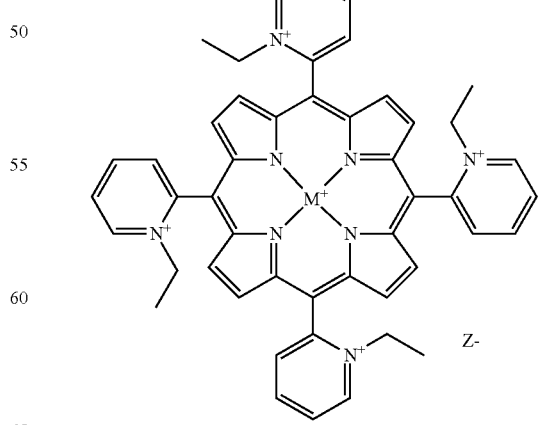

wherein $Z^-$ is a counterion.

In some embodiments, the meso-substituted metalloporphyrin has a structure of Formula C1:

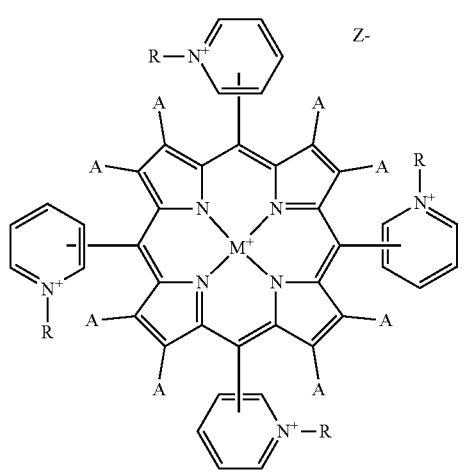

(C1)

wherein:

each R is an independently selected hydrogen or —(CH$_2$)$_m$CH$_2$OX;

m is 1 or 2;

X is C1-12 alkyl;

each A is, independently, hydrogen or an electron withdrawing group (e.g., halogen, NO$_2$ or CHO);

M is metal selected from the group consisting of manganese, iron, copper, cobalt, and nickel, and Z– is a counterion.

In some embodiments, X is a C4-C6 alkyl.

In some embodiments, the meso-substituted metalloporphyrin has the structure:

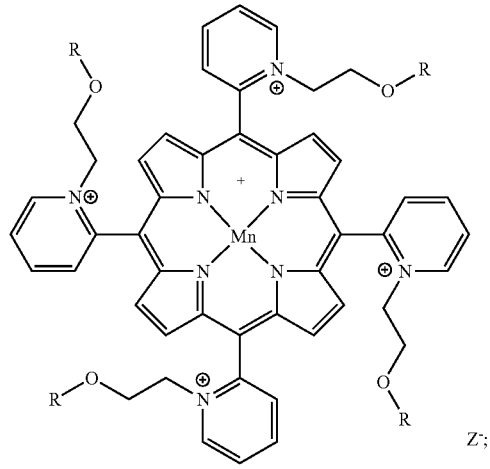

wherein each R is independently a C1-C12 alkyl and Z is an counterion (e.g., Cl, PF$_6$, tosylate, besylate, mesylate, etc.).

In some embodiments, the meso-substituted metalloporphyrin has the structure:

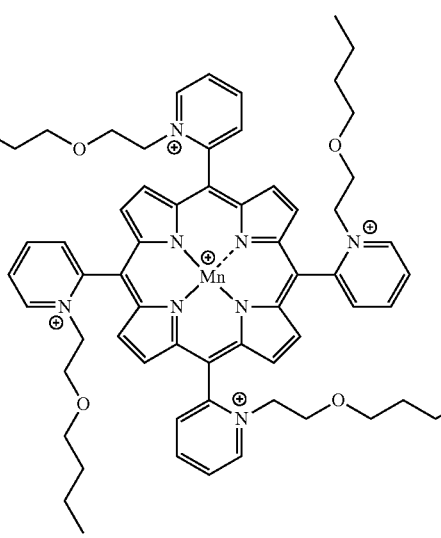

wherein Z$^-$ is a counterion.

In some embodiments, the meso-substituted metalloporphyrin has the structure:

wherein Z$^-$ is a counterion.

In some embodiments, a meso-substituted metalloporphyrin of the present invention does not include a compound having the structure:

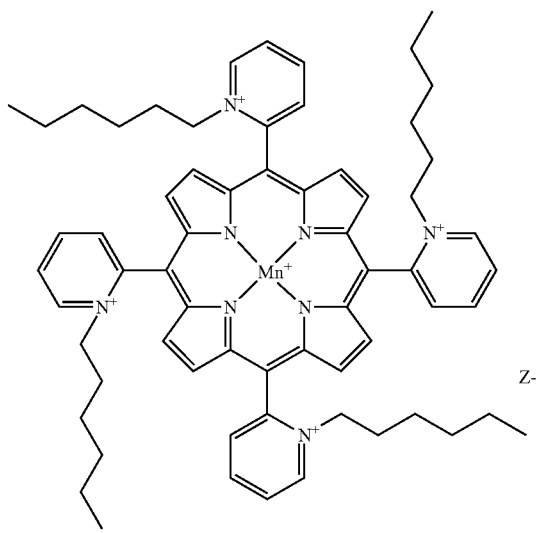

wherein Z⁻ is a counterion.

In some embodiments, all R groups in a compound described above are the same. In some embodiments, one or more (e.g., 1, 2, 3, or 4) R groups is hydrogen. In some embodiments, in a compound of Formula A1, B1, or C1, R is a C4-C12 alkyl (e.g., a C4, C5, C6, C7, C8, C9, C10, C11, or C12 alkyl). In some embodiments, in a compound of Formula A1, B1, or C1, R is a $C_{2-6}$ alkyl. In some embodiments, in a compound of Formula A1, B1, or C1, R is a C4-C6 alkyl. In some embodiments, in a compound of Formula A1 or B1, R is a C1-12 alkyoxyalkyl, such as, for example, butoxymethyl, methoxyethyl, butoxyethyl, or hexoxyethyl. Z may be a counterion, such as, but not limited to, Cl, $PF_6$, tosylate, besylate, and/or mesylate.

The active agents disclosed herein can, as noted above, be prepared in the form of their salts or pharmaceutically acceptable salts, e.g., to provide a compound or composition including a counterion as noted above. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The active agents described above may be formulated for administration in a pharmaceutical carrier in accordance with known techniques. See, e.g., Remington, The Science And Practice of Pharmacy (9th Ed. 1995). In the manufacture of a pharmaceutical formulation according to the invention, the active agent (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a solution, which may contain from 0.01 or 0.5% to 95% or 99% by weight of the active agent. One or more active agents may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active agent which is being used.

Formulations suitable for oral administration may be presented in discrete units, such as capsules, cachets, lozenges, or tablets, each containing a predetermined amount of the active agent; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active agent and a suitable carrier (which may contain one or more accessory ingredients as noted above). In general, the formulations of the invention are prepared by uniformly and intimately admixing the active agent with a liquid or finely divided solid carrier, or both, and then, if necessary, shaping the resulting mixture. For example, a tablet may be prepared by compressing or molding a powder or granules containing the active agent, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/ dispersing agent(s). Molded tablets may be made by molding, in a suitable machine, the powdered compound moistened with an inert liquid binder.

Formulations suitable for buccal (sub-lingual) administration include lozenges comprising the active agent in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active agent(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active agent(s), or a salt thereof, in a unit dosage form in a sealed container. The active agent or salt may be provided in the form of a lyophilizate which is capable of being reconstituted with a suitable pharmaceutically acceptable carrier to form a liquid composition suitable for injection thereof into a subject. The unit dosage form may comprise from about 10 mg to about 10 grams of the active agent or salt. When the active agent or salt is substantially water-insoluble, a sufficient amount of emulsifying agent which is physiologically acceptable may be employed in sufficient quantity to emulsify the active agent or salt in an aqueous carrier. One such useful emulsifying agent is phosphatidyl choline.

Formulations suitable for rectal administration are preferably presented as unit dose suppositories. These may be prepared by admixing the active agent with one or more conventional solid carriers, for example, cocoa butter, and then shaping the resulting mixture.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Of course, the liposomal formulations containing the compounds disclosed herein or salts thereof may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidylcholines, and lecithin.

In addition to active agent(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multi-dose use. Of course, as indicated, the pharmaceutical compositions of the present invention may be lyophilized using techniques well known in the art.

According to some embodiments of the present invention, provided is a kit. The kit may comprise two or more containers, wherein each of the two or more containers comprise a meso-substituted metalloporphyrin as described herein. In some embodiments, each of the two or more containers comprise a pharmaceutically acceptable composition comprising the meso-substituted metalloporphyrin in an amount of about 5 to about 25 mg (e.g., about 5, 10, 15, 20, or 25 mg) per mL of the composition. In some embodiments, the kit is a multi-dose kit.

The pharmaceutically acceptable compositions may be in a form for subcutaneous administration. In some embodiments, each of the two or more pharmaceutically acceptable compositions may be an injectable solution. Each of the two or more pharmaceutically acceptable compositions may have the same amount of the meso-substituted metalloporphyrin. In some embodiments, at least two of the two or more pharmaceutically acceptable compositions have a different amount of the active agent.

In some embodiments, the two or more pharmaceutically acceptable compositions may be in a vial, a preloaded syringe, or a self-injection delivery. The kit may comprise 2 or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) doses of the active agent. In some embodiments, the kit comprises 8-24 doses of the active agent. In some embodiments, the kit may be a one month or 28 day kit.

In some embodiments, the kit comprises an additional therapeutic agent (e.g., an antibiotic, chemotherapeutic, etc.), which may be provided in a container that is separate from the meso-substituted metalloporphyrin.

The present invention is explained in greater detail in the following non-limiting examples.

EXAMPLES

Example 1

The aims of this study were threefold: 1) to evaluate the potential protective effects of MnBuOE when combined with RT/cisplatin over the timeline for immediate, early, and late effects; 2) to verify that MnBuOE does not protect HNSCC from combination RT/cisplatin; and 3) to evaluate the efficacy of low doses of MnBuOE given 3 times per week at preventing late injury while using a clinically relevant combination therapy of fractionated RT/cisplatin.

Materials and Methods

Animals: For normal tissue studies, six-to-eight week-old female C57Bl/6 mice were used (Jackson Laboratory, Bar Harbor, Me.). For tumor control studies, female nu/nu mice were obtained from the Duke University Breeding Facility. Mice were group housed in a barrier facility and allowed to acclimate to their new environment for at least one week before experiments. All work was approved by Duke University Institutional Animal Care and Use Committee.

MnBuOE synthesis and administration: MnBuOE was synthesized as previously described.(11) Each preparation of MnBuOE passed quality and purity tests (i.e. thin-layer chromatography, UV-vis, ESI-MS and fluorescence and elemental analyses). Mouse injections were administered subcutaneously, with MnBuOE dissolved in sterile saline. Mice received an initial dose of 0.2, 0.6, or 2.0 mg/kg, followed by three times per week (t.i.w.) maintenance doses of one-half of the loading dose (i.e., 0.1, 0.3, or 1.0 mg/kg, respectively) (termed 2/1, 0.6/0.3 and 0.2/0.1 dosing schedules). Mice used for intravital microscopic analysis of leukocyte-endothelial cell interactions and the GSH/GSSG assay received a single dose of 0.2 mg/kg 24 hours before radiation.

Salivary gland and oral mucosa irradiation: Twenty-four hours following administration of a MnBuOE loading dose, mice were anesthetized with 1.5% isoflurane gas mixed with oxygen and placed in an X-RAD 225Cx (Precision X-ray Inc., North Branford, Conn.) small animal micro-CT irradiator. A collimating cone that produced a 15 mm×40 mm radiation field was used to target the radiation beam to the salivary gland and oral cavity. The RT field included all major and minor salivary glands (located primarily in the neck region of mice), and the oral mucosa, including glands of the cheeks, lips and tongue. The target tissues were localized within the radiation field with a source-to-subject distance of 30.76 cm, using fluoroscopy at 40 kVp and 2.5 mA with a 2 mm Al filter. QC dosimetry studies confirmed that the RT dose administered during the fluoroscopy session was low (6-12 cGy). The target area was then irradiated using opposed lateral beams at a dose rate of 300 cGy/minute at target depth with 225 kVp and 13 mA and a 0.3 mm Cu filter for a total dose 9 Gy. Control mice were anesthetized but not imaged fluoroscopically or irradiated.

Mucositis evaluation using fluorescence molecular tomography: As reported previously, we used ProSense 750EX (Perkin Elmer, Waltham, Mass.) to detect mucositis. ProSense 750EX is a near-infrared (NIR) imaging agent that is cleaved by cathepsins, a family of enzymes that are expressed during inflammation, (17). Mice were injected intravenously with 100 µL ProSense 750EX. Twenty-four hours after injection, mice were anesthetized via isoflurane and imaged using the Visen FMT 2500LX (Perkin Elmer). The ProSense 750EX signal was quantified using TrueQuant software (Perkin Elmer Life and Analytical Sciences, Downers Grove, Ill.).

Imaging leukocyte-endothelial cell interactions using intravital microscopy: Imaging was performed 24 hours following irradiation/sham RT. Mice were anesthetized with 80/8 mg/kg ketamine/xylazine mixture. Acridine orange (Sigma-Aldrich, St. Louis, Mo.) was injected intravenously (100 µl of 0.1% acridine orange in saline). The ventral surface of the tongue was placed on a glass cover slip before mounting the mouse onto a Zeiss Observer.Z1 (Carl Zeiss AG, Oberkochen, Germany) inverted microscope equipped with Zeiss Filter Set 38. Fluorescent excitation was performed at 470 nm, and video was obtained at 525 nm using a 40× objective. Two separate regions with at least four veins in the 15-50 mm range were identified, and a 60-120 second long video at 5 frames-per-second was obtained using Zen Imaging Software (Carl Zeiss AG, Oberkochen, Germany). Mice were kept warm while anesthetized using a heated stage.

Leukocyte-endothelial cell interaction analysis: All video analysis was performed in a blinded fashion. Rolling leukocytes were defined as cells that marginated along the vessel wall and were clearly dissociated from the bulk blood flow. Four vessels were analyzed per mouse. Leukocyte counting was repeated in triplicate for each vessel and averaged to obtain the flux of rolling leukocytes ($F_{rolling}$). Vessel diameter (D) and the velocity of at least one free-flowing leukocyte(s) ($V_L$) were also measured. A pseudo shear rate ($g_s$) was also calculated for each vessel as: $g_s=8V_L/D$. These methods have been described previously. (18)

GSH/GSSG sample preparation: This procedure was modified from a previously published method analyzing glutathione in whole blood.(19) Following euthanasia, mouse tongues were resected and flash frozen in liquid nitrogen and stored at −80° C. until use. Samples (20 mg) were homogenized with: 4 parts (g/vol) of GSH-trapping solution (20 mM N-ethylmaleimide (NEM; Sigma, St. Louis, Mo.), 2% SSA and 2 mM EDTA in 15% methanol), 10 parts (g/vol) of 1% formic acid (Fluka Inc., St. Louis, Mo.) and two 2.5 mm Zr-silica beads (Biospec Products Inc., Bartlesville, Okla.) in FastPrep (Thermo Fisher Scientific, Waltham, Mass.) homogenizer at speed 5 for 40 s. After 30 min incubation at room temperature, 500 µL of chloroform was added to 150 µL of the homogenate, mixed for 40 s, followed by centrifugation at 16,000 g for 5 min. For GSH analysis, 5 µL of supernatant, 1 mL of deionized water, and 100 µL of 1 µM GSH-NEM-d3 (internal standard) was combined and placed into autosampler at 4° C. For GSSG analysis 20 µL of supernatant and 20 µL of 1 µM GSSG-d6 in mobile phase A was combined and placed into an autosampler at 4° C.

LC-MS/MS Analysis: The measurement of GSH (as GSH-NEM derivative) and GSSG was performed on Shimadzu 20A series liquid chromatography (LC; Shimadzu Scientific Instruments, Columbia, Md.) and Applied Biosystems/SCIEX API5500 QTrap tandem-mass spectrometer (MS/MS; Applied Biosystems, Foster City, Calif.). LC conditions: Column Agilent ZORBAX Eclipse Plus, C18 4.6× 50 mm 1.8 µm particle size (P/N 959941-902) analytical column (Agilent Technologies, Santa Clara, Calif.) and Phenomenex, C18 4×3 mm guard cartridge (P/N AJ0-4287) at 45° C. (Phenomenex, Torrance, Calif.). Mobile phase solvents (all MS-grade): A—0.1% formic acid in water, 2% acetonitrile; B—acetonitrile. Elution gradient at 1 mL/min: 0-3 min 0-50% B, 3-3.1 min 50-95% B, 3.1-3.5 min 95% B, 3.5-3.6 min 95-0% B. Run time: 7 min. MS/MS conditions: MRM transitions (m/z) followed for GSH-NEM, GSH-NEM-d3, GSSG, and GSSG-d6 were 433-304, 436.2-307.1, 613.1-355, and 619.1-361, respectively. Calibration samples (n=6) in mobile phase A were prepared in the following appropriate ranges: 0.375-6.00 mM for GSH and 1.88-30 M for GSSG analysis and analyzed alongside the study samples. Quantification was performed by Analyst 1.6.2 software.

Xerostomia quantification by stimulating saliva production: Mice were injected intraperitoneally with 3 µg carbomylcholine chloride (Sigma) dissolved in sterile phosphate-buffered saline. Salivation began 2 minutes after injection. Saliva was collected via pipette for 4 minutes. The volume was measured gravimetrically, assuming a density of 1 g/mL.

Salivary gland and tongue histology and fibrosis quantification: Salivary tissues and tongues were excised from the euthanized mice, placed in formalin for 24 hours, and embedded in paraffin. Sections (4 µm thick) that passed through the submandibular and sublingual glands were stained with Masson's trichrome. Masson's trichrome staining results in bright turquoise staining of fibrotic tissue and red staining of healthy tissue. Images were obtained using a Zeiss Imager A.1, equipped with AxioVision 4.7 software and processed using MATLAB software (MathWorks, Natick, Mass., USA). Images from three different regions of each gland were collected and used for quantification. Whole tongue images were obtained, but blue staining connective tissue beneath the papillae was excluded from analysis for blue:red quantification to account for different tongue orientations during imaging.

Tumor growth delay study: FaDu (human pharyngeal carcinoma) cells were obtained from the Duke University Cell Culture facility and were confirmed to be free of mycoplasma and known rodent pathogens. Cells were grown in Dulbecco's modified Eagle's medium with 10% fetal bovine serum. Mice were injected s.c. in the right flank with $3\times10^6$ cells suspended in 100 ml serum-free media. Seven days after implantation mice were randomized to treatment groups that received either MnBuOE (0.6 mg/kg loading dose followed by t.i.w. 0.3 mg/kg (loading/3× weekly maintenance) MnBuOE or an equivalent volume of saline. Tumors were measured daily with calipers and the volume was calculated using the equation $V=(A^2 \times B \times \pi)/6$, where A is the shortest diameter and B is the longest diameter. As tumors reached 200 mm$^3$, they randomized into radiation treatment groups consisting of three daily fractions of radiation (6, 9, 12, 15 or 17 Gy/fraction) administered on three consecutive days. Cisplatin (6 mg/kg; APP pharmaceuticals, Schaumberg, Ill.) was injected intraperitoneally four hours prior to the first radiation fraction. Sham mice were anesthetized without irradiation and did not receive cisplatin injections.

Statistics: Statistical analysis was conducted using GraphPad Prism 6 (GraphPad Software Inc., La Jolla, Calif., USA). A log-rank test (Mantel-Cox) was used to compare saline vs. MnBuOE treatments at individual radiation doses. Exploratory analysis of treatment efficacy was based on comparison of tumor tripling times across treatment arms. However, formal hypothesis testing using tripling times proved difficult due to many animals not achieving the required volume threshold, particularly at higher radiation doses. To capture the inhibitory effect in these (and other) animals, we estimated animal specific time varying tumor inhibition curves using the dynamic treatment effect (DTE) methodology (20). We used the area under the curve (AUC) of animal specific inhibition curves as a summary measure for dose response analysis. A linear dose response curve was fit with the control arm as baseline with differential slopes and intercepts for the MnBuOE arm. The isodose effect of MnBuOE was quantified and tested in terms of the estimated differential slope.

Results

Determination of Minimum Effective Dose of MnBuOE in Reducing Mucositis

We first performed a MnBuOE dose-response experiment to determine the minimum effective dose that still prevented mucositis. (FIG. 1) Unirradiated mice that received either saline or 2/1 mg/kg MnBuOE did not show an appreciable NIR signal. Radiation (1×9 Gy) induced a significant ($p<0.05$) increase in NIR signal compared with unirradiated control mice. Irradiated mice treated with MnBuOE demonstrated a decreased NIR signal with the greatest decrease occurring in mice receiving the lowest levels of MnBuOE (0.6/0.3 or 0.2/0.1 mg/kg MnBuOE ($p>0.05$)).

Leukocyte-Endothelial Cell Interactions

Figure 2A:
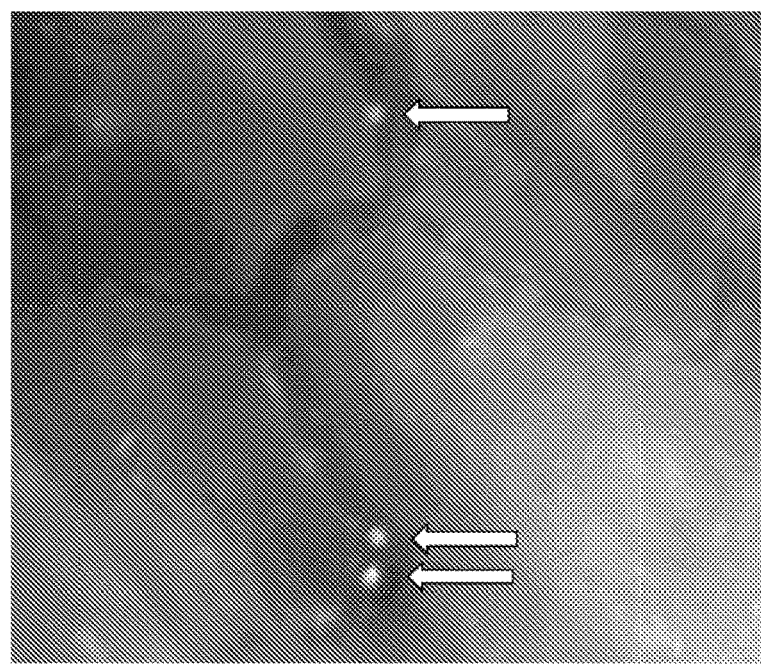
FIG. 2A shows the intravital quantification of L/E interactions and physical properties of blood vessels 24 hours post-RT with an example image obtained from intravital microscopy of the inferior surface of a mouse tongue following i.v. administration of 0.1% acridine orange solution 24 hours after RT. Three white arrows indicate rolling leukocytes visible along the venule.

Previous studies have utilized intravital microscopy to determine the magnitude of the early inflammatory response initiated by RT by directly quantifying the number of rolling leukocytes in the terminal venules of irradiated tissues including the small bowel,(21) skin,(18) and ear pinna (Ashcraft et al., Manuscript in preparation). To assess leukocyte-endothelial interactions, we obtained real-time images of the sublingual vascular bed in mice treated with saline or MnBuOE±1×9 Gy RT (FIG. 2A) Images were used to quantify rolling leukocytes 24 hours post-RT. (FIG. 2B, panel i) To determine if differences in leukocyte rolling were masked by compensatory differences in shear stress, we measured the diameters and velocities of free-flowing leukocytes in vessels used for counting, and calculated a shear rate for each vessel. (FIG. 2B, panels ii-iv) Mice treated with saline and 9 Gy had a significant increase in average velocity compared with mice treated with saline or MnBuOE alone ($p<0.05$). MnBuOE-treatment alone increased vessel diameters compared to saline control mice, but MnBuOE-treated mice that received 9 Gy RT had vessel diameters similar to those of the saline control mice ($p=0.52$). The difference in vessel diameter contributed to significantly lower shear rates in the MnBuOE-treated mice compared to all other treatment groups ($p<0.05$; Tables 1-3).

TABLE 1

Repeated measures ANOVA of blood velocity.

| Term | Effect | Std. Error | t-value | p-value |
|---|---|---|---|---|
| Baseline (Saline) | 0.15 | 0.01 | 24.26 | |
| RT | 0.02 | 0.01 | 2.40 | 0.02 |
| MnBuOE | −0.00 | 0.01 | −0.04 | 0.97 |
| MnBuOE + RT | 0.01 | 0.01 | 1.14 | 0.26 |

TABLE 2

Repeated measures ANOVA of vessel diameter.

| Term | Effect | Std. Error | t-value | p-value |
|---|---|---|---|---|
| Baseline (Saline) | 0.022 | 0.00 | 12.74 | |
| RT | 0.006 | 0.00 | 1.76 | 0.09 |
| MnBuOE | 0.009 | 0.00 | 3.81 | 0.0005 |
| MnBuOE + RT | 0.002 | 0.00 | 0.65 | 0.52 |

TABLE 3

Repeated measures ANOVA of shear rates.

| Term | Effect | Std. Error | t-value | p-value |
|---|---|---|---|---|
| Baseline (Saline) | 61.15 | 4.57 | 13.37 | |
| RT | −6.07 | 6.86 | −0.89 | 0.38 |
| MnBuOE | −20.88 | 6.32 | −3.30 | 0.002 |
| MnBuOE + RT | −0.83 | 6.08 | −0.14 | 0.89 |

GSH/GSSG Oxidative Stress Assay

The reduced to oxidized glutathione ratio (GSH/GSSG) has been used in multiple tissue types to measure the oxidative environment.(19, 22, 23) To assess the oxidative stress at the time of intravital imaging, mice were administered a single 0.2 mg/kg dose of MnBuOE 24 hours prior to RT (9 Gy) and euthanized 24 hours post-RT. We observed that radiation decreased the GSH/GSSG ratio in tongue tissue, reflecting increased oxidative stress in the cells in response to the ROS and RNS generated by the ionizing radiation, but the 16% decrease was not statistically significant. The addition of MnBuOE alone slightly increased the GSH/GSSG ratio compared to the saline and saline+RT controls, which may suggest an overall reduced oxidative stress in the tissue by MnBuOE alone. Mice receiving combination MnBuOE+RT had increased of GSH/GSSG compared to either saline control arms, averaging only 4% lower than the 0 Gy MnBuOE tongue levels.

Xerostomia

Figure 3:
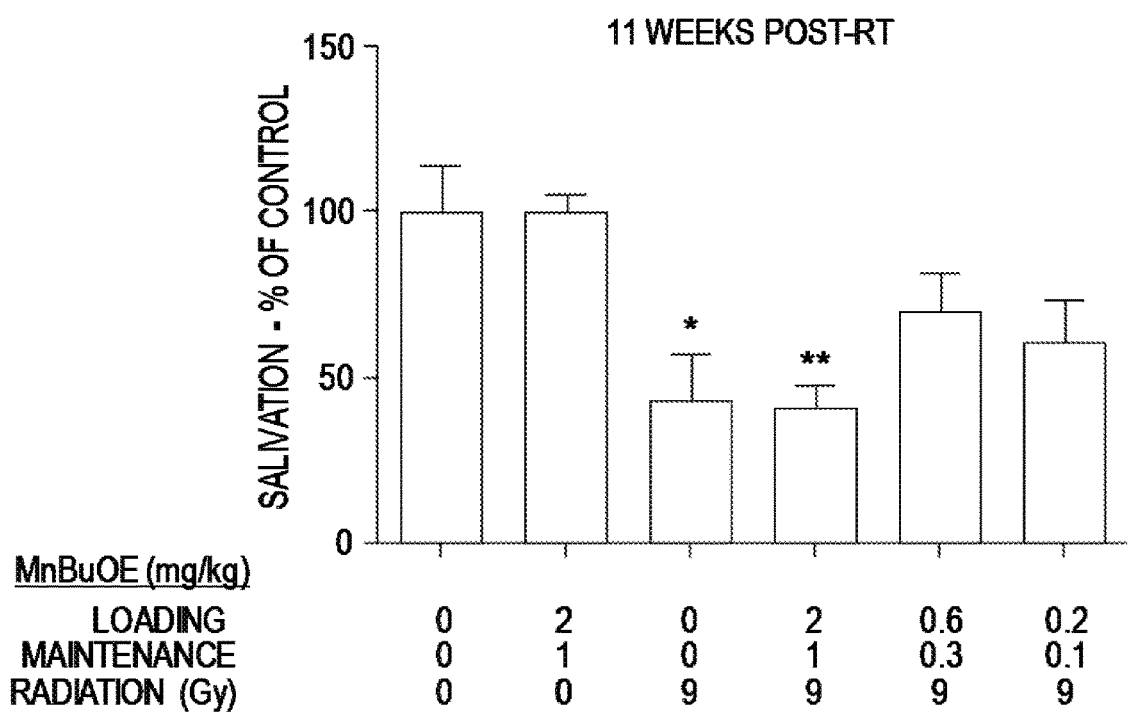
FIG. 3 shows RT-induced xerostomia at 11 weeks post-RT. To reduce variability, all mice were normalized to salivation levels for their appropriate control. Mice receiving saline or 2/1 mg/kg MnBuOE experienced significant (p<0.05) decreases in salivation in response to RT, but mice treated with either 0.6/0.3 or 0.2/0.1 mg/kg MnBuOE experienced smaller, non-significant decreases in saliva production compared with unirradiated controls. N=5-6 mice/group * Significant difference (p<0.05) vs. saline/0 Gy control ** Significant difference (p<0.05) vs 2/1 mg/kg MnBuOE/0 Gy control.

Stimulated salivation was assessed at 11 weeks post-RT (FIG. 3). In accordance with previous studies, RT significantly decreased salivation in saline-treated mice.(13, 24-26) In these studies the lowest doses of MnBuOE (0.6/0.3 or 0.2/0.1 mg/kg MnBuOE) gave the highest level of protection against xerostomia. For both the 0.6/0.3 and 0.3/0.1 mg/kg doses of MnBuOE there was no significant difference in salivation compared to unirradiated MnBuOE-treated control mice.

Salivary Gland and Tongue Fibrosis

Figure 4A:
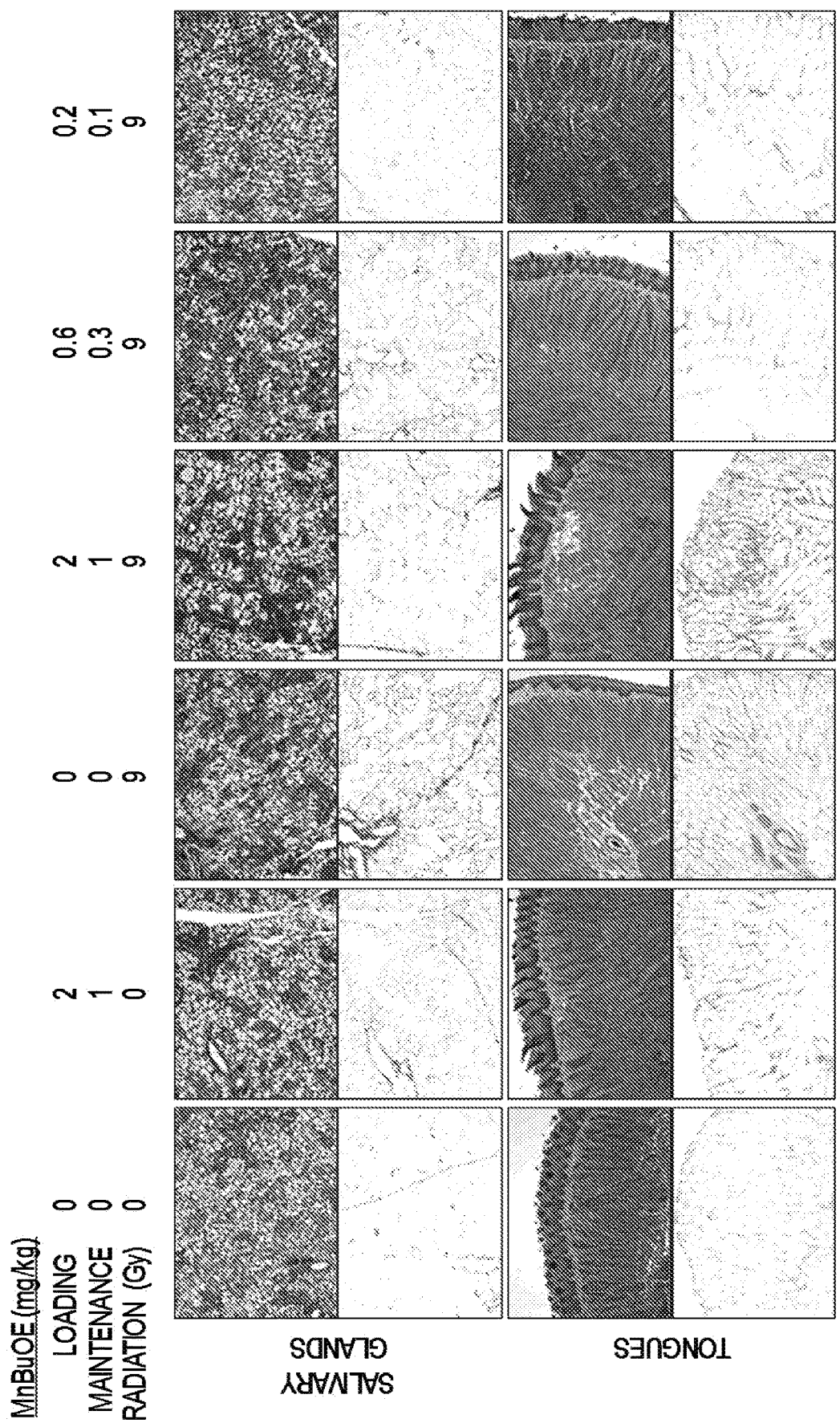
FIG. 4A shows analysis of fibrosis in salivary glands and tongues at 12 weeks post-RT with images of Masson's trichrome staining in the salivary glands and tongue, which distinguishes fibrotic tissue (stained blue) and healthy tissue (stained red).
Figure 4C:
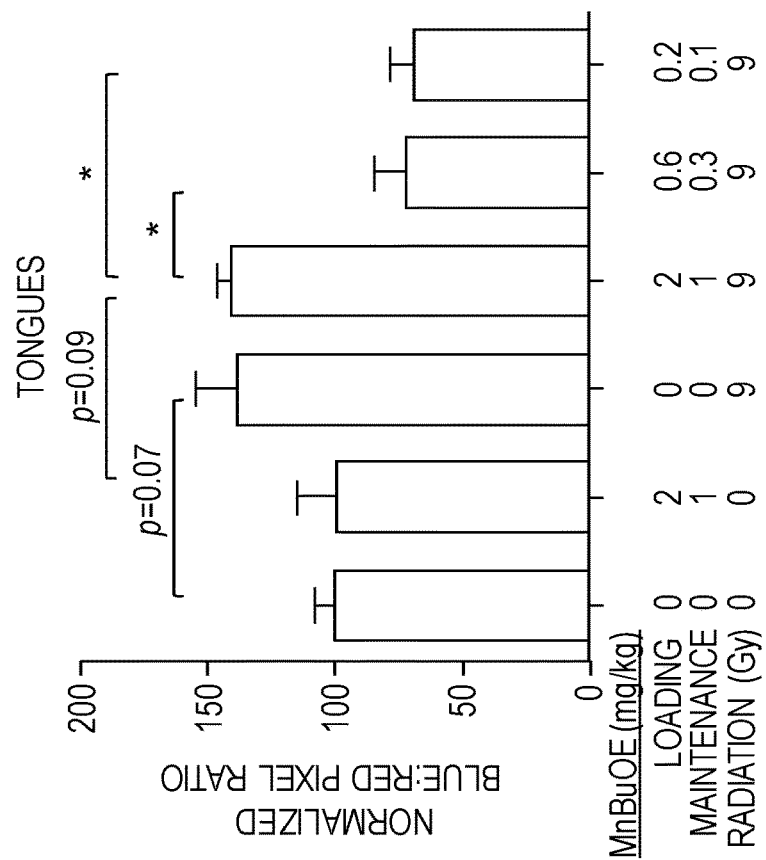
FIG. 4C shows a graph of fibrosis in the tongue normalized to the control value of either saline of 2/1 mg/kg MnBuOE control. As in the salivary glands, 9 Gy lead to an increase in fibrosis. Both 0.6/0.3 and 0.2/0.1 mg/kg MnBuOE reduce fibrosis to a greater degree than 2/1 mg/kg. N=4-6 mice/group. * Significant difference (p<0.05) vs. saline/0 Gy control.
Figure 4B:
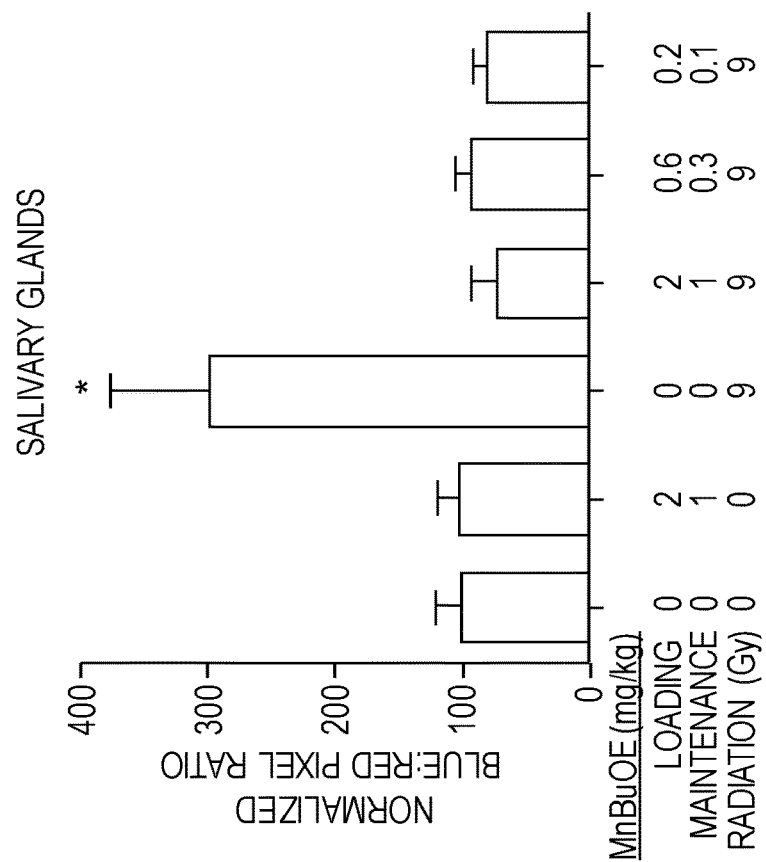
FIG. 4B shows a graph of fibrosis in the salivary glands normalized to the control value of either saline or 2/1 mg/kg MnBuOE control. 9 Gy increases fibrosis in mice that received saline only. MnBuOE attenuates fibrosis in irradiated mice, with all doses of MnBuOE are equally effective at reducing fibrosis. N=4-6 mice/group. * Significant difference (p<0.05) vs. saline/0 Gy control

Fibrosis in the salivary glands and tongue were examined 12 weeks post-RT (FIG. 4A). Radiation therapy resulted in a significant increase in fibrosis in both salivary glands and tongue while treatment with MnBuOE protected against this fibrosis in both salivary gland and tongue, particularly at the lower levels of treatment with MnBuOE. Saline+RT significantly increased blue:red pixel ratio in the salivary glands ($p<0.05$) (FIG. 4B). The blue:red pixel ratio was not significantly different between mice treated with MnBuOE+RT (at all levels of MnBuOE) compared to control animals that did not receive RT. In the tongue (FIG. 4C), treatment with RT+0.6/0.3 or 0.2/0.1 mg/kg MnBuOE resulted in a significant decrease in fibrosis.

Tumor Growth Control Studies

Figure 5:
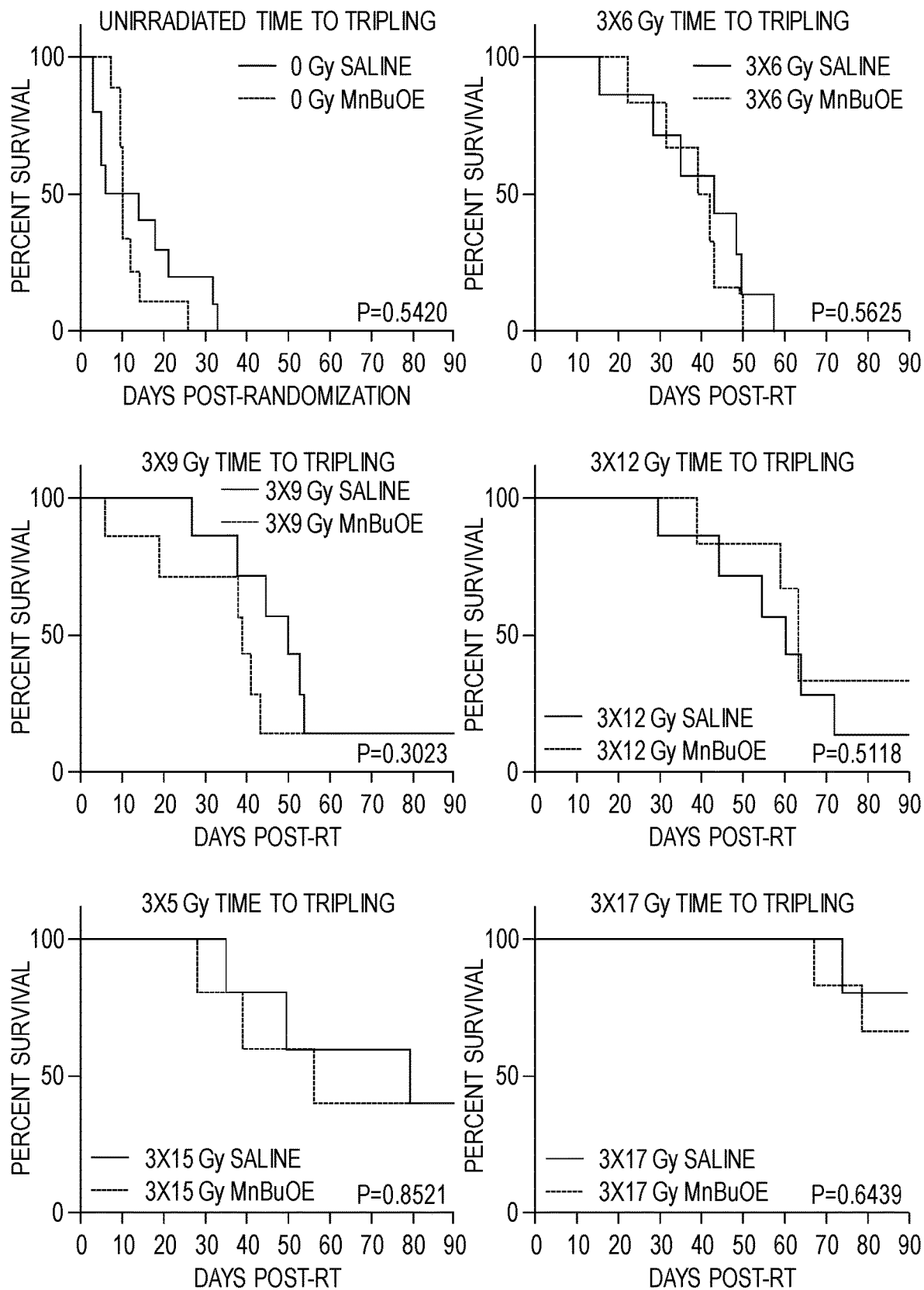
FIG. 5 shows graphs that demonstrate that MnBuOE did not interfere with radiation/cisplatin-mediated tumor growth delay in a murine xenograft model. The human pharyngeal carcinoma tumor cell line (FaDu) was transplanted to flanks of nude mice randomized to receive fractionated RT+cisplatin along with MnBuOE treatment or saline control injections. MnBuOE was started one week after transplanted and continued t.i.w. for the duration of the experiment. RT+cisplatin was initiated as tumors reached 200 mm³. Differences in tumor growth rate were compared by assessing time to tripling of tumor volume, using the initial treatment volume of reach mouse as baseline.

We have previously shown that higher doses of MnBuOE sensitized a head and neck tumor xenograft to radiation (13). However, most head and neck cancer patients will receive RT with chemotherapy, such as cisplatin. The effects of MnBuOE at a lower dose (to mimic what was done for normal tissues, above, in conjunction with RT+cisplatin) were investigated. We found a significant effect of radiation dose on tumor growth ($p>0.0001$), but MnBuOE (0.6 mg/kg loading dose followed by t.i.w. 0.3 mg/kg maintenance dosing) did not significantly affect tumor growth, relative to RT/cisplatin. Kaplan-Meier analysis showed no significant differences at any radiation dose between MnBuOE and saline treated mice (FIG. 5). By day 90 post-treatment, the percentages of mice with complete tumor regression in the 3×12Gy, 3×15Gy and 3×17Gy treatment groups were 14%, 40% and 20%, respectively for saline-treated mice, and 33%, 40% and 50%, respectively for the MnBuOE treated mice. No mice were tumor-free at 90 days post-treatment in the sham, 3×6Gy or 3×9 Gy groups.

As a deeper analysis, we compared the dose response relationship of tumor inhibition, as quantified by the AUC of animal specific dynamic treatment effect curves, across the control and MnBuOE arms. There was no significant difference in the slope of the dose response curve for the two arms ($p$-value=0.47).

Normal Tissue Protection from Combined RT and Cisplatin Treatment.

Figure 6A:
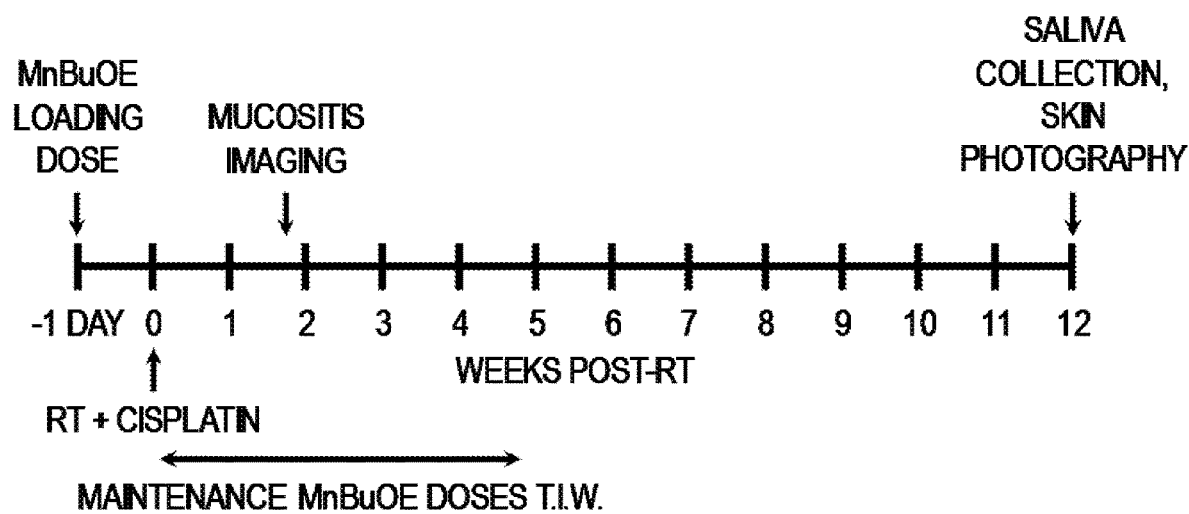
FIG. 6A shows a schematic of a timeline for treatment. Mice were treated with 1×9Gy+6 mg/kg cisplatin. Saline or MnBuOE treatment (0.6 mg/kg loading dose) began 24 hours prior to RT+cisplatin, and maintenance dosing of MnBuOE (0.3 mg/kg) continued t.i.w. for five weeks.
Figure 6B:
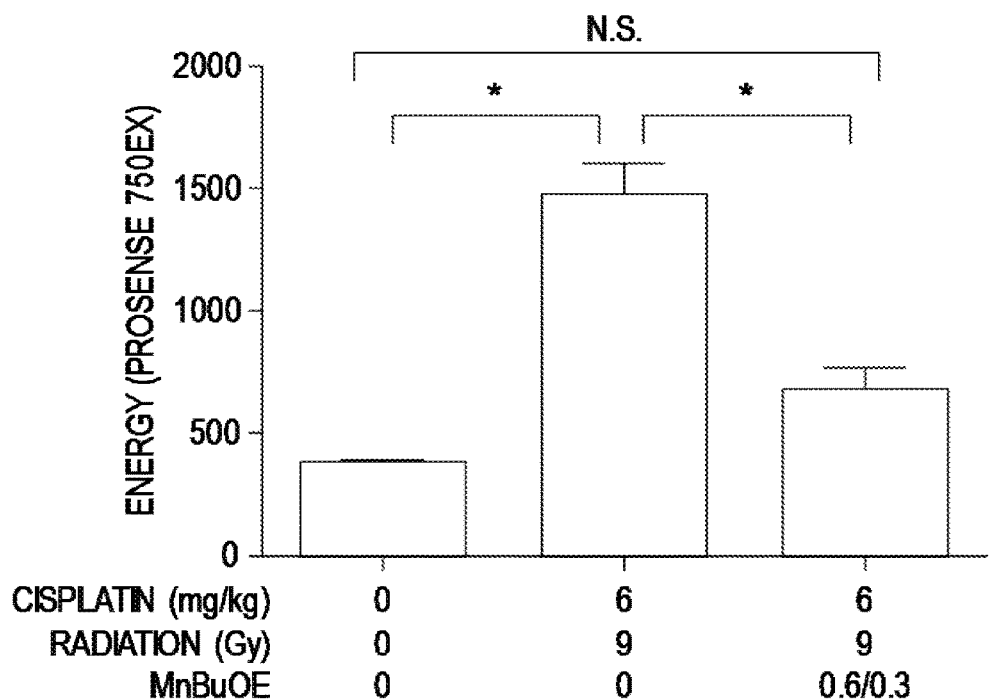
FIG. 6B shows a graph and that MnBuOE protects mice against normal tissue injury following RT+cisplatin. RT+cisplatin increased NIR signaling in saline treated mice compared to unirradiated controls (p<0.01), and to MnBuOE treated mice that received RT+cisplatin (p<0.01). MnBuOE mice treated with RT+cisplatin did not show significantly greater NIR signal than unirradiated controls. (p=0.002, across all groups (ANOVA), N=2-4/group).
Figure 6B:
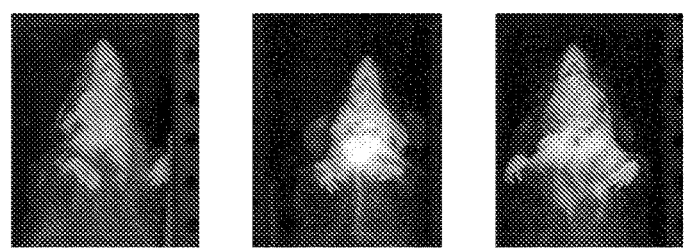

Finally, to confirm that normal tissue injury resulting from combination therapies of RT and cisplatin would not be too great for MnBuOE to protect against, we conducted a study to compare mucositis and xerostomia in mice treated with 1×9 Gy+6/mg/kg cisplatin. To answer the question of how long MnBuOE should be administered post-RT, MnBuOE administration continued for 5 weeks (FIG. 6A). As expected, the combination therapy of RT+cisplatin significantly increased NIR signaling compared to untreated, saline controls (FIG. 6B). Mice that were treated with 0.6 mg/kg loading dose followed by t.i.w. 0.3 mg/kg maintenance dose of MnBuOE showed significantly less NIR signal than did mice treated with saline plus RT+cisplatin. The NIR signal for mice receiving the 0.6/0.3 dose of MnBuOE was not statistically different from unirradiated saline control mice.

Figure 6C:
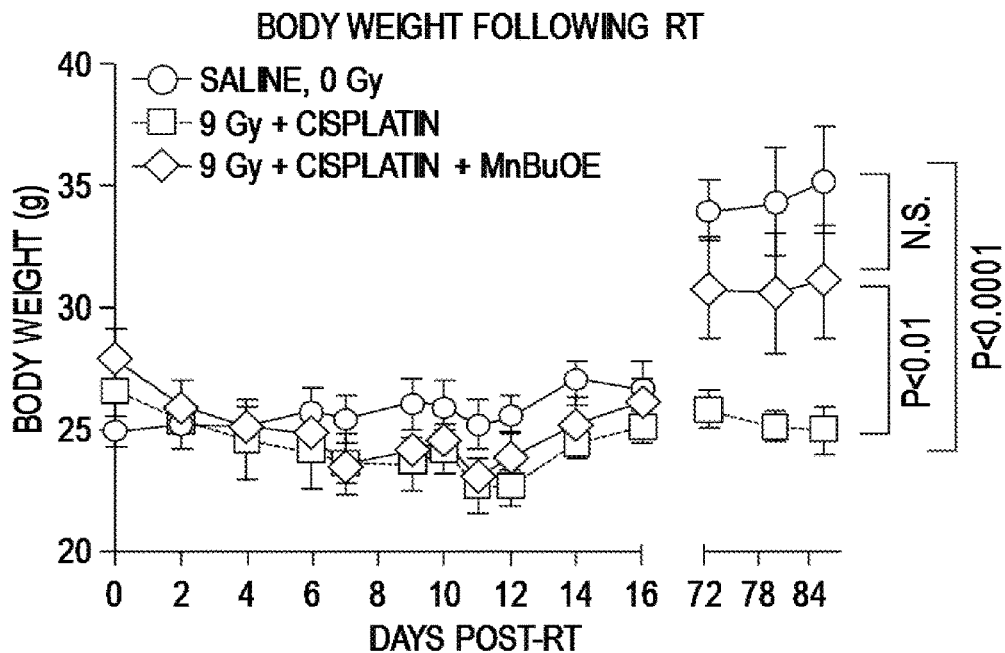
FIG. 6C shows a graph, which demonstrates that all RT+cisplatin-treated mice showed initial weight loss 8-14 days following treatment. At 10 weeks post-RT+cisplatin, the MnBuOE mice had body weights that were not significantly different from unirradiated control mice. RT+cisplatin-treated saline mice had significantly lower body-weights compared to unirradiated (p<0.0001) and RT+cisplatin MnBuOE-treated (p<0.01) mice. Two-way ANOVA showed a significant interaction between time and treatment group (p=0.018).
Figure 6D:
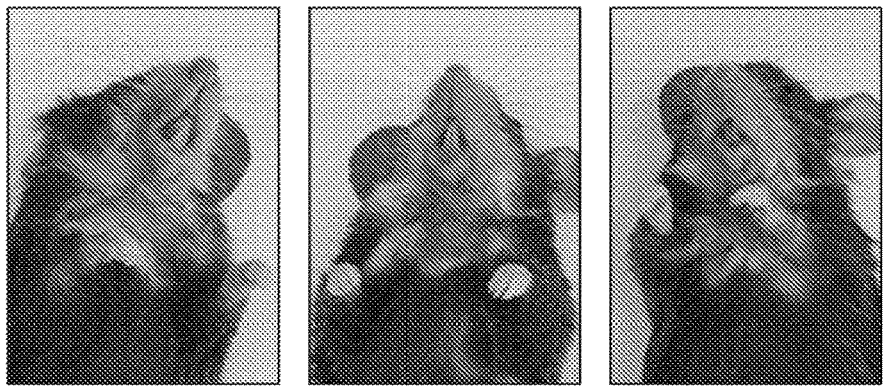
FIG. 6D shows images of mice and that MnBuOE lessened long-term ulcerations and moist desquamation in the irradiated area (right) compared to mice that received RT+cisplatin with saline (left).
Figure 6D:
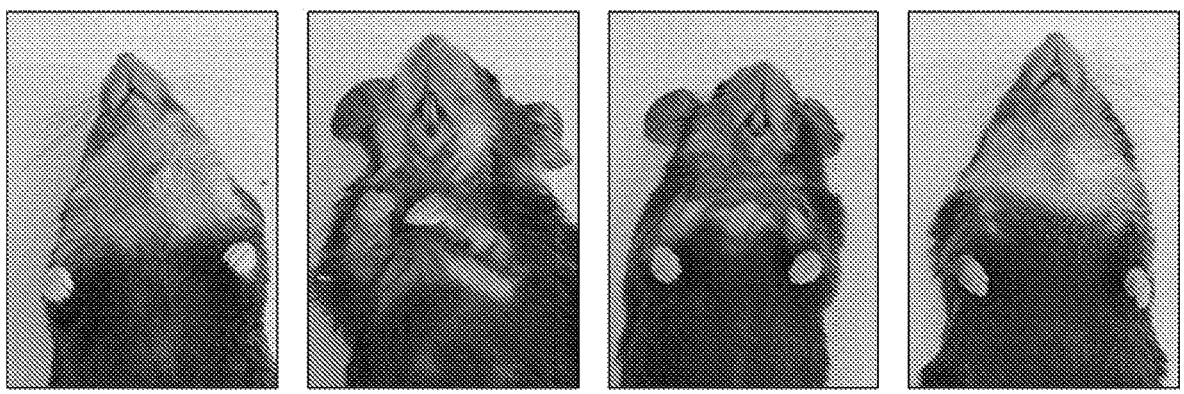

We aimed to evaluate xerostomia at 12 weeks post-RT+cisplatin; however, the saline control mice in the RT+cisplatin, group had deteriorated to the point where we were unable to collect saliva without causing ulcerations in the mouth to bleed, thereby confounding our results. Notably, the RT+cisplatin, saline mice failed to gain weight in the weeks post-RT (FIG. 6C), and had severe moist desquamation of the skin in the irradiated region that failed to heal (FIG. 6D, left group). The mice that had received MnBuOE following RT+cisplatin did not have actively bleeding mouth ulcers, and only 1 out of 4 mice still had ulcers in the mouth and surrounding skin and had failed to gain weight post-RT. An additional mouse in this group showed scarring of the skin, but had had weight gain similar to untreated controls (FIG. 6D, right group). The remaining two mice showed leukotrichia only, with normal weight gain and no scarring or ulcers.

MnBuOE Radioprotection Dose-Response is Non-Linear

Our data demonstrate that in this model, t.i.w. MnBuOE is effective at decreasing mucositis at very low doses (0.2/0.1 mg/kg, t.i.w.). We have previously reported that higher levels of MnBuOE (1.5 mg/kg b.i.d.) are associated with protection against radiation-induced mucositis, xerostomia and salivary gland fibrosis. In addition, this higher dose of MnBuOE enhanced tumor local control rates compared with controls showing that MnBuOE widens the therapeutic margin by decreasing the dose of radiation required to control tumor and at the same time increasing tumor resistance to RT-mediated injury. The current study shows a substantial level of protection against the radiation-induced effects of mucositis, xerostomia, and both salivary gland and tongue fibrosis using a maintenance dose that is approximately 60 times lower (0.1 mg/kg t.i.w. compared to 1.5 mg/kg bid).

We previously reported that a single fraction of 9-15 Gy administered to the submandibular salivary gland significantly decreased salivation and increased fibrosis following RT. In this study the dosing schedule was modified to 2-3 times weekly doses of one-half the initial loading dose). This pattern of maintenance dosing is more practical than is a b.i.d. dosing schedule. We also identified a similar impact of protection against tongue fibrosis using the low level MnBuOE dosing schedule. To our knowledge, this is the first preclinical work using tongue fibrosis as a normal tissue injury endpoint for a radioprotectant.

Radiation induces both acute and chronic oxidative stress and inflammation. We were encouraged to find that cessation of MnBuOE at five weeks post-RT+cisplatin conferred protection against late ulcerations and sustained weight loss. Although we were unable to satisfactorily quantify saliva production, due to the small number of mice and deteriorating oral mucosa, we did indeed see a trend towards reduced xerostomia at 10, 11 and 12 weeks in mice that received MnBuOE for the first five weeks after RT+cisplatin (data not shown.)

Intravital Microscopy can be Used to Non-Invasively Quantify Leukocyte-Endothelial Cell Interactions and Microvessel Characteristics in the Oral Cavity It is well-established that radiation causes an increase in leukocyte-endothelial cell interaction (rolling and adhesion) in post-capillary venules.(18, 21) Leukocytes that initiate an inflammatory response in the tissue first roll along the endothelium before adhering and ultimately migrating through the vessel wall and into the parenchyma.(18, 21) Rolling and adhesion occur in response to changes in cytokine, selectin, and integrin expression that begin within minutes of exposure to radiation. In model systems, such as the mouse small bowel, this effect persists in excess of 24 hours, with a period of increased rolling generally preceding a period of increased adhesion before returning to normal. (21)

Figure 2B:
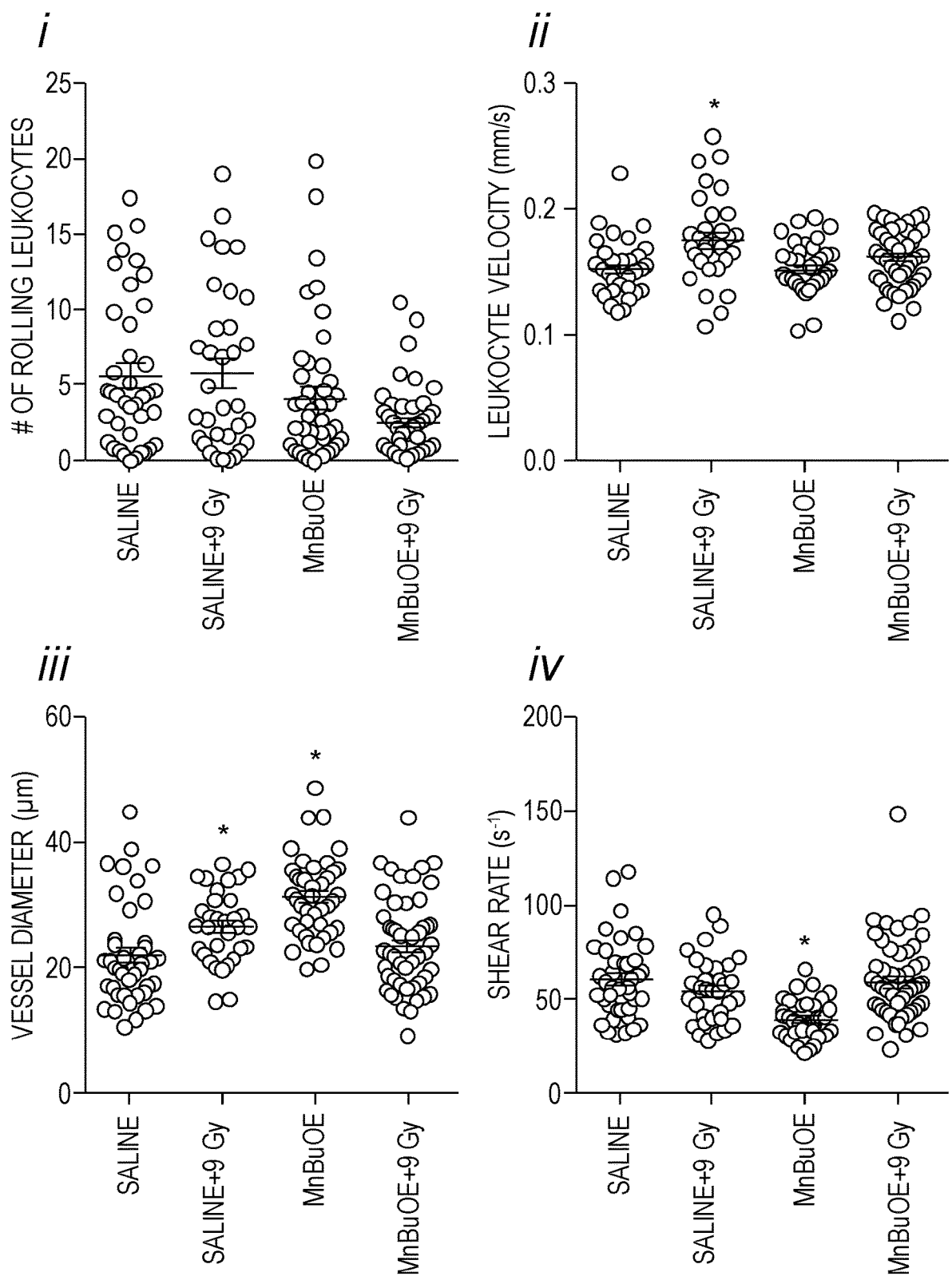
FIG. 2B shows graphs relating to the intravital quantification of L/E interactions and physical properties of blood vessels 24 hours post-RT. The graph in panel i. shows that the mean number of rolling leukocytes decreases in response to a combination of 0.2/0.1 MnBuOE and RT. The graph in panel ii. shows that RT increased the mean velocity of free-flowing leukocytes in the blood ($V_L$) in mice treated with saline. This effect was not observed in mice treated with MnBuOE. The graph in panel iii. shows that treatment with RT or MnBuOE alone (2/1) led to an increase in the average diameter (D) of blood vessels. Combination RT+MnBuOE (0.2/0.1) did not lead to an increase in diameter vs. the saline control. The graph in panel iv. shows that only mice treated with MnBuOE alone (2/1) experienced a decrease in shear rate, primarily driven by increased vessel diameter. Shear rates ($g_s$) were calculated with the formula $g_s=8V/ID$. Data points are presented for each vessel, along with mean and SEM. N=8-13 mice/group * Significant difference (p<0.05) vs. saline/0 Gy control.

We are the first to report this non-invasive method for directly measuring leukocyte-endothelial cell interactions in the sublingual vascular bed. Our findings are different from previous studies in two key respects: 1) there was no appreciable degree of leukocyte adhesion, and 2) treatment with radiation alone did not lead to an increase in the quantity of rolling leukocytes 24 hours following RT. These differences stress the importance of considering anatomical differences when assessing vascular RT injury. MnBuOE treatment alone significantly increased vessel diameter, which translated into a significantly reduced shear rate (FIG. 2biv). One would expect that a lower shear rate would promote leukocyte rolling, as marginating leukocytes experience reduced forces parallel to the direction of blood flow.(18) The observation that MnBuOE treatment alone decreased shear rate without increasing leukocyte rolling could suggest a decrease in adhesion molecule expression.

It is surprising that we did not observe an increase in leukocyte rolling in response to RT, because a single 9 Gy fraction was sufficient to induce mucositis, xerostomia, and salivary gland fibrosis. It is possible that the increase in rolling occurred and resolved completely before the time that imaging was performed, although it has been established that increased rolling persists through 24 hours in other tissue models.(21) Further trials with sequential imaging might be able to determine when maximum leukocyte rolling occurs in this model. Our studies were initiated with the anticipation that observed changes in leukocyte rolling could serve as an image-based biomarker for later RT-mediated normal tissue injury. However, our results show that for the oral mucosa, late injury develops in the absence of measurable very early vascular changes.

It is possible that prolonged RT-induced activation of NF-κB will result in chronic effects on the cellular environment by inducing secondary oxidative stress.(27) Thus, MnBuOE, which suppressed activation of NF-κB, will exhibit its protective effect as long as secondary oxidative stress persists. Optimal protection against this mechanism of injury may require administration of MnBuOE for a prolonged period of time. The full effect of oxidative damage is therefore not necessarily apparent within the timescale we investigated with intravital microscopy.

MnBuOE Decreases RT-Induced Fibrosis

Xerostomia progressively develops in the weeks/months following RT and is a reflection of damage to the salivary gland stem cells, which decreases the tissues' regenerative capacity.[28] Xerostomia is often irreversible and has significant long-term consequences for a patient's oral health and overall quality of life.(2, 28, 29) Our salivary gland fibrosis results demonstrate persistent damage following RT, which is prevented by MnBuOE and may correlate with reduced risk of chronic xerostomia.

MnBuOE Tumor Radiosensitization is Dose Dependent

Due to the intrinsic differences in redox environments of tumor vs normal tissue (30, 31), Mn porphyrin exhibit differential effects in those tissues: healing of normal while suppressing growth of tumor. In our previous work, we showed that higher doses of MnBuOE (1.5 mg/kg b.i.d.) radiosensitized FaDu tumors, shifting the $TCD_{50}$ curve to the right with a dose-modifying effect of 1.3 (13). We now report a null effect of MnBuOE on FaDu tumors in this study. There are significant differences in these experiments that likely explain the different responses of MnBuOE on FaDu tumors. First, we previously used five fractions of radiation (5-10 Gy/fraction), as opposed to the three fractions (6-17 Gy/fraction) described herein. It should be noted that these radiation doses were not chosen capriciously. Assuming a tumor $\alpha/\beta=10$, the BEDs chosen for this study ranged from 28.8-137.7, which provided adequate coverage of the previous study's BED range (37.5-100). Though the BED was constant, reducing our fractions from five to three could have decreased the radiosensitizing benefits of fractionation that come with reoxygenation and redistribution. A comprehensive evaluation of different dose fractionation schemes was beyond the scope of this study, but future experiments could investigate MnBuOE efficacy using different radiation approaches at a fixed MnBuOE dose.

Second, the mechanisms by which MnBuOE is predicted to sensitize tumor cells will differ as the drug dose decreases. With b.i.d. dosing of 1.5 mg/kg, MnBuOE accumulates in the tumor (eventually reaching ~1.5-2 µM in a FaDu flank xenograft, data not shown). The studies in this manuscript were based on updated pharmacokinetic data that used recently clarified tissue half-life information and would have resulted in maintenance of a lower tumor MnBuOE concentration. Our recent studies suggested that the major in vivo action of MnBuOE is pro-oxidative in nature, due to apoptosis-promoting protein thiol S-glutathionylation (32). The magnitude of such oxidative modification is directly related to the levels of major reactive species involved in the process: $H_2O_2$ and MnBuOE. In comparison to our earlier study, this study's lower MnBuOE dose likely precluded such apoptotic events.

Finally, a third difference between our studies was the addition of cisplatin, which was included to increase the study's clinical relevance. Additionally, cisplatin increases mitochondrial oxidative stress (33), which is associated with increased normal tissue injury (34, 35) that can be ameliorated by reducing oxidative stress (36). We sought to determine whether tumor cell killing and/or normal tissue injury by cisplatin were decreased or abrogated by the addition of MnBuOE. We demonstrate that treatment with low levels of MnBuOE protects against RT-induced damage to normal tissues, without inhibiting tumor control achieved by combination therapy with RT+cisplatin.

This study demonstrates that MnBuOE is able to provide radioprotection in normal head and neck tissues at lower doses than previously reported. Radioprotection persists from 24 hours to 12 weeks following RT, as measured by mucositis, saliva production, and tissue fibrosis. Finally, MnBuOE did not affect tumor sensitivity to fractionated RT+cisplatin. Taken together, these data support the use of MnBuOE as a normal tissue radioprotecting agent during treatment of head and neck cancer.

REFERENCES

1. Siegel R L, Miller K D, Jemal A. Cancer statistics, 2016. CA: a cancer journal for clinicians. 2016; 66(1):7-30.
2. Vissink A, Jansma J, Spijkervet F K L, Burlage F R, Coppes R P. Oral sequelae of head and neck radiotherapy. Critical Reviews in Oral Biology & Medicine. 2003; 14(3):199-212.
3. Giro C, Berger B, Boelke E, Ciernik I F, Duprez F, Locati L, et al. High rate of severe radiation dermatitis during radiation therapy with concurrent cetuximab in head and neck cancer: Results of a survey in EORTC institutes. Radiotherapy and Oncology. 2009; 90(2):166-71.
4. Elting L S, Cooksley C D, Chambers M S, Garden A S. Risk, outcomes, and costs of radiation-induced oral mucositis among patients with head-and-neck malignancies.
International journal of radiation oncology, biology, physics. 2007; 68(4):1110-20.
5. Brizel D M, Wasserman T H, Henke M, Strnad V, Rudat V, Monnier A, et al. Phase III randomized trial of amifostine as a radioprotector in head and neck cancer. Journal of Clinical Oncology. 2000; 18(19):3339-45.

6. Rades D, Fehlauer F, Bajrovic A, Mahlmann B, Richter E, Alberti W. Serious adverse effects of amifostine during radiotherapy in head and neck cancer patients. Radiotherapy and Oncology. 2004; 70(3):261-4.
7. Wasserman T H, Brizel D M, Henke M, Monnier A, Eschwege F, Sauer R, et al. Influence of intravenous amifostine on xerostomia, tumor control, and survival after radiotherapy for head-and-neck cancer: 2-year follow-up of a prospective, randomized, phase III trial. International Journal of Radiation Oncology Biology Physics. 2005; 63(4):985-90.
8. Tarnawski R, Fowler J, Skladowski K, Swierniak A, Suwinski R, Maciejewski B, et al. How fast is repopulation of tumor cells during the treatment gap? International journal of radiation oncology, biology, physics. 2002; 54(1):229-36.
9. Skladowski K, Law M G, Maciejewski B, Steel G G. Planned and unplanned gaps in radiotherapy: the importance of gap position and gap duration. Radiotherapy and oncology: journal of the European Society for Therapeutic Radiology and Oncology. 1994; 30(2):109-20.
10. Russo G, Haddad R, Posner M, Machtay M. Radiation treatment breaks and ulcerative mucositis in head and neck cancer. The oncologist. 2008; 13(8):886-98.
11. Rajic Z, Tovmasyan A, Spasojevic I, Sheng H, Lu M, Li A M, et al. A new SOD mimic, Mn(III) ortho N-butoxyethylpyridylporphyrin, combines superb potency and lipophilicity with low toxicity. Free Radical Biology and Medicine. 2012; 52(9):1828-34.
12. Tovmasyan A, Sampaio R S, Boss M-K, Bueno-Janice J C, Bader H B, Thomas M, et al. Anticancer therapeutic potential of Mn porphyrin/ascorbate system. Free Radical Biology and Medicine. 2015; 89:1231-47.
13. Ashcraft K A, Boss M-K, Tovmasyan A, Choudhury K R, Fontanella A N, Young K H, et al. Novel Manganese-Porphyrin Superoxide Dismutase-Mimetic Widens the Therapeutic Margin in a Preclinical Head and Neck Cancer Model. International Journal of Radiation Oncology Biology Physics. 2015; 93(4):892-900.
14. Weitzel D H, Tovmasyan A, Ashcraft K A, Rajic Z, Weitner T, Liu C, et al. Radioprotection of the brain white matter by Mn(III) n-Butoxyethylpyridylporphyrin-based superoxide dismutase mimic MnTnBuOE-2-PyP5+. Molecular cancer therapeutics. 2015; 14(1):70-9.
15. Batinic-Haberle I, Tovmasyan A, Roberts E R, Vujaskovic Z, Leong K W, Spasojevic I. SOD therapeutics: latest insights into their structure-activity relationships and impact on the cellular redox-based signaling pathways. Antioxidants & redox signaling. 2014; 20(15):2372-415.
16. Gad S C, Sullivan D W, Jr., Spasojevic I, Mujer C V, Spainhour C B, Crapo J D. Nonclinical Safety and Toxicokinetics of MnTnBuOE-2-PyP5+ (BMX-001). International journal of toxicology. 2016; 35(4):438-53.
17. Pham C T N. Neutrophil serine proteases: specific regulators of inflammation. Nat Rev Immunol. 2006; 6(7):541-50.
18. Kimura H, Wu N Z, Dodge R, Spencer D P, Klitzman B M, McIntyre T M, et al. Inhibition of radiation-induced up-regulation of leukocyte adhesion to endothelial cells with the platelet-activating factor inhibitor, BN52021. Int J Radiat Oncol Biol Phys. 1995; 33(3):627-33.
19. Moore T, Le A, Niemi A K, Kwan T, Cusmano-Ozog K, Enns G M, et al. A new LC-MS/MS method for the clinical determination of reduced and oxidized glutathione from whole blood. Journal of chromatography B, Analytical technologies in the biomedical and life sciences. 2013; 929:51-5.
20. Choudhury K R, Keir S T, Ashcraft K A, Boss M K, Dewhirst M W. Dynamic treatment effect (DTE) curves reveal the mode of action for standard and experimental cancer therapies. Oncotarget. 2015; 6(16):14656-68.
21. Johnson L B, Riaz A A, Adawi D, Wittgren L, Back S, Thornberg C, et al. Radiation enteropathy and leucocyte-endothelial cell reactions in a refined small bowel model. BMC surgery. 2004; 4:10-.
22. Zitka O, Skalickova S, Gumulec J, Masarik M, Adam V, Hubalek J, et al. Redox status expressed as GSH:GSSG ratio as a marker for oxidative stress in paediatric tumour patients. Oncology Letters. 2012; 4(6):1247-53.
23. Lakritz J, Plopper C G, Buckpitt A R. Validated High-Performance Liquid Chromatography-Electrochemical Method for Determination of Glutathione and Glutathione Disulfide in Small Tissue Samples. Analytical Biochemistry. 1997; 247(1):63-8.
24. Cotrim A P, Sowers A L, Lodde B M, Vitolo J M, Kingman A, Russo A, et al. Kinetics of tempol for prevention of xerostomia following head and neck irradiation in a mouse model. Clinical cancer research: an official journal of the American Association for Cancer Research. 2005; 11(20):7564-8.
25. Morgan-Bathke M, Harris Z I, Arnett D G, Klein R R, Burd R, Ann D K, et al. The Rapalogue, CCI-779, improves salivary gland function following radiation. PloS one. 2014; 9(12):e113183.
26. Zeidan Y H, Xiao N, Cao H, Kong C, Le Q T, Sirjani D. Botulinum Toxin Confers Radioprotection in Murine Salivary Glands. International journal of radiation oncology, biology, physics. 2016; 94(5):1190-7.
27. Schmidt-Ullrich R K. Molecular targets in radiation oncology. Oncogene. 0000; 22(37):5730-3.
28. van Luijk P, Pringle S, Deasy J O, Moiseenko V V, Faber H, Hovan A, et al. Sparing the region of the salivary gland containing stem cells preserves saliva production after radiotherapy for head and neck cancer. Science translational medicine. 2015; 7(305):305ra147.
29. Pringle S, Van Os R, Coppes R P. Concise Review: Adult Salivary Gland Stem Cells and a Potential Therapy for Xerostomia. STEM CELLS. 2013; 31(4):613-9.
30. Sorokina L V, Solyanik G I, Pyatchanina T V. The evaluation of prooxidant and antioxidant state of two variants of lewis lung carcinoma: a comparative study. Experimental oncology. 2010; 32(4):249-53.
31. Kwei K A, Finch J S, Thompson E J, Bowden G T. Transcriptional repression of catalase in mouse skin tumor progression. Neoplasia. 2004; 6(5):440-8.
32. Jaramillo M C, Briehl M M, Batinic-Haberle I, Tome M E. Manganese (III) meso-tetrakis N-ethylpyridinium-2-yl porphyrin acts as a pro-oxidant to inhibit electron transport chain proteins, modulate bioenergetics, and enhance the response to chemotherapy in lymphoma cells. Free Radic Biol Med. 2015; 83:89-100.
33. Fujiwara N, Inoue J, Kawano T, Tanimoto K, Kozaki K, Inazawa J. miR-634 Activates the Mitochondrial Apoptosis Pathway and Enhances Chemotherapy-Induced Cytotoxicity. Cancer research. 2015; 75(18):3890-901.
34. Lomeli N, Di K, Czerniawski J, Guzowski J F, Bota D A. Cisplatin-induced mitochondrial dysfunction is associated with impaired cognitive function in rats. Free Radic Biol Med. 2017; 102:274-86.
35. Marullo R, Werner E, Degtyareva N, Moore B, Altavilla G, Ramalingam S S, et al. Cisplatin induces a mitochondrial-ROS response that contributes to cytotoxicity depending on mitochondrial redox status and bioenergetic functions. PloS one. 2013; 8(11):e81162.

36. Santos N A, Bezerra C S, Martins N M, Curti C, Bianchi M L, Santos A C. Hydroxyl radical scavenger ameliorates cisplatin-induced nephrotoxicity by preventing oxidative stress, redox state unbalance, impairment of energetic metabolism and apoptosis in rat kidney mitochondria. Cancer chemotherapy and pharmacology. 2008; 61(1): 145-55.

Example 2

This study involves escalating doses of BMX-001 with standard of care concurrent RT and cisplatin. Patients with biopsy-proven head and neck cancer (squamous cell carcinoma) undergo standard staging consisting of history and physical exam, contrast enhanced CT+/− PET scan and/or MRI, and QoL questionnaires. Intensity modulated radiotherapy (IMRT) is delivered with once daily 2.0-2.1 Gy fractions for definitive intent or adjuvant post-operative patients requiring chemo-radiation for high-risk disease including evidence of positive margins or extracapsular lymph node extension. Patients undergoing definitive intent IMRT receive 69.3-70 Gy in 33-35 fractions. Post-operative IMRT is delivered to a dose range of 60-66 Gy in 30-33 fractions.

Cisplatin is delivered per investigator choice, either 100 mg/m2 IV q21 days×2, 100 mg/m2 IV q21 days×3, or 30-40 mg/m2 IV weekly×6-7 doses. All of these dosing schedules are acceptable as standard of care per NCCN guidelines and utilized within NCI-sponsored cooperative groups. A minimum of 3 subjects and a maximum of 48 subjects with locally advanced head and neck cancers will be enrolled into this study during a 36-month period.

Phase 1a

A dose-escalation of BMX-001 conducted in combination with standard dose intensity modulated radiation therapy (IMRT) and concurrent cisplatin (CRT) to determine the Recommended Phase 2 Dose (RP2D) of BMX-001. The dose escalation is guided by a Continuous Reassessment Method (CRM) design. Patients with locally advanced (stage III-IVB) head and neck squamous cell carcinoma (HNSCC) for whom radiation plus cisplatin is appropriate are eligible as described below. Subjects are administered BMX-001 subcutaneously as a loading dose on day 4 to 0. Starting on day 1 or 2 of CRT patients will receive a maintenance dose (50% of loading dose) twice weekly administered on days of radiation therapy and for one week after radiation concludes. Cisplatin is administered per institution's standard of care practice. Common standard of care practice includes dosing cisplatin at 100 mg/m2 IV q21 days starting on Day 1 of RT for 2-3 doses or dosing cisplatin at 30-40 mg/m2 IV on Monday or Tuesday of each week of RT for 6-7 total doses. Patients receive a continuous course of IMRT delivered as single daily fractions of 2.0-2.1 Gy with a cumulative radiation dose between 60 Gy and 70 Gy depending on whether they have undergone resection or are receiving definitive radiation therapy. Planned radiation treatment volumes must include at least two oral sites (buccal mucosa, floor of mouth, oral tongue, soft palate, hard palate, retromolar trigone) with each site receiving a minimum total of 50 Gy.

Based on CRM design, cohorts of 3 subjects will accrue with dose escalation, beginning with 7 mg/subject, until the RP2D is defined. Following the treatment of 3 subjects or in the case of a dose-limiting toxicity, dose assignments for subsequent subjects and whether dose can continue to be escalated will be determined. If a subject terminates protocol treatment without experiencing a dose limiting toxicity (DLT) and before completing CRT and 4 weeks of follow up, the subject is not evaluable for the determination of DLT and is replaced. It is estimated that a maximum of 18 subjects are required for Phase 1a. The maximum tolerated dose (MTD) is the highest dose level at which the CRM model produces a DLT rate of 0.25. If no DLT has been identified at the highest dose proposed (loading dose of 42 mg/subject followed by 10 mg/subject twice per week) this is accepted as the RP2D and the dose to be used in Phase 1b.

In order to evaluate the pharmacokinetics (PK) of BMX-001, blood samples will be drawn for analysis.

Implementation of Phase 1a

Initial Design/Stage 1: This Phase 1 study ise conducted in two stages. In the first stage, cohorts of 3 patients are treated starting with dose level #1. Once 3 patients have been undergone treatment without experiencing DLT after a monitoring period of four weeks, the dose of the subsequent group of 3 patients is be escalated. This process continues until a patient experiences a DLT or the maximum proposed dose is reached without encountering a DLT.

Model-Based Escalation/Stage 2: Within stage 2, patients are accrued to the study in cohorts of 3 patients. Whenever the toxicity outcomes associated with patients within a cohort are known, the one-parameter logistic model is re-estimated by the study's statistical team using all available data. Based upon this re-estimated model, the dose level that results in a DLT rate nearest to the target DLT rate is determined and used to treat the next patient subject to a dose escalation restriction. That restriction requires that the dose for the next patient cannot be more than one level higher than that of the current patient.

Study Termination: A maximum of 18 patients evaluable for the determination of MTD will be accrued to the study. Though simulations demonstrating properties of this design assumed a fixed sample size, accrual termination will also be allowed once 6 or more consecutive patients have been treated at a dose level without any indication that the dose should be escalated or de-escalated.

The highest dose at which the DLT rate is no more than 0.25 based on CRM will be the maximum tolerated dose (MTD).

Phase 1b

After the maximum tolerated dose is determined, a maximum of 48 patients will be enrolled to this MTD dose level determined in Phase 1a to confirm the MTD.

Radiation Therapy

Note: for this study, IMRT or VMAT is mandatory. (Image-Guided Radiotherapy (IGRT) is required; however, margin reduction is not permitted even when IGRT is used)

Treatment plan should include a continuous course of IMRT delivered as single daily fractions of 2.0 to 2.1 Gy with a cumulative radiation dose between 60 Gy and 70 Gy. Planned radiation treatment volumes must include at least two oral mucosal sub-sites (buccal mucosa, retromolar trigone, floor of mouth, tongue, soft palate, hard palate) with a portion of each site receiving at least 50 Gy.

For post-operative irradiation, the standard of care is that radiation therapy will not be initiated until good wound healing has been achieved and will be initiated no earlier than 28 days following surgical resection of the malignancy.

Dose Specification for Clinically Measurable Disease

IMRT will be delivered in 30-35 fractions over 6 weeks, 5 fractions weekly in one plan (SIB) or 35 fractions over 7 weeks, 5 fractions weekly using sequential plans. Concomitant boost using separate IMRT plans is not allowed.

For Patients Treated with SIB Technique

Missed treatments due to holidays or logistic reasons can be compensated for by delivering an additional BID treatment during the week, OR treating on the Saturday or Sunday of that week, OR adding to the end of treatment.

The primary tumor and involved nodes (CTV1) will typically consist of a 0.5-1.5 cm expansion of the gross tumor volume (GTV) to cover potential local invasion and will be prescribed 2 Gy/fraction, total 70 Gy.

High-risk sub-clinical disease sites, which include possible local subclinical infiltration at the primary site (primary site CTV2) and first echelon nodes, which are not clinically or radiographically involved (nodal CTV2), should be expanded by 3-5 mm to create PTV2. PTV2 should receive 1.6 Gy/fraction to a total dose of 56 Gy.

Lower-risk targets (PTV3) (such as neck nodal levels which are not first echelon nodes and are not adjacent to levels containing grossly involved nodes) are prescribed 50-52.5 Gy (at 1.43-1.5 Gy/fraction, BED2=approximately 40-45 Gy).

Non-uniform or larger expansions to encompass high-risk anatomical compartments may be necessary.

Either of two options is acceptable for treatment of the low neck. One option is to treat with isocentric matching AP or AP-PA fields with larynx block, matched to the inferior margin of the IMRT portals just above the arytenoids. The dose is 2 Gy per fraction prescribed to 3 cm depth to a total dose of 44 Gy in 22 daily fractions. Whole-neck IMRT is also allowed as an alternative approach. Involved low neck nodes are to receive at least 60 Gy in 30 fractions. This can be achieved by either boosting the low neck field with an additional 16 Gy in 8 fractions, by an AP or AP-PA fields, or by planning the whole neck using IMRT. In cases of gross involvement of the vallecula or low neck, whole-neck IMRT should be considered. Whole-neck IMRT may be preferable if level VI is considered to be at risk due to gross involvement of level IV nodes.

For Patients Treated with Sequential Plans Technique

Missed treatments due to holidays or logistic reasons can be compensated for by delivering an additional BID treatment during the week, OR treating on the Saturday or Sunday of that week, OR adding to the end of treatment.

The primary tumor and involved nodes (CTV1) typically consist of a 0.5-1.5 cm expansion of the gross tumor volume (GTV) to cover potential local invasion and will be prescribed 2 Gy/fraction, total 70 Gy. Non-uniform or larger expansions to encompass high-risk anatomical compartments may be necessary.

High-risk subclinical disease sites, which include possible local subclinical infiltration at the primary site (primary site CTV2) and first echelon nodes, which are not clinically or radiographically involved (nodal CTV2), should be expanded by 3-5 mm to create PTV2. PTV2 should receive 2 Gy/fraction to a total dose of 60 Gy.

Lower-risk targets (PTV3) (such as neck nodal levels which are not first echelon nodes and are not adjacent to levels containing grossly involved nodes) should receive 44 Gy in 2 Gy fractions.

Either of two options is acceptable for treatment of the low neck. One option is to treat with isocentric matching AP or AP-PA fields with larynx block, matched to the inferior margin of the IMRT portals just above the arytenoids. The dose is 2 Gy per fraction prescribed to 3 cm depth to a total dose of 44 Gy in 22 daily fractions. Whole-neck IMRT is also allowed as an alternative approach. Involved low neck nodes receive at least 60 Gy in 30 fractions. This can be achieved by either boosting the low neck field with an additional 16 Gy in 8 fractions, by an AP or AP-PA fields, or by planning the whole neck using IMRT. In cases of gross involvement of the vallecula or low neck, whole-neck IMRT should be considered. Whole-neck IMRT may be preferable if level VI is considered to be at risk due to gross involvement of level IV nodes.

All plans must be normalized such that 95% of the volume of the PTV1 is covered with prescription dose of 70 Gy. Additionally:

At 1 cc PTV1 volume on the DVH curve, the dose should not be >110% of the prescribed dose.

At a volume of 0.03 cc within the PTV1 volume on the DVH curve, the dose should not be <95% of the prescribed dose.

For any volume of tissue outside the PTVs that has a size of 1 cc, the dose should not be >74 Gy for definitive radiation.

For Resected Patients the prescribed radiotherapy dose will be 60-66 Gy in 2 Gy once-daily fraction size (total of 30-33 fractions) The daily dose of 2 Gy will be prescribed such that 95% of the PTV60 volume receives at least 60 Gy. PTV56 is also used, and PTV66 (given as an integrated boost) may be optionally defined. Three-dimensional conformal radiotherapy followed by a 6 Gy boost is not permitted.

Study Drug (Cisplatin)

Refer to the package insert for detailed pharmacologic and safety information

Description

Cisplatin is a standard of care chemotherapeutic agent used to treat a myriad of malignancies, including HNSCC and salivary gland cancers. It works by binding DNA and causing crosslinks and adducts.

Formulation

Each vial contains 10 mg of cisplatin (DDP), 19 mg of sodium chloride, 100 mg of mannitol, and hydrochloric acid for pH adjustment. One vial is reconstituted with 10 mL of sterile water. The pH range will be 3.5 to 4.5. Cisplatin injection also is available from the manufacturer in aqueous solution, each mL containing 1 mg cisplatin and 9 mg NaCl and HCL or NaOH to adjust pH.

Storage and Stability

Reconstituted solution of cisplatin is stable for 20 hours when stored at 27° C. and should be protected from light if not used within 6 hours. The vials and injection should not be refrigerated. Cisplatin has been shown to react with aluminum needles, producing a black precipitate within 30 minutes.

Administration

Cisplatin is an IV chemotherapeutic agent approved to treat head and neck cancers. Cisplatin will be administered per institution's standard of care practice. Common standard of care practice includes dosing cisplatin at 100 mg/m2 IV q21 days starting on Day 1 of RT for 2-3 doses or dosing cisplatin at 30-40 mg/m2 IV on Monday or Tuesday of each week of RT for 6-7 total doses. Cisplatin will be infused per institutional guidelines. Patients who start on q21 day dosing may switch to weekly dosing if deemed necessary by the treating investigator. Per institutional guidelines, patients should receive vigorous hydration and electrolyte replacement. The use of prophylactic anti-emetics including a 5-HT3 inhibitor and dexamethasone is required per ASCO Guidelines. A NK1 inhibitor such as aprepitant may be used per institutional guidelines.

Dose Modifications

Dose modifications of cisplatin will be performed by the treating physician per each institution's standard practice.

The following are guidelines to aid indecision-making. Escalation of the cisplatin is not allowed once the dose level has been reduced.

Suggested dose modifications

| Starting dose | Dose level-1 | Dose level-2 |
|---|---|---|
| 40 mg/m² (weekly) | 30 mg/m² (weekly) | 20 mg/m² (weekly) |
| 30 mg/m² (weekly) | 20 mg/m² (weekly) | Discontinue cisplatin |
| 100 mg/m² (q21 days) | 75 mg/m² (q21 days) | 50 mg/m² (q21 days) |

Hematologic Toxicity

| NCI CTCAE Toxicity Grade (v 4.03) | Cisplatin dose at start of subsequent week |
|---|---|
| Neutropenia | |
| 1 (1500-1999/mm³) | Maintain dose level |
| 2 (1000-1499/mm³) | Maintain dose level |
| 3 (500-999/mm³) | Hold dose for one week; if continues >7 days then decrease 1 dose level and resume when reaches grade 2. |
| 4 (<500/mm³) | Hold dose for one week; if continues >7 days then decrease 1 dose level and resume when reaches grade 2. |
| Neutropenic Fever (grade 3 or 4) | Hold dose at least one week; if ANC ≥1500 then decrease 1 dose level. |
| Thrombocytopenia | |
| 1 (75,000/mm³-LLN) | Maintain dose level |
| 2 (50,000-74,999/mm³) | Hold dose for one week; if continues >7 days then decrease 1 dose level and resume when reaches grade 1 |
| 3 (25,000-49,999/mm³) | Hold dose for one week; if continues >7 days then decrease 1 dose level and resume when reaches grade 1 |
| 4 (<25,000/mm³) | Hold dose for one week; if continues >7 days then decrease 1 dose level and resume when reaches grade 1 |

Non-hematologic Toxicity

| NCI CTCAE Toxicity Grade (v 4.03) | Cisplatin dose at start of subsequent week |
|---|---|
| Renal-serum creatinine | |
| Cr ULN-1.5 mg/dL or CrCl >50 mL/min | Maintain dose level |
| >1.5 mg/dL and CrCl 40-50 mL/min | Decrease by 1 dose level |
| Cr >1.5 mg/dL and CrCl <40 | Hold drug until CrCl is >50 mL/min the resume after decrease by 1 dose level |
| Fatigue Grade 3 | Decrease by 1 dose level |
| Nausea/vomiting | |
| ≤Grade 2 with maximal medical management | Maintain dose level |
| Intolerable grade 2 with maximal medical management | Decrease by 1 dose level |
| ≥Grade 3 with maximal medical management | Hold drug until ≤ grade 2 then resume at one lower dose level |
| Mucositis in RT field Grade 4 | Hold drug until ≤ grade 3 |
| Hearing impairment or tinnitus | |
| ≤Grade 1 | Maintain current dose |
| Grade 2 | Decrease dose by one dose level |
| Grade 3 | Hold drug until ≤ grade 1 then resume at one lower dose level |
| Grade 4 (hearing impairment) | Discontinue cisplatin |
| Other grade 4 non-hematologic AEs | Hold drug until ≤ grade 1 then resume at one lower dose level |

Study Drug (BMX-001)
Names, Classification, and Mechanism of Action

BMX-001, also known as MnTnBuOE-2-PyP5+(manganese butoxyethyl pyridyl porphyrin), is a metalloporphyrin antioxidant that has anti-inflammatory, anti-oxidant, and anti-tumor functions. A series of metalloporphyrins have undergone preclinical evaluation, and BMX-001 represents one with increased catalytic potency along with comparatively high lipophilicity, sufficient to permit distribution across the blood-brain barrier and accumulation in the brain parenchyma at therapeutic concentrations. This class of metalloporphyrins leads to inactivation of reactive oxygen species and in turn leads to reduction of oxidative stress. Because the vasculature of most mammalian species is highly sensitive to an oxidative shift, there is a concern for blood pressure monitoring in studies of the metalloporphyrin compounds. Studies in Sprague-Dawley rats showed that intravenous delivery of metalloporphyrin could lead to transient hypotension. In this same study, mice, guinea pigs, dogs, and baboons received intravenous delivery of metalloporphyrins with less effect on blood pressure.

Drug Product Formulation and Manufacture

The drug is supplied by BioMimetix JV, LLC. The drug substance (1.2 kg of solid) was manufactured and stored according to cGMP by Albany Molecular Research, Inc. (AMRI).

BioMimetix JV, LLC, has contracted with AMRI (Glasgow) Ltd. to manufacture single dose vials of sterile BMX-001 for injection. Manufacturing will be conducted on AMRI's Flexicon FPC50W filling machine, which is dedicated for aseptic GMP manufacturing within a clean room suite. Manufacturing will include batch pre-filtration and aseptic filtration and filling in accordance with AMRI Glasgow's validated process.

BMX-001 is formulated as a solution in 0.9% saline at 10 mg/mL, aseptically filtered and filled to 2 mL in a 5 mL Type 1 clear glass vial, sealed with a 20 mm Flurotec serum stopper and flip off aluminum overseal. A nitrogen overlay will be applied to each vial following filling and prior to stoppering.

In-process testing includes pre-filtration bioburden, post-use filter integrity test, and in-process weight checking. Release tests and specifications for BMX-001 for injection are established before manufacturing of the clinical batch commences. These include sterility (USP <71>), bacterial endotoxins (USP <85>), particulate matter (USP <788>), appearance, color and clarity, pH, osmolality, assay, and purity.

The clinical batch of drug product is placed on stability and tested for the duration of its use during the clinical trials.

Syringe and Label for Administration of BMX-001 for Injection, 10 mg/mL

A pharmacist at the clinical study center prepares the loaded syringe(s) and needle(s) that are used for subcutaneous administration of the appropriate dose of BMX-001 for injection, 10 mg/mL to the clinical subject. The clinical study center pharmacist adheres to all USP 797 standards for preparation of sterile products. This preparation is performed in a class II Biologic Safety Cabinet (BSC) located in a USP 797 compliant cleanroom. Cleaning of the BSC and cleanroom is performed as required by USP 797 guidelines. The entire pharmacy staff is USP 797 trained and tested and maintains annual compliance. The subcutaneous needle is capped and the syringe is stored at room temperature until use, which occurs within 2 hours. A barcode label is applied to the syringe and linked to the electronic medical record system of the clinic.

Administration by Dose Escalation and Expansion for BMX-001

BMX-001 is be administered subcutaneously as a loading dose before starting concurrent chemoradiation (days −4 through 0 depending on patient scheduling). After the loading dose, the maintenance dose levels is given two times per week for 8 weeks. The starting dose level is 7 mg loading dose. BMX-001 dose escalation will be 7 mg loading dose, 14 mg loading dose, 28 mg loading dose, and 42 mg loading dose in four dose levels. After the loading dose, the BMX-001 maintenance dose is administered at the amounts listed below twice a week (see the Dosing Levels Table below). The corresponding volumes of BMX-001, Injection Solution 10 mg/mL associated with the loading doses are as follows:

0.7 mL/subject loading dose=7 mg/subject
1.4 mL/subject loading dose=14 mg/subject
2.8 mL/subject loading dose=28 mg/subject
4.2 mL/subject loading dose=42 mg/subject The corresponding maintenance doses would be equivalent to the following:

0.35 mL/subject maintenance dose=3.5 mg/subject
0.7 mL/subject maintenance dose=7 mg/subject
1.4 mL/subject maintenance dose=14 mg/subject
2 mL/subject maintenance dose=20 mg/subject No more than 1.4 mL is to be administered at a single injection site. Thus a 28 mg or 20 mg dose is administered in two equal portions (14 mg or 10 mg, respectively), taken from different vials and injected via separate syringes and needles at two different sites. A 42 mg dose is administered in three 14 mg portions taken from three different vials and injected via separate syringes and needles at three different sites.

BMX-001 is administered by subcutaneous injection of a sterile 10 mg/mL solution in saline. The subcutaneous injections may be at any optimum site on the torso, the upper leg or upper arm. Maintenance doses will be approximately one-half the size of the loading dose and should be administered twice weekly. The first maintenance dose should be delivered either 3 or 4 days after the loading dose and subsequent maintenance doses delivered at 3 to 4 day intervals to average 2 doses per week.

TABLE 4

Dosing Levels for Groups I through IV

|  | Group I | Group II | Group III | Group IV |
|---|---|---|---|---|
|  |  | Loading Dose |  |  |
| Maintenance Dose | 7 mg/Subject | 14 mg/Subject | 28 mg/Subject | 42 mg/Subject |
| 1 | 3.5 mg | 7 mg | 14 mg | 20 mg |
| 2 | 3.5 mg | 7 mg | 14 mg | 20 mg |
| 3 | 3.5 mg | 7 mg | 14 mg | 20 mg |
| 4 | 3.5 mg | 7 mg | 14 mg | 20 mg |
| 5 | 3.5 mg | 7 mg | 14 mg | 20 mg |
| 6 | 3.5 mg | 7 mg | 14 mg | 20 mg |
| 7 | 3.5 mg | 7 mg | 14 mg | 20 mg |
| 8 | 3.5 mg | 7 mg | 14 mg | 20 mg |

Treatment Period

The treatment period consists of 6-7 weeks of concurrent RT and chemotherapy with BMX-001 followed by 1 week of BMX-001.

Physical examinations, vital signs (temperature, respiratory rate, blood pressure, and pulse), height (screening or baseline only), and weight must be performed at:
screening
baseline
every week from weeks 1-8
at SOC visits after completing RT for a period of 1 year
More frequent examinations may be performed.

Example 3

This is a Phase 1/2 study of BMX-001 in combination with standard radiation therapy (RT) and temozolomide (TMZ) in the treatment of newly diagnosed high grade glioma (HGG) patients.

Phase 1

Primary Objective

To determine the maximum tolerated dose (MTD) of BMX-001 in combination with standard RT and TMZ in newly diagnosed HGG patients.

Secondary Objectives

To assess the safety and tolerability of BMX-001 in combination with standard RT and TMZ in newly diagnosed HGG patients. To assess the efficacy of BMX-001 in combination with standard RT and TMZ in newly diagnosed HGG patients based upon overall survival (OS) and progression free survival (PFS). To examine the impact on cognition of BMX-001 in combination with standard RT and TMZ in treatment of newly diagnosed HGG patients. To describe radiographic response in newly diagnosed HGG patients treated with BMX-001 in combination with standard RT and TMZ. To characterize the pharmacokinetic profile of BMX-001 when delivered in combination with RT and TMZ in newly diagnosed HGG patients.

Exploratory Objectives

To describe patient-reported outcomes of health-related quality of life (HRQoL) in newly diagnosed HGG patients treated with BMX-001 in combination with standard RT and TMZ. To describe changes in hair loss during BMX-001 in combination with standard RT and TMZ in newly diagnosed HGG patients.

Phase 2

Primary Objective

To assess the effect on overall survival (OS) of standard RT and TMZ in combination with BMX-001 compared to standard RT and TMZ alone in newly diagnosed HGG patients.

Secondary Objectives

To assess the impact on cognition of standard RT and TMZ in combination with BMX-001 compared to standard RT and TMZ alone in newly diagnosed HGG patients. To assess the safety and tolerability of standard RT and TMZ in combination with BMX-001 compared to standard RT and TMZ alone in newly diagnosed HGG patients. To assess the effect on progression-free survival (PFS) of standard RT and TMZ in combination with BMX-001 compared to standard RT and TMZ alone in newly diagnosed HGG patients. To assess radiographic response in newly diagnosed HGG patients treated with standard RT and TMZ in combination with BMX-001 compared to standard RT and TMZ alone. To characterize the repeated-dose pharmacokinetic profile of BMX-001 when delivered in combination with RT and TMZ in newly diagnosed HGG patients.

Exploratory Objectives

To describe patient-reported outcomes of HRQoL in newly diagnosed HGG patients treated with standard RT and TMZ in combination with BMX-001 compared to standard RT and TMZ alone. To describe changes in hair loss in newly diagnosed HGG patients treated with standard RT and TMZ in combination with BMX-001 compared to standard RT and TMZ alone. To describe change in white matter integrity in newly diagnosed HGG patients treated with standard RT and TMZ in combination with BMX-001 in comparison to standard RT and TMZ alone.

Design and Procedure

Phase 1

Phase 1 component of this protocol is a dose-escalation study of the combination of BMX-001 with standard dosing of daily TMZ and RT in patients with newly diagnosed HGG (WHO grade III or IV). The dose escalation is guided by a CRM design to determine the MTD of BMX-001 in combination with concurrent daily TMZ and RT. Subjects are administered BMX-001 subcutaneously first as a loading dose given 0 to 4 days before the start of chemoradiation and then at a subsequent dose (50% of the loading dose) twice a week for eight weeks. There are only be two doses per week regardless of whether the dose is a loading or maintenance dose. TMZ will be dosed at 75 mg/m$^2$ orally daily for 42 days and RT is delivered in daily fractions of 1.8-2 Gy given 5 days a week for 6 weeks for a total of 59-60 Gy.

Cohorts of 3 subjects will be accrued and treated until the MTD is defined. Following the treatment of the first 3 subjects at the initial dose level of 0.1 mg/kg dose level, dose assignments for subsequent subjects and whether dose can be escalated will be determined. If a subject terminates protocol treatment without experiencing a DLT and before completing standard chemoradiation, then the subject will not be evaluable for the determination of DLT and will be replaced.

It is estimated that a maximum of 18 subjects are required for Phase 1. The maximum tolerated dose (MTD), defined as the dose that has an estimated DLT rate nearest to 0.25, will be the dose used in the future Phase 2 study.

In order to evaluate the pharmacokinetics of BMX-001 in combination with current chemoradiation, blood samples are drawn for analysis. The first dose of BMX-001 is administered subcutaneously in the morning as a loading dose. Blood is drawn on the following days: loading dose day, Day 8 or the next date on which drug is administered, and Day 36 or the next date on which drug is administered. Measures are obtained at the following times: Predose, 0.5 hour, 1 hour, 2 hours, 6 hours, and 24 hours. Samples are analyzed for BMX-001 using validated analytical methods at a laboratory identified by the sponsor.

Phase 2

The Phase 2 portion of this study is a randomized study comparing concurrent daily TMZ and RT with BMX-001 (Arm A) versus concurrent daily TMZ and RT alone (Arm B) in patients with newly diagnosed HGG (WHO grade III and IV). The loading dose for Arm A will be determined based on findings from the Phase 1 component of this protocol. Since both toxicity and cognition are outcomes in Phase 1 study, we will use this information to choose the dose for evaluation in Phase 2. Subjects should be randomized with a treatment arm allocation ratio of 1:1 and there will be 48 patients enrolled in this phase of the study (24 subjects per arm). Subjects in Arm A should be administered BMX-001 subcutaneously first as a loading dose given 0 to 4 days before the start of chemoradiation and then at subsequent dose twice a week for eight weeks. Subjects in Arm A and Arm B will receive TMZ dosed at 75 mg/m$^2$ orally daily for 42 days and RT delivered in daily fractions of 1.8-2 Gy given 5 days a week for 6 weeks for a total of 59.4-60 Gy. Cognitive performance should be measured on the day of enrollment, 2 weeks after the completion of RT, and every standard of care (SOC) clinic visit (approximately every 8 weeks) until tumor progression, death, or patient's choice to discontinue study measures.

In order to provide characterization of the repeated dose pharmacokinetic profiles of BMX-001 in combination with RT and TMZ in newly diagnosed HGG patients, blood samples should be drawn from six patients in the Phase 2 portion of the study on Days 8 and 36 only. Measures should be obtained at the following times: Predose, 0.5 hour, 1 hour, 2 hours, 6 hours and 24 hours. Samples should be analyzed for BMX-001 using validated analytical.

Investigational Plan

Study Design

As this study is a Phase 1/2 study, this protocol includes a Phase 1 Dose Escalation portion and a randomized Phase 2 portion. In the Phase 1 Dose Escalation portion of the study, the dose of BMX-001 will be escalated, while the dose of daily TMZ and RT (chemoradiation phase) will remain fixed and will be followed by adjuvant TMZ (adjuvant phase). The randomized Phase 2 study component will assess the impact on cognition of BMX-001 in combination with daily TMZ and standard RT in comparison to daily TMZ and standard RT in newly diagnosed HGG patients.

Phase 1 Specific Design

This study will be a single-site study of escalating doses of BMX-001 in combination with RT and TMZ (chemoradiation phase), followed by adjuvant TMZ (adjuvant phase). In the chemoradiation phase, external beam RT therapy will be given over less than seven weeks in 30-33 fractions for a total dose of 59-60 Gy. TMZ (75 mg/m$^2$ po daily) will be started on the first day of RT and will be administered for 42 days. TMZ will be given before RT daily. Adjuvant TMZ therapy will begin 2 to 4 weeks after the completion of RT. Adjuvant TMZ could be administered for up to 12 scheduled 28-day cycles. TMZ will be given orally at night on days 1-5 of 28-day cycle. During the chemoradiation phase and 2 weeks thereafter, CBC with differential and a CMP will be obtained weekly. A minimum of 3 subjects and a maximum of 18 subjects with newly diagnosed HGG will be enrolled into this study during a 12-month period. We will aim to enroll 3 subjects every eight to ten weeks. Once 3 patients have undergone treatment without experiencing a DLT after a monitoring period of four weeks following completion of all doses of BMX-001, the dose of the subsequent group of 3 patients will be escalated.

Dose Escalation for BMX-001 in Phase 1

BMX-001 is be administered subcutaneously as a loading dose before starting concurrent chemoradiation (days −5 through 0 depending on patient/radiotherapy scheduling). After the loading dose, the dose levels will be given two times per week for 8 weeks. The starting dose level will be 7 mg loading dose. BMX-001 dose escalation will be 7 mg loading dose, 14 mg loading dose, 28 mg loading dose, and 42 mg loading dose in four dose levels. After the loading dose, the BMX-001 dose will be administered at the amounts listed below twice a week (see Table 5 below). The corresponding volumes of BMX-001, Injection Solution 10 mg/mL associated with the loading doses are as follows (the equivalent dose for a 70 kg adult is also given):

0.7 mL/subject loading dose=7 mg/subject and is equivalent to 0.1 mg/kg 1.4 mL/subject loading dose=14 mg/subject and is equivalent to 0.2 mg/kg 2.8 mL/subject loading dose=28 mg/subject and is equivalent to 0.4 mg/kg 4.2 mL/subject loading dose=42 mg/subject and is equivalent to 0.6 mg/kg The corresponding maintenance doses would be equivalent to the following:

0.35 mL/subject dose=3.5 mg/subject and is equivalent to 0.05 mg/kg 0.7 mL/subject dose=7 mg/subject and is equivalent to 0.1 mg/kg 1.4 mL/subject dose=14 mg/subject and is equivalent to 0.2 mg/kg 2 mL/subject dose=20 mg/subject and is equivalent to 0.3 mg/kg BMX-001 is administered by subcutaneous injection of a sterile 10 mg/mL solution in saline. Syringes will be either 1 mL or 3 mL with a 25 gauge X ⅝ inch needle depending on the volume of injection. The subcutaneous injections may be at any optimum site on the torso the upper leg or upper arm. Sites of injection should be alternated. Subsequent (maintenance) doses will be one-half the size of the loading dose (except Group IV where the subsequent dose is rounded down to 20 mg) and should be administered twice weekly. The first dose should be delivered 3 to 5 days after the loading dose and further doses delivered at 3 to 4 day intervals to average 2 doses per week. BMX-001 will be delivered within 12 hours before or after RT. Schedule of subsequent doses will be dependent on the day of the loading dose and radiation schedule.

TABLE 5

Loading Doses and Subsequent Doses for BMX-001 in Phase 1 Study

| Week | Subject Group | | | |
|---|---|---|---|---|
| | I | II | III | IV |
| | Loading Dose[1] | | | |
| | 7 mg | 14 mg | 28 mg | 42 mg |
| | Subsequent Doses[1] | | | |
| 1 | 3.5 mg b.i.w. | 7 mg b.i.w. | 14 mg b.i.w. | 20 mg b.i.w. |
| 2 | 3.5 mg b.i.w. | 7 mg b.i.w. | 14 mg b.i.w. | 20 mg b.i.w. |
| 3 | 3.5 mg b.i.w. | 7 mg b.i.w. | 14 mg b.i.w. | 20 mg b.i.w. |
| 4 | 3.5 mg b.i.w. | 7 mg b.i.w. | 14 mg b.i.w. | 20 mg b.i.w. |
| 5 | 3.5 mg b.i.w. | 7 mg b.i.w. | 14 mg b.i.w. | 20 mg b.i.w. |
| 6 | 3.5 mg b.i.w. | 7 mg b.i.w. | 14 mg b.i.w. | 20 mg b.i.w. |
| 7 | 3.5 mg b.i.w. | 7 mg b.i.w. | 14 mg b.i.w. | 20 mg b.i.w. |
| 8 | 3.5 mg b.i.w. | 7 mg b.i.w. | 14 mg b.i.w. | 20 mg b.i.w. |

[1]Dose of BMX-001 for Injection, 10 mg/mL administered to subject.

Phase 2 Specific Design

The Phase 2 portion of this study is a randomized screening study comparing Arms A and B. Arm A will consist of daily TMZ and RT with BMX-001 and Arm B includes daily TMZ and RT alone.

For the Phase 2 Study, BMX-001 are administered subcutaneously as a loading dose before starting concurrent chemoradiation (days −5 through 0 depending on patient/MRI scheduling). After the loading dose, the subsequent doses are given two times per week for 8 weeks. Patients are randomized with a treatment arm allocation ratio of 1:1 to receive BMX-001 or to proceed with RT and TMZ alone. There are 48 patients enrolled in this phase of the study (24 subjects per arm). The BMX-001 loading doses are determined from Phase 1. Since both toxicity and cognition are outcomes in Phase 1, this information to choose the dose for evaluation in Phase 2. This will be done with involvement from BioMimetix JV, LLC and our biostatisticians. After the loading dose, BMX-001 will be administered at the subsequent doses listed in Table 5 that correspond to the BMX-001 loading dose.

BMX-001 is administered by subcutaneous injection of a sterile 10 mg/mL solution in saline. The subcutaneous injections may be at any optimum site on the torso, the upper leg or upper arm. The first subsequent dose should be delivered 1 to 5 days after the loading dose and subsequent doses delivered at 3 to 4 day intervals to average 2 doses per week.

Temozolomide (TMZ) Treatment Plan

TMZ is an oral alkylating agent which has demonstrated anti-tumor activity as a single agent in the treatment of recurrent glioma. As stated previously, Stupp et al have demonstrated an increase in efficacy of TMZ in combination with RT in the adjuvant treatment of primary malignant gliomas. In addition, the regimen was considered safe. Non-hematological grade 2 toxicities included: Fatigue (26%), other constitutional symptoms (7%), rash and dermatologic side effects (9%), infection (1%), vision (14%), and nausea and vomiting (13%). Grade 3/4 non-hematological toxicities occurred <10%: Fatigue (7%), other constitutional symptoms (2%), rash and dermatologic side effects (1%), infection (3%), vision (1%), and nausea and vomiting with a $5HT_3$-RA (<1%). Thus, this safe and standard regimen will be utilized in this protocol. During the chemoradiation phase, daily TMZ therapy is calculated at a dose of 75 mg per square meter of body surface area per day and be administered 7 days a week from the first until the last day of RT therapy or a total of 42 days. Weekly CBC with differential and monthly CMP will be obtained per standard of care. Additional clinical and laboratory assessments will be at the discretion of the RT therapist. During the adjuvant phase, 5-day TMZ therapy is calculated at a dose of 150 or 200 mg/m$^2$ and be administered the first 5 days of a 28 day cycle. One cycle consists of 28 days. During the adjuvant phase, CBC with differential should be obtained approximately on days 21 and 28 and CMP approximately on day 21.

Radiation Treatment Plan

As detailed by the Stupp regimen, RT therapy will be administered as fractionated focal irradiation in daily fractions of 1.8-2 Gy given 5 days a week for 6 weeks for a total of 5960 Gy. The RT therapist and oncologist should conduct the standard physical exams and obtain the lab work necessary for the eligibility. Additional clinical and laboratory assessments should be at the discretion of the RT therapist and oncologist.

Dose Definition and Schedule

The external beam RT therapy (RT) plan should be determined at the discretion of the local RT therapist dependent on tumor size and location. It should begin 2-12 weeks after surgery. One treatment of 1.8-2.0 Gy will be given daily, 5 days per week, (30-33 fractions over less than seven weeks) for a total of 59-60 Gy. All portals shall be treated during each treatment session. Doses are prescribed at the maximum dose line encompassing ≥95% of the target volume.

Treatment shall be delivered on megavoltage machines of energy ranging from 4 to 18 MV photons. Selection of the appropriate photon energy(ies) should be based on optimizing the RT dose distribution within the target volume and minimizing dose to non-target normal tissue. Photon energies >10 MV should be utilized only in dual energy beam arrangements using at least one beam with energy <10 MV. Source skin distance for SSD techniques or source axis distance for SAD techniques must be at least 80 cm.

Localization, Simulation, and Immobilization

The patient shall be treated in the supine or another appropriate position for the location of the lesion. A head-holding device that is transparent to x-rays and provides adequate immobilization must be utilized at all times during planning and therapy to ensure reproducibility.

The initial target volume shall include the contrast-enhancing lesion and surrounding edema (if it exists) demonstrated on the pre-operative MRI plus a 2.0-cm margin. If no surrounding edema is present, the initial target volume should include the contrast-enhancing lesion plus a 2.5-cm margin. This primary target volume is treated to 45-46 Gy in 23-25 daily fractions, at 1.8-2.0 Gy per fraction.

The boost volume should be based on the post-operative MRI performed during treatment planning. After 45-46 Gy, the boost volume must include the contrast-enhancing lesion plus a 1.5-cm margin or, if minimal contrast-enhancing lesion is present at a portion of the resection cavity on MRI, the surgical defect plus a 2.0-cm margin, whichever is greater at that segment of the MRI image. The boost volume should be treated to an additional 14-14.4 Gy in 7-8 daily fractions, 1.8-2.0 Gy per fraction. This brings the total target dose to 59-60 Gy in 30-33 fractions. All parts of the target volumes are to receive at least 100% but no more than 110% of the dose at the prescription isodose line.

Study Drug (BMX-001)

Drug Product Formulation and Manufacture

The drug is supplied by BioMimetix JV, LLC. The drug substance (1.2 kg of solid) was manufactured and stored according to cGMP by Albany Molecular Research, Inc. (AMRI).

BioMimetix has contracted with AMRI (Glasgow) Ltd. to manufacture single dose vials of sterile BMX-001 for injection. Manufacturing is conducted on AMRI's Flexicon FPC50W filling machine, which is dedicated for aseptic GMP manufacturing within a clean room suite. Manufacturing includes batch pre-filtration and aseptic filtration and filling in accordance with AMRI Glasgow's validated process.

BMX-001 will be formulated as a solution in 0.9% saline at 10 mg/mL, aseptically filtered and filled to 2 mL in a 5 mL Type 1 clear glass vial, sealed with a 20 mm Flurotec serum stopper and flip off aluminum overseal. A nitrogen overlay is applied to each vial following filling and prior to stoppering.

In-process testing includes pre-filtration bioburden, post-use filter integrity test, and in-process weight checking. Release tests and specifications for BMX-001 for injection are currently under development, but are established before manufacturing of the clinical batch commences. These include sterility (USP <71>), bacterial endotoxins (USP <85>), particulate matter (USP <788>), appearance, color and clarity, pH, osmolality, assay and purity.

The clinical batch of drug product is placed on stability and tested for the duration of its use during the clinical trials. Syringe and Label for Administration of BMX-001 for Injection, 10 mg/mL A pharmacist at ICS prepares the loaded syringe(s) and needle(s) that is to be used for subcutaneous administration of the appropriate dose of BMX-001 for Injection, 10 mg/mL from Table 5 to the clinical subject. ICS strictly adheres to all USP 797 standards for preparation of sterile products. This preparation will be performed in a class II Biologic Safety Cabinet (BSC) located in a USP 797 compliant cleanroom. Cleaning of the BSC and cleanroom is performed as required by USP 797 guidelines. The entire pharmacy staff are USP 797 trained, tested, and maintain annual compliance. The subcutaneous needle is capped and the syringe is stored at room temperature until use, which will occur within 2 hours. A barcode label is applied to the syringe and linked to the electronic medical record system of the clinic.

Multi-Dose Kits

No more than 1.4 mL is to be administered at a single injection site. Thus a 28 mg or 20 mg dose will be administered in two equal portions (14 mg or 10 mg, respectively), taken from different vials and injected via separate syringes and needles at two different sites. A 42 mg dose will be administered in three 14 mg portions taken from three different vials and injected via separate syringes and needles at three different sites.

A multi-dose kit for a clinical subject in Group I or II will include seventeen vials, one for each day of dosing, containing 20 mg (2 mL) of BMX-001 for Injection, 10 mg/mL. The only difference between the kits provided for Groups I and II will be in their labeling, which will indicate the appropriate doses to be administered as the loading and subsequent (maintenance) doses according to Table 5.

A multi-dose kit for a clinical subject in Group III will include 18 vials, including two for the loading dose and sixteen for the maintenance doses. A multi-dose kit for a clinical subject in Group IV will include 35 vials, including three for the loading dose and thirty-two for the maintenance doses. Labeling for these kits will indicate the appropriate doses to be administered as the loading and maintenance doses according to Table 5.

The dosing plan for stage two of the Phase 1 trial will be decided on the basis of the results from stage one. Dosing kits will be prepared as described above, with appropriate labeling to indicate the doses to be administered.

Each multi-dose kit comprises a paperboard box containing the appropriate number (17, 17, 18 or 35 for Group I, II, III or IV, respectively) of single dose vials of BMX-001 for Injection, 10 mg/mL.

Study Drug (Tmz)

Description

8-Carbamoyl-3-methylimidazol[5,1-d]-1,2,3,5-tetrazine-4-(3H)-one, CCRG 81045, M&B 39831)-Temozolomide is commercially available and not provided in this study.

Formulation

TMZ is available in 250 mg, 180 mg, 140 mg, 100 mg, 20 mg, and 5 mg strengths. Refer to package insert for contents of the formulation.

Storage

TMZ capsules should be stored between 2° C. to 30° C. Commercial supply and packaging will be used.

Administration

TMZ is administered orally on an empty stomach. The drug is approximately 100% bioavailable. The dose should be rounded to the nearest 5 mg. Effects of food on product absorption are not yet known. DO NOT OPEN CAPSULES. DO NOT MIX WITH FOOD. DO NOT CHEW CAPSULES.

TMZ at a dose of 75 mg/m² po daily will be started with external beam RT (+/−5 days). TMZ will be held for grade 3 thrombocytopenia, grade 4 neutropenia, or grade 4 non-hematologic toxicity secondary to TMZ. TMZ will be re-started at 50 mg/m² after resolution of the toxicity, or ≤grade 1. If the grade 3 thrombocytopenia, grade 4 neutropenia, or grade 4 non-hematologic toxicity secondary to TMZ recurs at 50 mg/m², TMZ will be held during RT therapy, but may resume after RT therapy if the patient meets the treatment criteria.

Example 4

A human study of BMX-001 in newly diagnosed high-grade glioma was designed to evaluate the safety of BMX-001 when given in combination with the standard of care regimen of concurrent temozolomide with radiation therapy (as described in Example 3) followed by adjuvant temozolomide. BMX-001 was delivered via injection as a loading dose and subsequently maintenance doses for eight weeks (6 weeks during concurrent chemoradiation and 2 weeks after chemoradiation) for a total of 17 doses. Four different loading doses were tested, which were: 7, 14, 28 and 42 mg, and the maintenance doses were half of the respective loading dose. The loading dose was administered prior to chemoradiation, and for the duration of treatment the respective maintenance doses were administered twice a week (i.e., a patient administered a 7 mg loading dose received two separate maintenance doses of 3.5 mg each week for 8 weeks.) The primary focus of this study is to determine the maximum tolerated dose of four dose levels. To date, we have treated nine subjects with three subjects each for the first three dose levels. All subjects have a diagnosis of glioblastoma (WHO grade IV) and mean age is 62.7 years (range 54 years to 80 years).

Protection of Cognitive Function During Radiation Therapy

Figure 7:
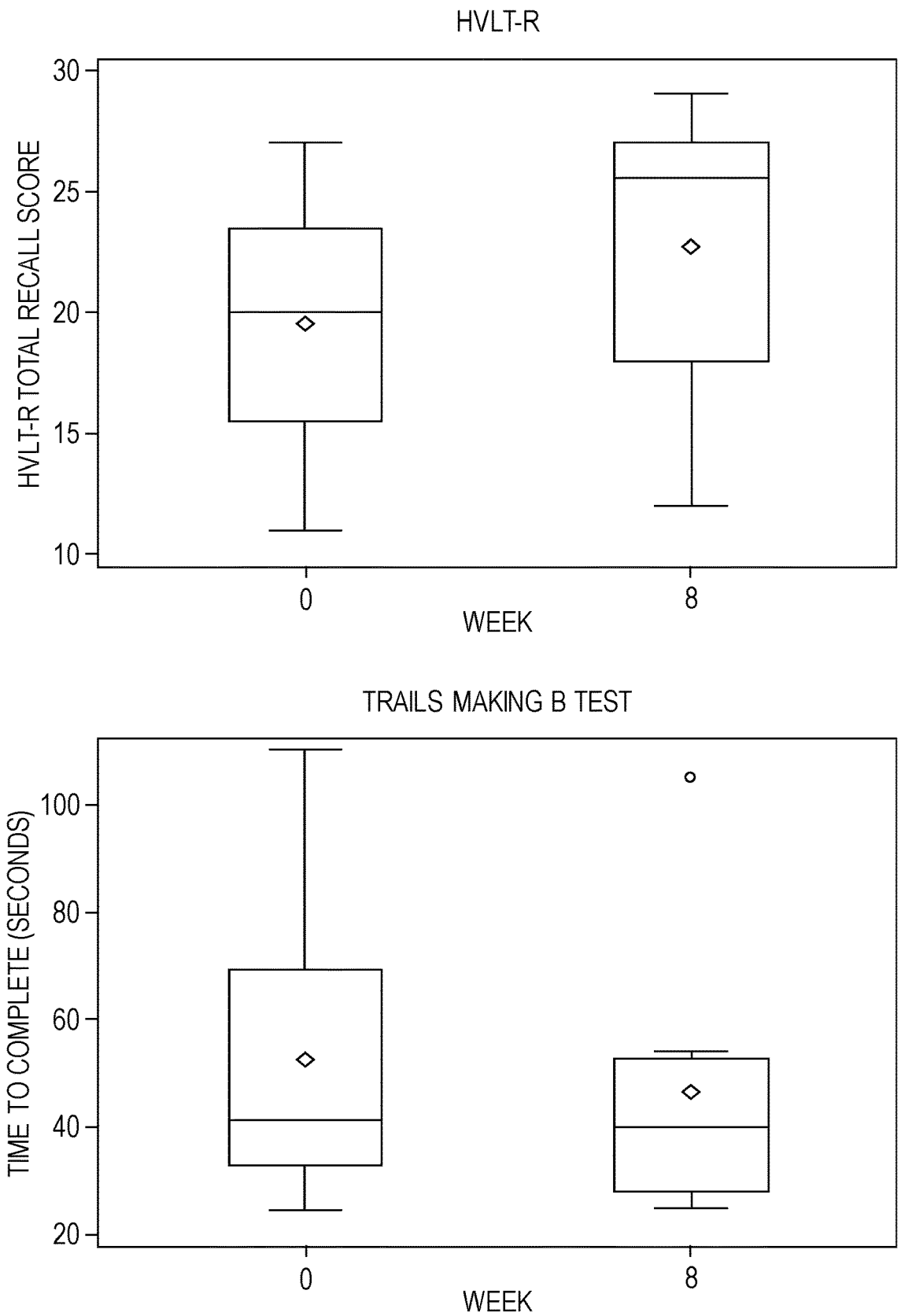
FIG. 7 shows graphs demonstrating the benefit of treatment with BMX-001 in subjects with high-grade glioma undergoing chemoradiation. Performance on cognitive testing in the first eight subjects in a phase 1 study of newly diagnosed high-grade glioma utilizing BMX-001 in combination with concurrent chemoradiation. Hopkins Verbal Learning Test-Revised (HVLT-R) (left panel) was performed at time 0 and after 8 weeks of chemoradiation therapy (higher scores=better performance). Trails Making B Test (right panel) was also performed at time 0 and after 8 weeks of chemoradiation therapy (faster/shorter times=better performance). Historical controls are extensively documented in the published literature. Patients receiving chemotherapy and radiation therapy for high-grade glioma would be expected to show a decline in cognitive function, often greater than of 30% after 8 weeks. These results demonstrate that there was no measurable decline in cognitive function after 8 weeks of chemoradiation therapy compared to the patients' status at time 0 (prior to chemoradiation therapy).

Of the nine subjects treated, eight subjects have completed quality of life evaluations and cognitive evaluations for the time points before concurrent chemoradiation and after concurrent chemoradiation. Cognitive testing included Hopkins Verbal Learning Test-Revised (HVLT-R), Trails Making A and B Tests, and Controlled Oral Wood Association Test (COWA). The findings suggest improvement of executive functioning as demonstrated by no degradation of performance on HVLT-R and faster scores on the Trails Making B Test (FIG. 7). This is notable because these are the primary cognitive tests that reveal poorer performance in multiple brain mestastases patients after whole brain radiation therapy.

Figure 8:
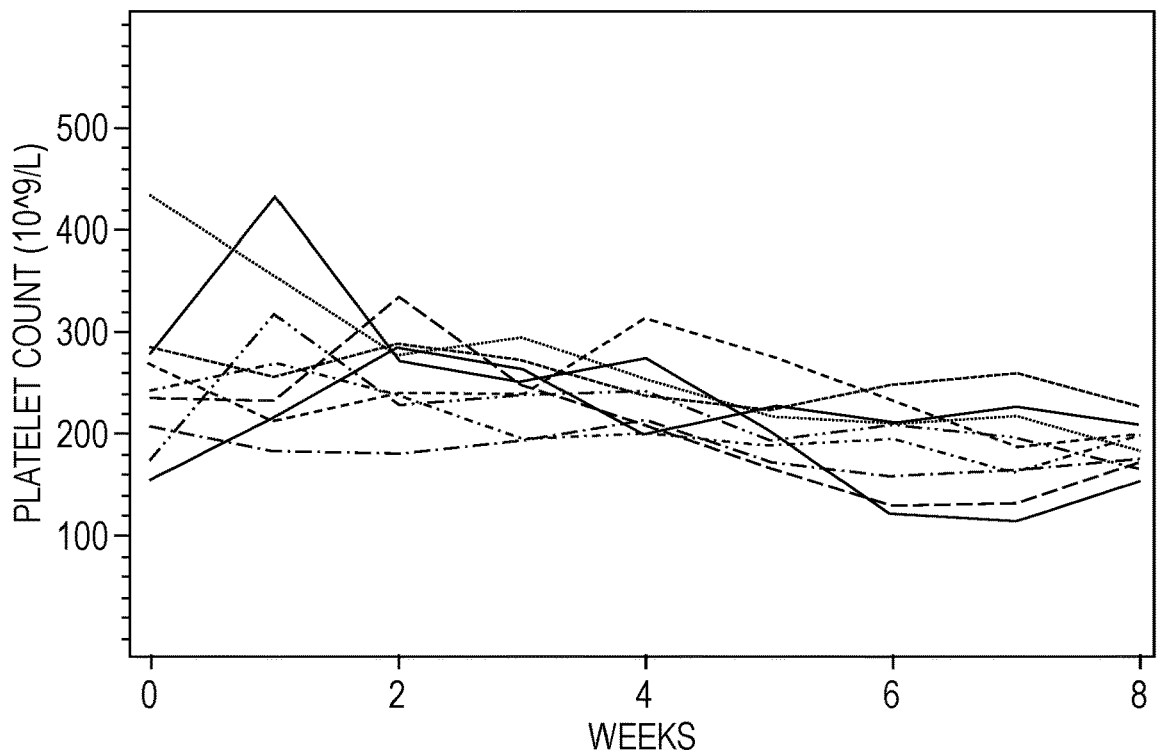
FIG. 8 shows graphs demonstrating the use of BMX-001 to protect against thrombocytopenia, a common side effect in HGG patients treated with radiation and temozolomide. Platelet counts in high-grade glioma patients receiving radiation/temozolomide with (left panel) and without (right panel) BMX-001. Each line represents a separate patient. N=9 for patients receiving BMX-001+chemoradiation, n=20 for patients receiving chemoradiation alone. The thrombocytopenia occurring in approximately 50% of subjects receiving chemoradiation for high-grade glioma patients is related primarily to the use of temozolomide. These patients are at risk of bleeding and are forced to suspend treatments. The data support the conclusion that BMX-001 prevents chemotherapy-induced bone marrow suppression at administered doses between 7 mg and 28 mg/subject load, followed by one-half the loading dose administered biweekly. The results show that BMX-001 distributes to the bone marrow and protects against oxidant-mediated damage.
Figure 8:
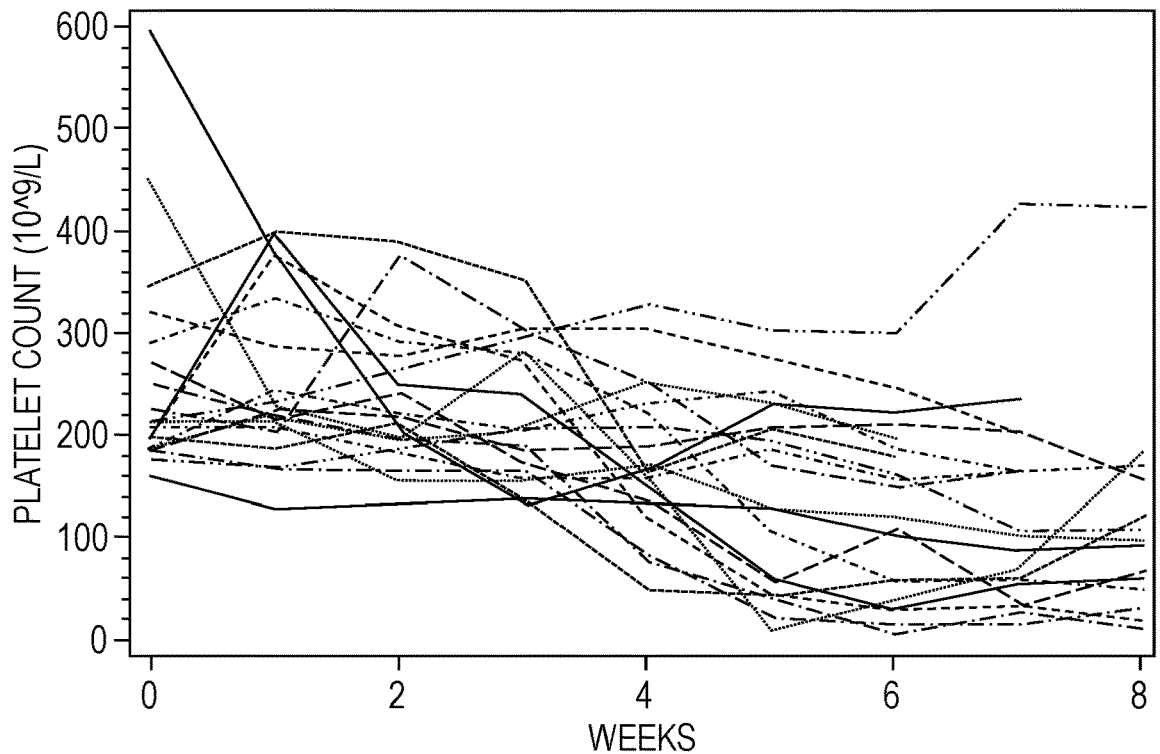

Chemoprotection of Bone Marrow by BMX-001 in Patients with High-Grade Glioma Receiving Radiation Therapy and Temozolomide In the above described human clinical trial, marked bone marrow protection has been observed as shown in FIG. 8. In patients receiving temozolomide the standard of care is to stop therapy for patients developing a platelet count below 100,000. None of the nine patients receiving BMX-001+temozolomide developed platelet counts below 100,000. In contrast, 9 out of 20 patients who did not receive BMX-001 in combination with temozolomide developed platelets below 100,000.

The thrombocytopenia occurring in approximately 50% of subjects receiving chemoradiation for high-grade glioma patients is related to the use of temozolomide. The data supports the conclusion that BMX-001 is effective in preventing chemotherapy-induced bone marrow suppression at administered loading doses between 7 mg and 28 mg/subject followed by one-half the loading dose administered biweekly as the maintenance dose.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP accession numbers, and other references cited herein are incorporated by reference in their entireties for the teachings relevant to the sentence and/or paragraph in which the reference is presented.

That which is claimed is:

1. A method of treating and/or preventing one or more side effects associated with chemotherapy exposure in a subject during and/or following chemotherapy exposure, the method comprising:

administering to the subject prior to, during, or after chemotherapy exposure an active agent at a loading dose in an amount of about 0.05 mg/kg to about 1 mg/kg times the activity equivalent of BMX-001;

wherein the active agent is a meso-substituted metalloporphyrin.

2. The method of claim 1, wherein the active agent is a superoxide dismutase (SOD) mimetic.

3. The method of claim 1, wherein the active agent is a compound of Formula I:

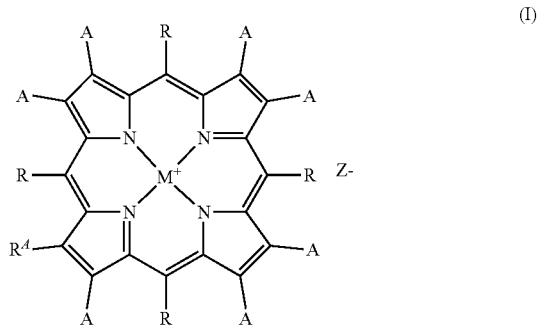

wherein:
each R is independently selected from a substituted or unsubstituted aryl, heteroaryl, cycloalkyl, or heterocycloalkyl;

each A is an independently selected from a hydrogen, an electron-withdrawing group, or an electron donating group;

M is a metal; and

Z— is a counterion;

or a pharmaceutically acceptable salt thereof.

4. The method of claim 1, wherein the active agent has a structure of Formula A1:

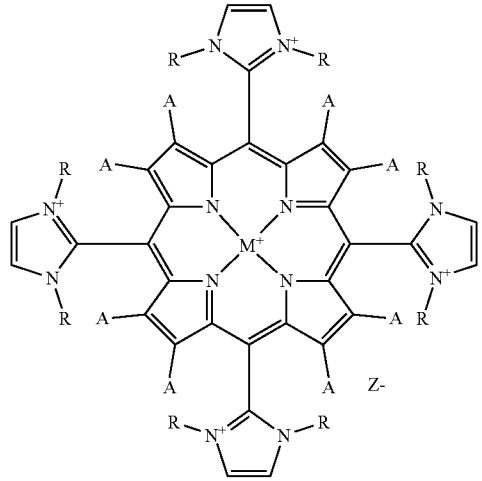

(A1)

wherein:
  each R is independently C1-12 alkyl or C1-C12 alkoxy-alkyl;
  each A is, independently, hydrogen or an electron withdrawing group;
  M is a metal selected from the group consisting of manganese, iron, copper, cobalt, and nickel; and
  Z— is a counterion;
  or a pharmaceutically acceptable salt thereof.

5. The method of claim 1, wherein the active agent has a structure of Formula B1:

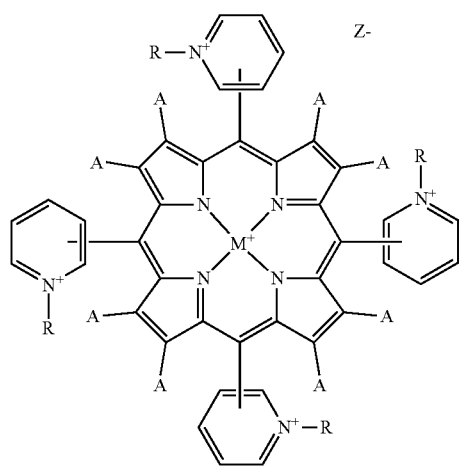

(B1)

wherein:
  each R is independently C1-12 alkyl or C1-C12 alkoxy-alkyl;
  each A is, independently, hydrogen or an electron withdrawing group;
  M is a metal selected from the group consisting of manganese, iron, copper, cobalt, and nickel; and
  Z— is a counterion;
  or a pharmaceutically acceptable salt thereof.

6. The method of claim 1, wherein said active agent has a structure of Formula C1:

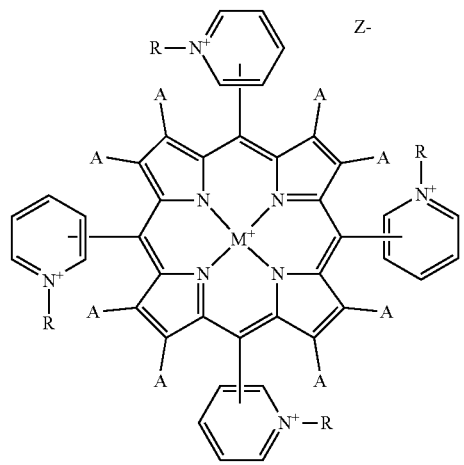

(C1)

wherein:
  each R is, independently, hydrogen or —(CH$_2$)$_m$CH$_2$OX;
  m is 1 or 2;
  X is C1-12 alkyl;
  each A is, independently, hydrogen or an electron withdrawing group;
  M is a metal selected from the group consisting of manganese, iron, copper, cobalt, and nickel; and
  Z— is a counterion;
  or a pharmaceutically acceptable salt thereof.

7. The method of claim 1, wherein the active agent has the structure:

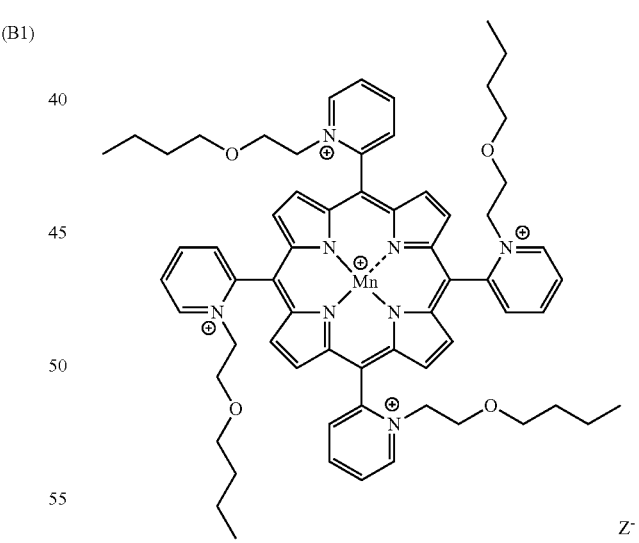

wherein Z$^-$ is a counterion; or a pharmaceutically acceptable salt thereof.

8. The method of claim 1, wherein the loading dose is administered to the subject in an amount of about 0.1 mg/kg to about 0.6 mg/kg or about 0.1 mg/kg to about 0.6 mg/kg times the activity equivalent of BMX-001.

9. The method of claim 1, wherein the loading dose is administered to the subject at about 30 minutes to about 4 days prior to the subject being exposed to the chemotherapy.

10. The method of claim 1, wherein the loading dose is administered to the subject during and/or after the subject is exposed to the chemotherapy.

11. The method of claim 1, further comprising administering to the subject the active agent at a maintenance dose in an amount that is about 25% to about 75% less than the amount of the active agent in the loading dose.

12. The method of claim 1, wherein the amount of active agent administered to the subject in the loading dose is about 5 mg to about 50 mg.

13. The method of claim 1, wherein the loading dose is only administered one time as the initial dose.

14. The method of claim 1, further comprising administering to the subject a maintenance dose, wherein the amount of the active agent administered to the subject in the maintenance dose is about 5 mg/week to about 50 mg/week times the activity equivalent of BMX-001.

15. The method of claim 1, further comprising administering to the subject a maintenance dose, wherein the maintenance dose is administered to the subject two or three times per week.

16. The method of claim 1, further comprising administering to the subject a maintenance dose, wherein the maintenance dose is administered two or three times a week after an initial chemotherapy exposure.

17. The method of claim 1, further comprising administering to the subject a maintenance dose, wherein the maintenance dose is administered every two or three days for 1 to 8 weeks after a final chemotherapy exposure.

18. The method of claim 1, wherein the subject is further receiving radiation therapy.

19. The method of claim 18, wherein the method treats and/or prevents radiation-induced normal tissue injury in the subject.

20. The method of claim 18, wherein the method treats and/or prevents one or more side effects associated with the radiation therapy.

21. A method of treating and/or preventing one or more side effects associated with radiation and/or chemotherapy exposure in a subject during and/or following radiation and/or chemotherapy exposure, the method comprising:
administering to the subject prior to, during, or after radiation and/or chemotherapy exposure an active agent at a loading dose in an amount of about 0.05 mg/kg to about 1 mg/kg times the activity equivalent of BMX-001;
wherein the active agent is a meso-substituted metalloporphyrin, and
wherein the loading dose is only administered one time as an initial dose.

22. The method of claim 21, wherein the active agent is a compound of Formula I:

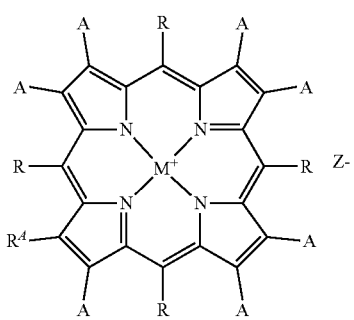

wherein:
each R is independently selected from a substituted or unsubstituted aryl, heteroaryl, cycloalkyl, or heterocycloalkyl;
each A is an independently selected from a hydrogen, an electron-withdrawing group, or an electron donating group;
M is a metal; and
Z— is a counterion;
or a pharmaceutically acceptable salt thereof.

23. The method of claim 21, wherein the active agent has a structure of Formula A1:

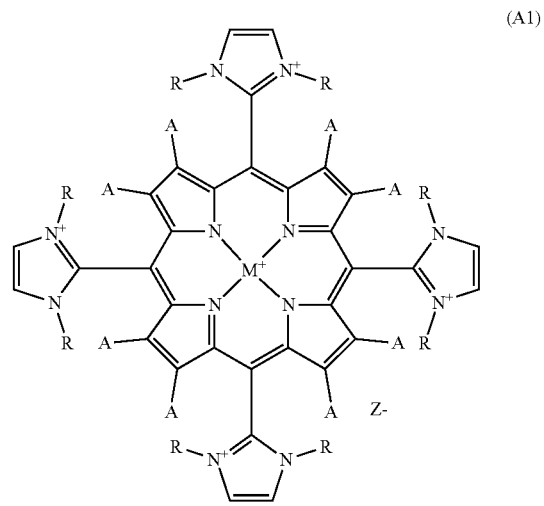

wherein:
each R is independently C1-12 alkyl or C1-C12 alkoxyalkyl;
each A is, independently, hydrogen or an electron withdrawing group;
M is a metal selected from the group consisting of manganese, iron, copper, cobalt, and nickel; and
Z— is a counterion;
or a pharmaceutically acceptable salt thereof.

24. The method of claim 21, wherein the active agent has a structure of Formula B1:

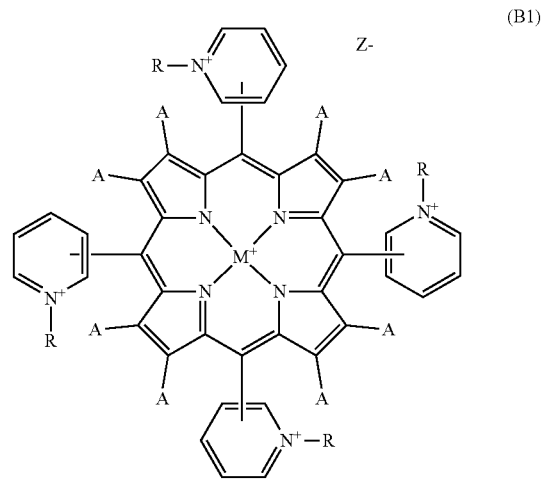

wherein:
each R is independently C1-12 alkyl or C1-C12 alkoxyalkyl;
each A is, independently, hydrogen or an electron withdrawing group;
M is a metal selected from the group consisting of manganese, iron, copper, cobalt, and nickel; and
Z— is a counterion; or a pharmaceutically acceptable salt thereof.

25. The method of claim 21, wherein the active agent has the structure:

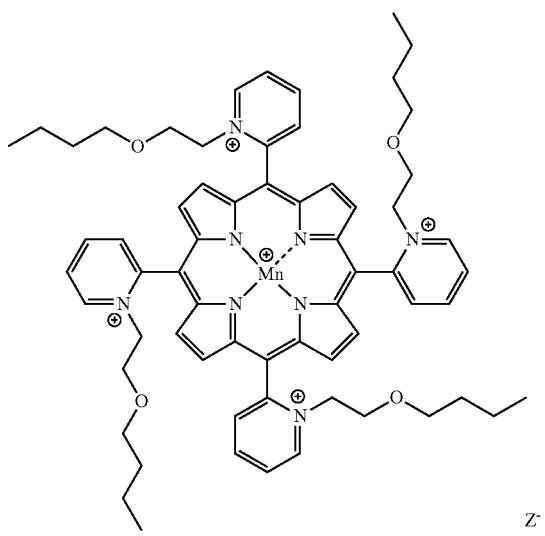

Z⁻ wherein Z⁻ is a counterion, or a pharmaceutically acceptable salt thereof.

26. The method of claim 21, wherein the loading dose is administered to the subject in an amount of about 0.1 mg/kg to about 0.6 mg/kg or about 0.1 mg/kg to about 0.6 mg/kg times the activity equivalent of BMX-001.

27. The method of claim 21, wherein the loading dose is administered to the subject at about 30 minutes to about 4 days prior to the subject being exposed to the radiation and/or chemotherapy.

28. The method of claim 21, wherein the loading dose is administered to the subject during and/or after the subject is exposed to the radiation and/or chemotherapy.

29. The method of claim 21, further comprising administering to the subject the active agent at a maintenance dose in an amount that is about 25% to about 75% less than the amount of the active agent in the loading dose.

30. The method of claim 21, wherein the amount of active agent administered to the subject in the loading dose is about 5 mg to about 50 mg.

31. The method of claim 21, further comprising administering to the subject a maintenance dose, wherein the amount of active agent administered to the subject in the maintenance dose is about 5 mg/week to about 50 mg/week times the activity equivalent of BMX-001.

32. The method of claim 21, further comprising administering to the subject a maintenance dose, wherein the maintenance dose is administered to the subject two or three times per week.

33. The method of claim 21, further comprising administering to the subject a maintenance dose, wherein the maintenance dose is administered two or three times a week after an initial radiation and/or chemotherapy exposure.

34. The method of claim 21, further comprising administering to the subject a maintenance dose, wherein the maintenance dose is administered every two or three days for 1 to 8 weeks after a final radiation and/or chemotherapy exposure.

35. The method of claim 21, wherein the method treats or prevents one or more side effects associated with radiation exposure in a subject during and/or following radiation exposure and the method comprises administering to the subject the active agent prior to, during, or after the radiation exposure.

36. The method of claim 21, wherein the method treats or prevents one or more side effects associated with chemotherapy exposure in a subject during and/or following chemotherapy exposure and the method comprises administering to the subject the active agent prior to, during, or after the chemotherapy exposure.

37. A method of treating and/or preventing one or more side effects associated with radiation exposure in a subject during and/or following radiation exposure, optionally in combination with chemotherapy exposure, the method comprising:
administering to the subject prior to, during, or after radiation exposure, and optionally chemotherapy exposure, an active agent at a loading dose in an amount of about 0.05 mg/kg to about 1 mg/kg times the activity equivalent of BMX-001;
wherein the active agent is a meso-substituted metalloporphyrin, and
wherein the radiation exposure comprises at least one radiation treatment that is administered 5 days a week for 1 to 10 weeks.

38. The method of claim 37, wherein the active agent is a compound of Formula I:

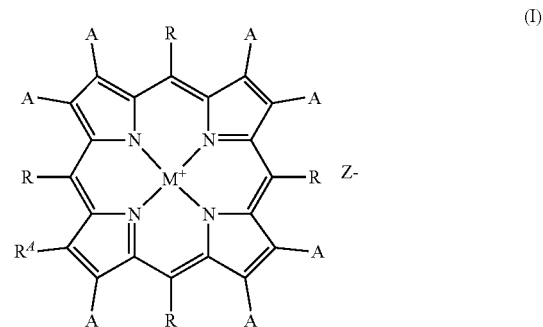

(I)

wherein:
each R is independently selected from a substituted or unsubstituted aryl, heteroaryl, cycloalkyl, or heterocycloalkyl;
each A is an independently selected from a hydrogen, an electron-withdrawing group, or an electron donating group;
M is a metal; and
Z— is a counterion;
or a pharmaceutically acceptable salt thereof.

39. The method of claim 37, wherein the active agent has a structure of Formula A1:1

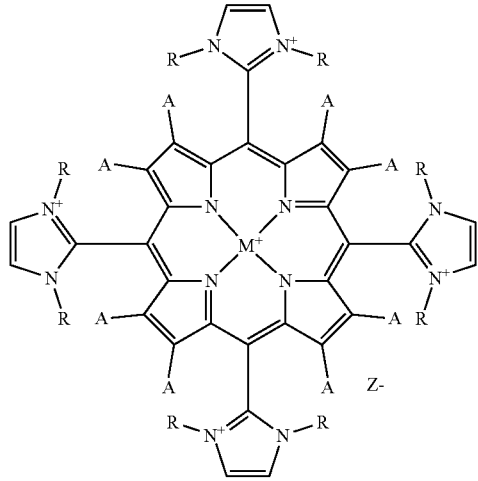

(A1)

wherein:
each R is independently C1-12 alkyl or C1-C12 alkoxyalkyl;
each A is, independently, hydrogen or an electron withdrawing group;
M is a metal selected from the group consisting of manganese, iron, copper, cobalt, and nickel; and
Z— is a counterion;
or a pharmaceutically acceptable salt thereof.

40. The method of claim 37, wherein the active agent has a structure of Formula B1:

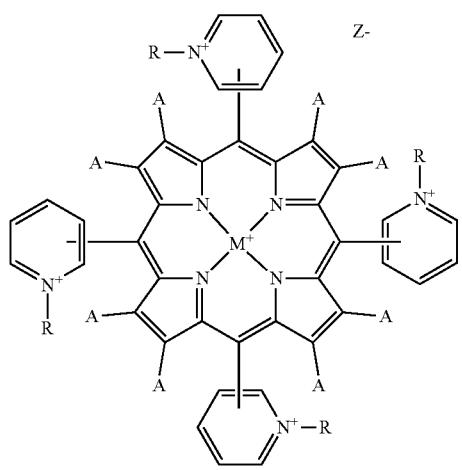

(B1)

wherein:
each R is independently C1-12 alkyl or C1-C12 alkoxyalkyl;
each A is, independently, hydrogen or an electron withdrawing group;
M is a metal selected from the group consisting of manganese, iron, copper, cobalt, and nickel; and
Z— is a counterion;
or a pharmaceutically acceptable salt thereof.

41. The method of claim 37, wherein the active agent has the structure:

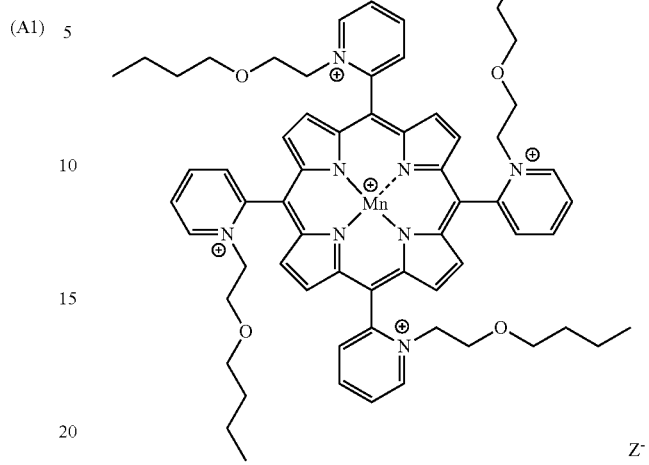

wherein $Z^-$ is a counterion; or
a pharmaceutically acceptable salt thereof.

42. The method of claim 37, wherein the loading dose is administered to the subject in an amount of about 0.1 mg/kg to about 0.6 mg/kg or about 0.1 mg/kg to about 0.6 mg/kg times the activity equivalent of BMX-001.

43. The method of claim 37, wherein the loading dose is administered to the subject at about 30 minutes to about 4 days prior to the subject being exposed to the radiation and optionally chemotherapy.

44. The method of claim 37, wherein the loading dose is administered to the subject during and/or after the subject is exposed to the radiation and optionally chemotherapy.

45. The method of claim 37, further comprising administering to the subject the active agent at a maintenance dose in an amount that is about 25% to about 75% less than the amount of the active agent in the loading dose.

46. The method of claim 37, wherein the amount of active agent administered to the subject in the loading dose is about 5 mg to about 50 mg.

47. The method of claim 37, wherein the loading dose is only administered one time as the initial dose.

48. The method of claim 27, further comprising administering to the subject a maintenance dose, wherein the amount of active agent administered to the subject in the maintenance dose is about 5 mg/week to about 50 mg/week times the activity equivalent of BMX-001.

49. The method of claim 37, further comprising administering to the subject a maintenance dose, wherein the maintenance dose is administered to the subject two or three times per week.

50. The method of claim 37, further comprising administering to the subject a maintenance dose, wherein the maintenance dose is administered two or three times a week after an initial radiation and/or chemotherapy exposure.

51. The method of claim 37, further comprising administering to the subject a maintenance dose, wherein the maintenance dose is administered every two or three days for 1 to 8 weeks after a final radiation and/or chemotherapy exposure.

52. The method of claim 37, wherein the method treats or prevents one or more side effects associated with radiation and chemotherapy exposure in a subject during and/or following radiation and chemotherapy exposure and the method comprises administering to the subject the active agent prior to, during, or after the radiation and chemotherapy exposure.

\* \* \* \* \*

UNITED STATES PATENT AND TRADEMARK OFFICE
CERTIFICATE OF CORRECTION

PATENT NO. : 11,285,162 B2
APPLICATION NO. : 16/500490
DATED : March 29, 2022
INVENTOR(S) : Ashcraft et al.

Page 1 of 1

It is certified that error appears in the above-identified patent and that said Letters Patent is hereby corrected as shown below:

In the Specification

Column 3, Line 51: Please correct "$g_s$=8V/ID" to read -- $g_s$=8$V_L$/D --

Column 4, Line 10: Please insert a paragraph break between "control" and "FIG. 4C"

Column 9, Line 52: Please correct "—N($R_e$)C(O)N$R_a R_b$" to read -- —N($R_c$)C(O)N$R_a R_b$ --

Column 35, Line 29: Please correct "NF-xB" to read -- NF-κB --

Column 42, Line 53: Please correct "100 mg/m2" to read -- 100 mg/m$^2$ --

Column 42, Line 55: Please correct "30-40 mg/m2" to read -- 30-40 mg/m$^2$ --

In the Claims

Column 62, Line 46, Claim 48: Please correct "claim 27" to read -- claim 37 --

Signed and Sealed this
Sixth Day of September, 2022

Katherine Kelly Vidal
*Director of the United States Patent and Trademark Office*